US011530221B2

(12) United States Patent
Han et al.

(10) Patent No.: US 11,530,221 B2
(45) Date of Patent: Dec. 20, 2022

(54) PYRIMIDO[4,5-D]PYRIMIDIN-2-ONE DERIVATIVES AS PROTEIN KINASE INHIBITORS

(71) Applicant: KOREA INSTITUTE OF SCIENCE AND TECHNOLOGY, Seoul (KR)

(72) Inventors: Seo Jung Han, Seoul (KR); Tae Bo Sim, Seoul (KR); Do Hee Oh, Seoul (KR); Jae Eun Cheong, Seoul (KR); Dong Keon Hwang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 98 days.

(21) Appl. No.: 17/002,748

(22) Filed: Aug. 25, 2020

(65) Prior Publication Data

US 2021/0061810 A1 Mar. 4, 2021

(30) Foreign Application Priority Data

Aug. 30, 2019 (KR) .................. 10-2019-0107018

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC ................................ C07D 487/04; A61P 35/00
See application file for complete search history.

(56) References Cited

U.S. PATENT DOCUMENTS 8,058,283 B2   11/2011   Honold et al.

FOREIGN PATENT DOCUMENTS

| EP | 3 048 099 A2 | 7/2016 |
|---|---|---|
| WO | 96-34867 A1 | 11/1996 |
| WO | 2005-011597 A2 | 2/2005 |
| WO | 2005/011597 A2 | 2/2005 |
| WO | WO 2005/011597 * | 2/2005 |
| WO | 2006/135824 A1 | 12/2006 |
| WO | 2012-167415 A1 | 12/2012 |
| WO | 2018/102795 A2 | 6/2018 |
| WO | 2019-091476 A1 | 5/2019 |

OTHER PUBLICATIONS

Hanna Cho et al., First SAR Study for Overriding NRAS Mutant Driven Acute Myeloid Leukemia, Journal of Medicinal Chemistry, Aug. 28, 2018, pp. 8353-8373, vol. 61.
Jonghwa Won et al., T-Cell-Targeted Signaling Inhibitors. International Reviews of Immunology, 2008, pp. 19-41, vol. 27.
Hwan Geun Choi et al., A type-II kinase inhibitor capable of inhibiting the T315I "gatekeeper" mutant of Bcr-Abl. Journal of Medicinal Chemistry, Jul. 6, 2010, pp. 5439-5448, vol. 53, No. 15.
Atsushi Nonami et al., Identification of novel therapeutic targets in acute leukemias with NRAS mutations using a pharmacologic approach. Blood, May 14, 2015, pp. 3133-3143, vol. 125, No. 20.
Gorke Peris et al., Aspaitale-Catalyzed Asymmetric Epoxidation Reactions, J. Am. Chem. Soc. Jun. 26, 2007, pp. 8710-8711, vol. 129, No. 28.
Jay Chauhan et al., Synthetic, structural mimetics of the β-hairpin flap of HIV-1 protease inhibit enzyme function, Bioorganic& Medicinal Chemistry, Sep. 7, 2015, pp. 7095-7109, vol. 23.
Aurélie A. et al., γ-Turn Mimicry with Benzodiazepinones and Pyrrolobenzodiazepinones Synthesized from a Common Amino Ketone Intermediate, Organic Letters, Jun. 30, 2015, pp. 3592-3595, vol. 17.
Landon R. Whitby et al., Design, Synthesis, and Validation of a β-Turn Mimetic Library Targeting Protein-Protein and Peptide-Receptor Interactions, Journal of the American Chemical Society, May 24, 2011, pp. 10184-10194, vol. 133.
Alex Shaginian et al., Design, Synthesis, and Evaluation of an α-Helix Mimetic Library Targeting Protein-Protein Interactions, J. Am. Chem. Soc. Mar. 31, 2009, pp. 5564-5572. vol. 131.

\* cited by examiner

*Primary Examiner* — Erich A Leeser
(74) *Attorney, Agent, or Firm* — Goldilocks Zone IP Law

(57) ABSTRACT

Disclosed are a compound selected from novel pyrimido[4,5-d]pyrimidin-2-one derivative compounds having excellent anti-proliferative activity against cancer cells, pharmaceutically acceptable salts thereof, hydrates thereof and stereoisomers thereof, a method for preparing the compound, a pharmaceutical composition for preventing, alleviating or treating cancer metastasis and proliferative diseases containing the compound as an active ingredient, and an anticancer composition against cancer cells, containing the compound as an active ingredient. The compounds of this invention exhibit most excellent selective inhibitory activity against LCK and anti-proliferative activity against cancer cells, thus being useful for inhibiting cancer cells, and for preventing or treating cancer metastasis and proliferative diseases.

11 Claims, No Drawings

PYRIMIDO[4,5-D]PYRIMIDIN-2-ONE DERIVATIVES AS PROTEIN KINASE INHIBITORS

CROSS-REFERENCE TO RELATED APPLICATION

This application claims, under 35 U.S.C. § 119(a), the benefit of priority to Korean Patent Application No. 10-2019-0107018, filed on Aug. 30, 2019, the entire contents of which are incorporated herein by reference.

BACKGROUND

(a) Technical Field

The present invention relates to a compound selected from novel pyrimido[4,5-d]pyrimidin-2-one derivative compounds having very selective protein kinase inhibitory activity, pharmaceutically acceptable salts thereof, hydrates thereof and stereoisomers thereof, a method for preparing the compound, and a pharmaceutical composition for preventing, alleviating or treating cancer containing the compound as an active ingredient.

(b) Background Art

Protein kinases are enzymes that catalyze the phosphorylation reaction to transfer the gamma-phosphate group of ATP to the hydroxy group of tyrosine, serine and threonine of proteins, are responsible for cell metabolism, gene expression, cell growth, cell differentiation and cell division, and play an important role in cell signaling.

Protein kinases occupy about 2% of the eukaryotic genome, and there are about 518 types of protein kinases in the human genome. Protein kinases are classified into tyrosine protein kinases, which phosphorylate tyrosine, and serine/threonine kinases, which phosphorylate serine and threonine. About 90 or more of these are tyrosine kinases, which are divided into receptor tyrosine kinases (RTK) and non-receptor tyrosine kinases (NRTK). The receptor tyrosine kinases are membrane proteins that have a domain capable of accommodating growth factors on the cell surface and an active site capable of phosphorylating tyrosine residues in the cytoplasm. The non-receptor tyrosine kinases receive a signal using a single tyrosine kinase domain that exists in the nucleus and cytoplasm to phosphorylate the tyrosine residue although they do not have the shape of a receptor.

Protein kinases are molecular switches, and the transition between active and inactive states in cells should be smoothly regulated. Abnormal regulation excessively activates intracellular signal transmission, leading to uncontrollable cell division and proliferation. In addition, abnormal activation of protein kinases due to gene mutations, amplification and overexpression is related to the development and progression of various tumors, and thus is critical in the growth and metastasis of cancer cells. Representative protein kinases that are abnormally regulated include EGFR, VEGFR, PDGFRB, c-KIT, ABL1, SRC, BRAF, FGFR, BTK, SYK, ALK, MET, CDK, MEK, mTOR, JAK, LCK, PLK, RSK, LYN, FMS, TIE2, RET, AKT, MAP, FAK, DDR, FLT3, FES and the like. In particular, the receptor tyrosine kinases are mainly involved in signaling pathways regarding internal reactions and external signals associated with cell growth. Thus, inhibition in cancer cell growth and cell death can be induced by suppressing the receptor tyrosine kinases.

Based on these characteristics, the inhibition of kinase activity is attracting attention as a major target for the development of anticancer drugs, and research on the development of low-molecular organic compounds targeting various kinases has been actively conducted.

Kinase inhibitors include, as a Bcr-Abl and PDGFR tyrosine kinase inhibitor, Gleevec® (imatinib, Novartis), as a Her-2 antibody, Herceptin® (trastuzumab, Genentech), as an EGFR inhibitor, Iressa® (gefitinib, AstraZeneca), as Raf, VEGFR, KIT, RET, PDGFR-B and FLT-3 inhibitors, Nexavar® (sorafenib, Bayer), as a BRAF inhibitor, Zelboraf® (vemurafenib, Roche), as an EGFR antibody, Erbitux® (cetuximab, Imclone), as an EGFR inhibitor, Tarceva® (erlotinib, Genentech/Roche), and as a KDR inhibitor, Sutent® (sunitinib, Pfizer). These were approved by the FDA as anticancer drugs for diseases such as leukemia, breast cancer, non-small-cell lung cancer, liver cancer, malignant melanoma and colorectal cancer, and are widely used in primary standard therapies owing to the excellent treatment efficacy thereof. Furthermore, several additional compounds are in clinical trials.

LCK (lymphocyte-specific protein tyrosine kinase) is a member of Src kinase, which is a 56 kDa non-receptor tyrosine kinase, and is expressed in T-cells and NK-cells and in the brain. LCK phosphorylates a number of kinases such as ZAP-70, ITK, PI3K, and PKC and affects cell cycle and cell. Since LCK plays an important role in T-cell proliferation, differentiation and migration. LCK interacts with the cytoplasmic domains of CD4 and CD8 and the beta chain of the IL-2 receptor to induce TCR-mediated T-cell activation proliferation and differentiation, LCK is an essential molecular target for T-cell-related diseases. LCK overexpression causes a variety of disorders and syndromes including organ transplant rejection, cancer, inflammation, rheumatoid arthritis, asthma, type 1 diabetes, psoriasis, Crohn's disease, and atherosclerosis. LCK may be a molecular target for colon cancer, chronic lymphocytic leukemia (CLL), thymoma and malignant glioblastoma target therapies.

PRIOR ART DOCUMENT

Patent Document (Patent Document 1) International Patent Application No. WO 2005-011597

Non-Patent Document (Non-Patent Document 1) Choi H. G., Ren P., Adrian F., et al. A type-II kinase inhibitor capable of inhibiting the T3151 "gatekeeper" mutant of Bcr-Abl. J. Med. Chem., 2010; 53(15): 5439-5448.

(Non-Patent Document 2) Nonami, A.; Sattler, M.; Weisberg, E.; Liu, Q.; Zhang, J.; Patricelli, M. P.; Christie, A. L.; Saur, A. M.; Kohl, N. E.; Kung, A. L.; Yoon, H.; Sim, T.; Gray, N. S.; Griffin, J. D., Identification of novel therapeutic targets in acute leukemias with NRAS mutations using a pharmacologic approach. Blood 2015, 125 (20); 3133-3143.

(Non-Patent Document 3) H Cho, I Shin, E Ju, et al. First SAR Study for Overriding NRAS Mutant-Driven Acute Myeloid Leukemia. J. Med. Chem. 2018, 61 (18); 8353-8373

SUMMARY OF THE DISCLOSURE

The present invention has been made in an effort to solve the above-described problems associated with the prior art.

It is one object of the present invention to provide a novel pyrimido[4,5-d]pyrimidin-2-one derivative compound having selective inhibitory activity against protein kinases.

It is another object of the present invention to provide a pharmaceutical composition useful for treating, preventing and alleviating cancer-related diseases containing, as an active ingredient, a novel pyrimido[4,5-d]pyrimidin-2-one derivative compound, a pharmaceutically acceptable salt thereof, a hydrate thereof or a stereoisomer thereof.

It is another object of the present invention to provide a therapeutic agent for cancer-related diseases, inflammatory diseases and immune diseases caused by overexpression and mutation of LCK, DDR1, FGR, BMX, ABL2, BLX, BLK, LYN, DDR2, RAF1, c-src, CS and HCK kinases, containing, as an active ingredient, a novel pyrimido[4,5-d]pyrimidin-2-one derivative compound, a pharmaceutically acceptable salt thereof, a hydrate thereof or a stereoisomer thereof.

In one aspect, the present invention provides a compound selected from a pyrimido[4,5-d]pyrimidin-2-one derivative compound represented by any one of the following Formulae 1 to 6, a pharmaceutically acceptable salt thereof, a hydrate thereof and a stereoisomer thereof:

[Formula 1]

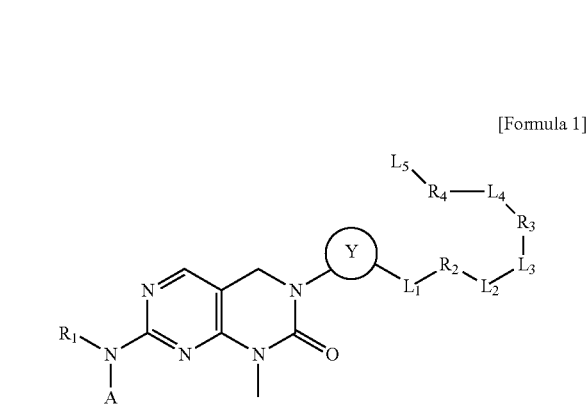

[Formula 2]

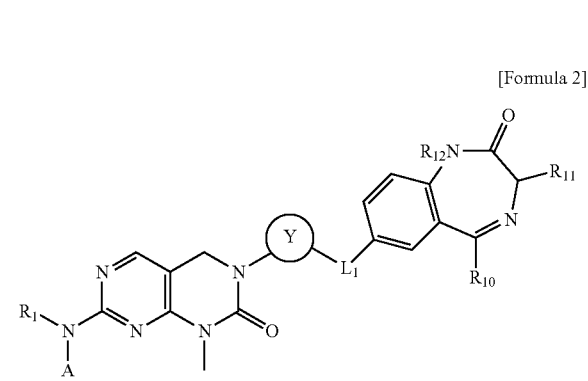

[Formula 3]

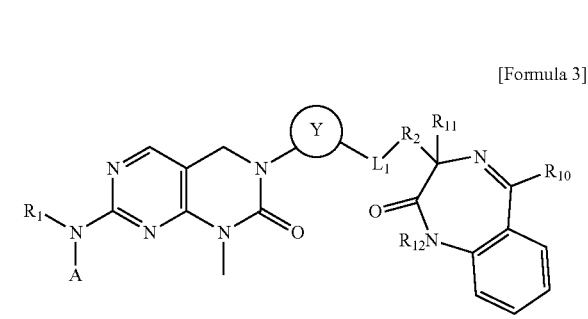

[Formula 4]

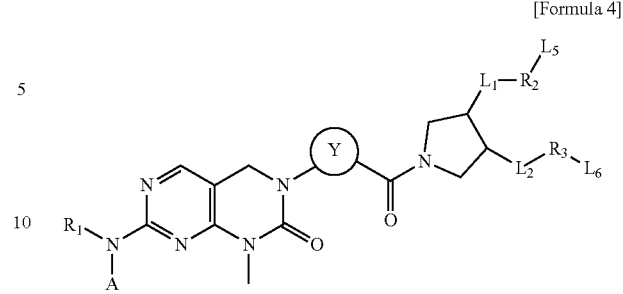

[Formula 5]

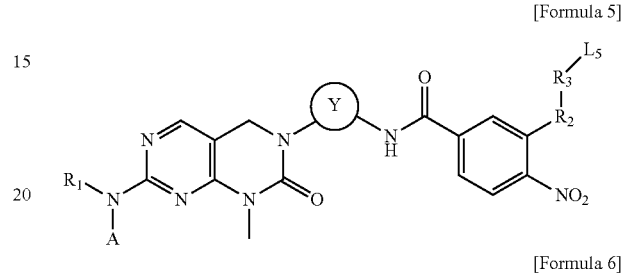

[Formula 6]

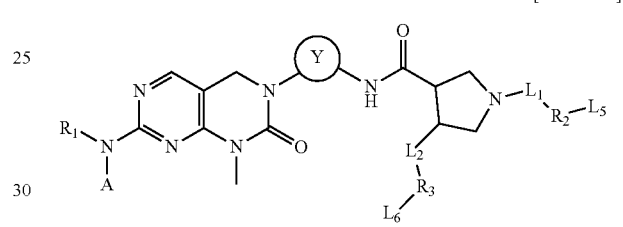

wherein $R_1$ is hydrogen; a $C_1$-$C_{13}$ alkyl group; a $C_3$-$C_{10}$ cyclic group; or a $C_3$-$C_{10}$ heterocyclic group;

A is hydrogen; a $C_1$-$C_{13}$ alkyl group; a $C_6$-$C_{10}$ aryl group; a $C_3$-$C_{10}$ cyclic group; a $C_3$-$C_{10}$ heteroaryl group; a $C_3$-$C_{10}$ heterocyclic group; or —C(O)—($C_1$-$C_{13}$ alkyl);

Y is a $C_6$-$C_{10}$ aryl group; or a 5-membered to 9-membered heteroaryl group containing one to four heteroatoms selected from nitrogen (N), oxygen (O) and sulfur (S) atoms;

$L_1$, $L_2$, $L_3$ and $L_4$ are each independently selected from the group consisting of —$NR_5$—; —$NR_5CH_2$—; —$NR_5C(O)$—; —$C(O)NR_5$—; —$NR_5C(O)NR_5$—; —$S(O)_2$—; —$NR_5S(O)_2$—; —$S(O)_2NR_5$—; —O—; —$CH_2$—; —CH($CH_3$)—; —C(O)O—; —C(O)—;

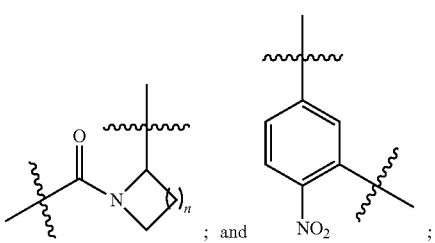

; and $L_5$ and $L_6$ are each independently —$C(O)NR_5R_6$; —$CR_5R_6R_7$; —$OR_5$; —$CCl_3$, a $C_1$-$C_6$ alkyl group; a $C_3$-$C_{10}$ cyclic group; -substituted or unsubstituted benzene; -substituted or unsubstituted indole; -substituted or unsubstituted phenyl; -substituted or unsubstituted hexane; -substituted or unsubstituted furan; -substituted or unsubstituted thiophene; -substituted or unsubstituted pyridine; -substituted or unsubstituted benzofuran; -substituted or unsubstituted naphthalene; -substituted or unsubstituted anthracene; or -substituted or unsubstituted phenanthrene;

$R_2$, $R_3$ and $R_4$ are each independently —O—; —$CH_2$—; —CH($CH_3$)—; —$CR_5R_6$—; —$NR_5$—; —$NR_5CH_2$—; —$NR_5C(O)$—; —$C(O)NR_5$—; —$NR_5C(O)NR_5$—; —$S(O)_2$—; —$NR_5S(O)_2$—; or —$C_3$-$C_{10}$ cyclic group-;

$R_5$, $R_6$ and $R_7$ are each independently hydrogen; halogen; a $C_1$-$C_6$ alkyl group; a $C_3$-$C_{10}$ cyclic group; a $C_6$-$C_{10}$ aryl group; or —$CH_2$(Ph), $R_{10}$, $R_{11}$ and $R_{12}$ are each independently hydrogen; a $C_1$-$C_{13}$ alkyl group; a $C_6$-$C_{10}$ aryl group; a $C_3$-$C_{10}$ cyclic group; a $C_3$-$C_{10}$ heteroaryl group; a $C_3$-$C_{10}$ heterocyclic group; —C(O)—($C_1$-$C_{13}$ alkyl); —$CH_2$(Ph), —$CH_2$(Ph)$R_5$, a benzyl group; or —$CH_2CH\!=\!CH_2$, and N is 0, 1, 2, 3 or 4, wherein the $C_1$-$C_6$ alkyl group, $C_1$-$C_{13}$ alkyl group or $C_3$-$C_{10}$ cyclic group includes at least one substituent selected from the group consisting of hydrogen; a hydroxy group; a halogen group; a $C_1$-$C_{13}$ alkyl group; a $C_1$-$C_6$ alkoxy group; an amino group (—$NR_8R_9$); a nitro group (—$N(O)_2$); an amide group (—(C=O)$NR_8R_9$); a carboxylic group (—C(O)OH), a nitrile group (—CN), a urea group (—$NR_8$(C=O)$NR_9$—); a sulfonamide group (—$NHS(O)_2$—); a sulfide group (—S—); a sulfone group (—$S(O)_2$—); a phosphoryl group (—$P(O)R_8R_9$); a $C_6$-$C_{10}$ aryl group; a $C_3$-$C_{10}$ heteroaryl group; and a $C_3$-$C_{10}$ heterocyclic group, the $C_6$-$C_{10}$ aryl group, $C_3$-$C_{10}$ heteroaryl group or $C_3$-$C_{10}$ heterocyclic group includes at least one substituent selected from the group consisting of hydrogen; a hydroxy group; a halogen group; a carbonyl group (—(C=O)$R_8R_9$); a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—$NR_8R_9$); a nitro group (—$N(O)_2$); an amide group (—(C=O)$NR_8R_9$); a carboxylic group (—C(O)OH), a nitrile group (—CN), a urea group (—$NR_8$(C=O)$NR_9$—); a sulfonamide group (—$NHS(O)_2$—); a sulfide group (—S—); a sulfone group (—$S(O)_2$—); a phosphoryl group (—$P(O)R_8R_9$); a $C_6$-$C_{10}$ aryl group; a $C_3$-$C_{10}$ heteroaryl group; and a $C_3$-$C_{10}$ heterocyclic group, $R_8$ and $R_9$ described above include at least one selected from the group consisting of hydrogen; a $C_1$-$C_6$ alkyl group; a $C_1$-$C_6$ alkenyl group; a $C_1$-$C_6$ alkynyl group; a $C_6$-$C_{10}$ aryl group; a $C_3$-$C_{10}$ heteroaryl group; and a $C_3$-$C_{10}$ heterocyclic group, and the $C_3$-$C_{10}$ heteroaryl group and $C_3$-$C_{10}$ heterocyclic group include at least one heteroatom selected from the group consisting of N, O, and S.

Other aspects and preferred embodiments of the invention are discussed infra.

DETAILED DESCRIPTION

Unless the context clearly indicates otherwise, all numbers, figures and/or expressions that represent ingredients, reaction conditions, polymer compositions and amounts of mixtures used in the specification are approximations that reflect various uncertainties of measurement occurring inherently in obtaining these figures, among other things. For this reason, it should be understood that, in all cases, the term "about" should be understood to modify all numbers, figures and/or expressions. In addition, when numerical ranges are disclosed in the description, these ranges are continuous and include all numbers from the minimum to the maximum including the maximum within each range unless otherwise defined. Furthermore, when the range refers to an integer, it includes all integers from the minimum to the maximum including the maximum within the range, unless otherwise defined.

It should be understood that, in the specification, when a range is referred to regarding a parameter, the parameter encompasses all figures including end points disclosed within the range. For example, the range of "5 to 10" includes figures of 5, 6, 7, 8, 9, and 10, as well as arbitrary sub-ranges, such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include numbers such as 10%, 11%, 12% and 13% as well as 30%, and any sub-ranges, such as ranges of 10% to 15%, 12% to 18%, or 20% to 30%, as well as any numbers, such as 10.5%, 15.5% and 25.5%, between appropriate integers that fall within the range.

Hereinafter, the present invention will be described in detail.

As a result of continuous research to solve the above problems, the present inventors developed novel pyrimido[4,5-d]pyrimidin-2-one derivative compounds, which are useful for the prevention or treatment of cancer as anti-cancer compounds exhibiting excellent inhibitory activity against cancer cells, particularly as selective kinase activity inhibitors, pharmaceutically acceptable salts thereof, hydrates thereof and stereoisomers thereof, a method for preparing the same, and a pharmaceutical composition for preventing or treating cancer containing the same, as an active ingredient.

In one aspect, the present invention provides a compound selected from a pyrimido[4,5-d]pyrimidin-2-one derivative compound represented by any one of the following Formulae 1 to 6, a pharmaceutically acceptable salt thereof, a hydrate thereof and a stereoisomer thereof:

[Formula 1]

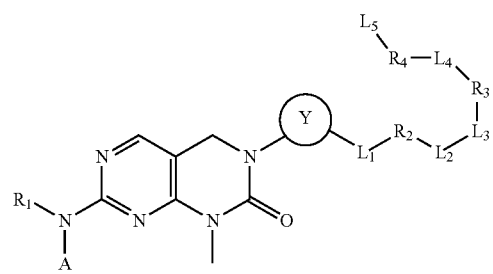

[Formula 2]

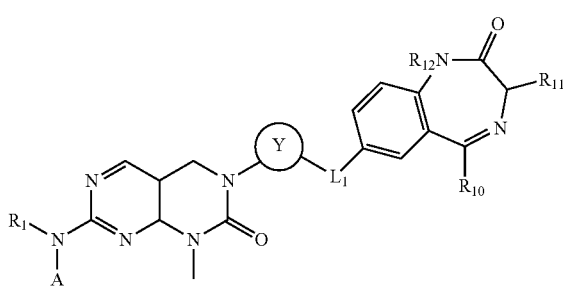

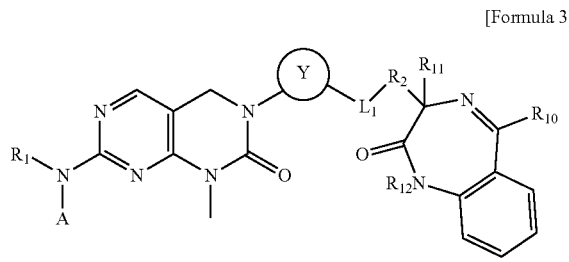

[Formula 3]

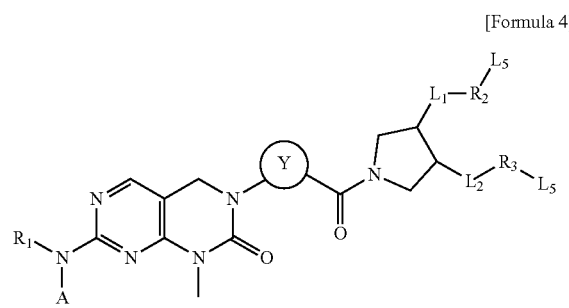

[Formula 4]

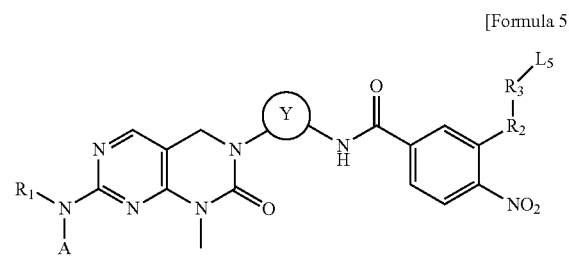

[Formula 5]

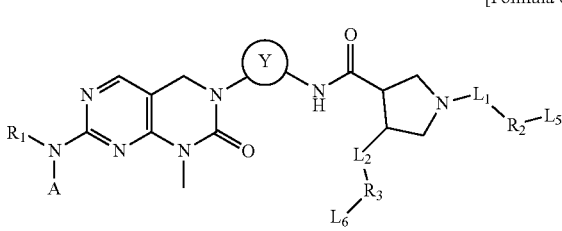

[Formula 6]

wherein $R_1$ is hydrogen; a $C_1$-$C_{13}$ alkyl group; a $C_3$-$C_{10}$ cyclic group; or a $C_3$-$C_{10}$ heterocyclic group;

A is hydrogen; a $C_1$-$C_{13}$ alkyl group; a $C_6$-$C_{10}$ aryl group; a $C_3$-$C_{10}$ cyclic group; a $C_3$-$C_{10}$ heteroaryl group; a $C_3$-$C_{10}$ heterocyclic group; or —C(O)—($C_1$-$C_{13}$ alkyl);

Y is a $C_6$-$C_{10}$ aryl group; or a 5-membered to 9-membered heteroaryl group containing one to four heteroatoms selected from nitrogen (N), oxygen (O) and sulfur (S) atoms;

$L_1$, $L_2$, $L_3$ and $L_4$ are each independently selected from the group consisting of —NR$_5$—; —NR$_5$CH$_2$—; —NR$_5$C(O)—; —C(O)NR$_5$—; —NR$_5$C(O)NR$_5$—; —S(O)$_2$—; —NR$_5$S(O)$_2$—; —S(O)$_2$NR$_5$—; —O—; —CH$_2$—; —CH(CH$_3$)—; —C(O)O—; —C(O)—;

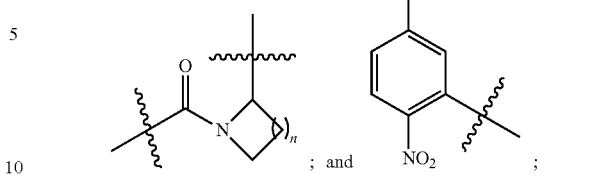

; and $L_5$ and $L_6$ are each independently —C(O)NR$_5$R$_6$; —CR$_5$R$_6$R$_7$; —OR$_5$; —CCl$_3$; a $C_1$-$C_6$ alkyl group; a $C_3$-$C_{10}$ cyclic group; -substituted or unsubstituted benzene; -substituted or unsubstituted indole; -substituted or unsubstituted phenyl; -substituted or unsubstituted hexane; -substituted or unsubstituted furan; -substituted or unsubstituted thiophene; -substituted or unsubstituted pyridine; -substituted or unsubstituted benzofuran; -substituted or unsubstituted naphthalene; -substituted or unsubstituted anthracene; or -substituted or unsubstituted phenathrene;

$R_2$, $R_3$ and $R_4$ are each independently —O—; —CH$_2$—; —CH(CH$_3$)—; —CR$_5$R$_6$—; —NR$_5$—; —NR$_5$CH$_2$—; —NR$_5$C(O)—; —C(O)NR$_5$—; —NR$_5$C(O)NR$_5$—; —S(O)$_2$—; —NR$_5$S(O)$_2$—; or —C$_3$-C$_{10}$ cyclic group—;

$R_5$, $R_6$ and $R_7$ are each independently hydrogen; halogen; a $C_1$-$C_6$ alkyl group; a $C_3$-$C_{10}$ cyclic group; a $C_6$-$C_{10}$ aryl group; or —CH$_2$(Ph), $R_{10}$, $R_{11}$ and $R_{12}$ are each independently hydrogen; a $C_1$-$C_{13}$ alkyl group; a $C_6$-$C_{10}$ aryl group; a $C_3$-$C_{10}$ cyclic group; a $C_3$-$C_{10}$ heteroaryl group; a $C_3$-$C_{10}$ heterocyclic group; —C(O)—($C_1$-$C_{13}$ alkyl); —CH$_2$(Ph); —CH$_2$(Ph)R$_5$; a benzyl group; or —CH$_2$CH=CH$_2$, and N is 0, 1, 2, 3 or 4, wherein the $C_1$-$C_6$ alkyl group, $C_1$-$C_{13}$ alkyl group or $C_3$-$C_{10}$ cyclic group includes at least one substituent selected from the group consisting of hydrogen; a hydroxy group; a halogen group; a $C_1$-$C_{13}$ alkyl group; a $C_1$-$C_6$ alkoxy group; an amino group (—NR$_8$R$_9$); a nitro group (—N(O)$_2$); an amide group (—(C=O)NR$_8$R$_9$); a carboxylic group (—C(O)OH), a nitrile group (—CN), a urea group (—NR$_8$(C=O)NR$_9$—); a sulfonamide group (—NHS(O)$_2$—); a sulfide group (—S—); a sulfone group (—S(O)$_2$—); a phosphoryl group (—P(O)R$_8$R$_9$); a $C_6$-$C_{10}$ aryl group; a $C_3$-$C_{10}$ heteroaryl group; and a $C_3$-$C_{10}$ heterocyclic group, the $C_6$-$C_{10}$ aryl group, $C_3$-$C_{10}$ heteroaryl group or $C_3$-$C_{10}$ heterocyclic group includes at least one substituent selected from the group consisting of hydrogen; a hydroxy group; a halogen group; a carbonyl group (—(C=O)R$_8$R$_9$); a $C_1$-$C_3$ alkyl group substituted or unsubstituted with halogen or a $C_3$-$C_{10}$ heterocyclic group; a $C_1$-$C_3$ alkoxy group substituted or unsubstituted with halogen or a $C_3$-$C_{10}$ heterocyclic group; $C_6$-$C_{10}$ phenoxy; an amino group (—NR$_8$R$_9$); a nitro group (—N(O)$_2$); an amide group (—(C=O)NR$_8$R$_9$); a carboxylic group (—(C(O)OH), a nitrile group (—CN), a urea group (—NR$_8$(C=O)NR$_9$—); a sulfonamide group (—NHS(O)$_2$—); a sulfide group (—S—); a sulfone group (—S(O)$_2$—); a phosphoryl group (—P(O)R$_8$R$_9$); a $C_6$-$C_{10}$ aryl group; a $C_3$-$C_{10}$ heteroaryl group and a $C_3$-$C_{10}$ heterocyclic group, $R_8$ and $R_9$ described above include at least one selected from the group consisting of hydrogen; a $C_1$-$C_6$ alkyl group; a $C_1$-$C_6$ alkenyl group; a $C_1$-$C_6$ alkynyl group; a $C_6$-$C_{10}$ aryl group; a $C_3$-$C_{10}$ heteroaryl group; and a $C_3$-$C_{10}$ heterocyclic group, and the $C_3$-$C_{10}$ heteroaryl group and $C_3$-$C_{10}$ heterocyclic group include at least one heteroatom selected from the group consisting of N, O, and S.

In an embodiment of the present invention, in Formulae 1 to 6 above, $R_1$ is hydrogen; or a $C_1$-$C_{13}$ alkyl group; A is hydrogen; a $C_1$-$C_{13}$ alkyl group; a $C_6$-$C_{10}$ aryl group; a $C_3$-$C_{10}$ cyclic group; a $C_3$-$C_{10}$ heteroaryl group; a $C_3$-$C_{10}$ heterocyclic group; or —C(O)—($C_1$-$C_{13}$ alkyl); and Y is a $C_6$-$C_{10}$ aryl group.

In an embodiment of the present invention, the compound is the compound of Formula 1, and in Formula 1 above, $R_1$ is hydrogen; or a $C_1$-$C_{13}$ alkyl group; A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; Y is a $C_6$-$C_{10}$ aryl group; $L_1$, $L_3$ and $L_4$ are each independently selected from the group consisting of —NR$_5$C(O)—; and —C(O)NR$_5$—; and $L_2$ is

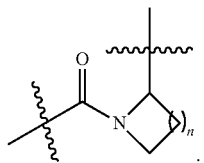

In an embodiment of the present invention, the compound is the compound of Formula 1, and in Formula 1 above, $R_1$ is hydrogen; or a $C_1$-$C_{13}$ alkyl group; A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; Y is a $C_6$-$C_{10}$ aryl group; $L_1$ and $L_2$ are each independently selected from the group consisting of —NR$_5$C(O)—, and —C(O)NR$_5$—; and $L_3$ is

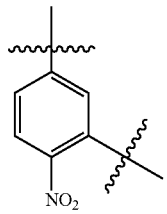

In an embodiment of the present invention, the compound is the compound of Formula 2, and in Formula 2 above, $R_1$ is hydrogen; or a $C_1$-$C_{13}$ alkyl group; A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; Y is a $C_6$-$C_{10}$ aryl group; and $L_1$ is selected from the group consisting of —NR$_5$C(O)—; and —C(O)NR$_5$—.

In an embodiment of the present invention, the compound is the compound of Formula 3, and in Formula 3 above, $R_1$ is hydrogen; or a $C_1$-$C_{13}$ alkyl group; A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; Y is a $C_6$-$C_{10}$ aryl group; $L_1$ is selected from the group consisting of —NR$_5$C(O)—; and —C(O)NR$_5$—; and $R_2$ is —CH$_2$—.

In an embodiment of the present invention, the compound is the compound of Formula 4, and in Formula 4 above, $R_1$ is hydrogen; or a $C_1$-$C_{13}$ alkyl group; A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; Y is a $C_6$-$C_1$ aryl group; $L_1$ and $L_2$ are each independently selected from the group consisting of —NR$_5$C(O)—; and —C(O)NR$_5$—; and $R_2$ and $R_3$ are —CH$_2$—.

In an embodiment of the present invention, the compound is the compound of Formula 5, and in Formula 5 above, $R_1$ is hydrogen; or a $C_1$-$C_{13}$ alkyl group; A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; and Y is a $C_6$-$C_{10}$ aryl group.

In an embodiment of the present invention, the compound is the compound of Formula 6, and in Formula 6 above, $R_1$ is hydrogen; or a $C_1$-$C_{13}$ alkyl group; A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; and Y is a $C_6$-$C_{10}$ aryl group.

In another aspect, the present invention provides a compound selected from a pyrimido[4,5-d]pyrimidin-2-one derivative compound represented by any one of the following Formulae 1 to 6, a pharmaceutically acceptable salt thereof, a hydrate thereof and a stereoisomer thereof, wherein the compound is selected from the group consisting of the following compound Nos. 1 to 57:

(Compound No. 1)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 2)
(R)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 3)
(R)—N-(1-(((S)-1-(dimethylamino)-4-methyl-1-oxopentan-2-yl)carbamoyl)cyclopropyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 4)
(S)—N-(1-(((S)-1-(dimethylamino)-4-methyl-1-oxopentan-2-yl)carbamoyl)cyclopropyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 5)
(R)—N-(2-(((S-1-(dimethylamino)-4-methyl-1-oxopentan-2-yl)amino)-2-oxoethyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 6)
(S)—N-(2-(((S-1-(dimethylamino)-4-methyl-1-oxopentan-2-yl)amino-2-oxoethyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 7)
(R)—N—((S)-3-methyl-1-oxo-1-(((R)-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-phenylalanyl)pyrrolidine-2-carboxamide;

(Compound No. 8)
(R)—N—((S)-3-methyl-1-oxo-1-(((R)-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 9)
(S)—N—((S)-3-methyl-1-oxo-1-(((R-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;
(Compound No. 10)
(R)—N-(1-(((R)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-D-valyl)pyrrolidine-2-carboxamide,
(Compound No. 11)
(S)—N—(((S-1-(dimethylamino)-4-methyl-1-oxopentan-2-yl)amino)-1-oxo-3-phenylpropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide,
(Compound No. 12)
(S)—N-(1-(((S)-1-(dimethylamino)-4-methyl-1-oxopentan-2-yl)carbamoyl)cyclobutyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide,
(Compound No. 13)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)piperidine-2-carboxamide,
(Compound No. 14)
(S)—N-(1-((2-(dimethylamino)-2-oxoethyl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;
(Compound No. 15)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)azetidine-2-carboxamide,
(Compound No. 16)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-isoleucyl)pyrrolidine-2-carboxamide,
(Compound No. 17)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-alanyl)pyrrolidine-2-carboxamide,
(Compound No. 18)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)glycyl)pyrrolidine-2-carboxamide,
(Compound No. 19)
(S)-1-((S)-2-cyclohexyl-2-((4-methyl-3-(1-methyl-7-((6-methylpyridin-3-yl)amino)-2-oxo-1,4-dihydropyrimido[4,5-d]pyrimidin-3(2H)-yl)benzamido)acetyl)-N-(1-(((S)-1-dimethylamino)-4-methyl-1-oxopentan-2-yl)amino)-2-methyl-1-oxopropan-2-yl]pyrrolidine-2-carboxamide;
(Compound No. 20)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-lucyl)pyrrolidine-2-carboxamide,
(Compound No. 21)
(S)—N-(1-(((S)-1-(dimethylamino)-4-methyl-1-oxopentan-2-yl)amino)-2-methyl-1-oxopropan-2-yl)-1-(S)-2-((4-methyl-3-(1-methyl-7-((6-methylpyridin-3-yl)amino)-2-oxo-1,4-dihydropyrimido[4,5-d]pyrimidin-3(2H)-yl)benzamido)pentanoyl)pyrrolidine-2-carboxamide;
(Compound No. 22)
(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide,
(Compound No. 23)
(R)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide,
(Compound No. 24)
(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-phenylalanyl)pyrrolidine-2-carboxamide,
(Compound No. 25)
(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-alanyl)pyrrolidine-2-carboxamide,
(Compound No. 26)
(S)-3-benzyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 27)
(S)-3-(3-fluorobenzyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 28)
(S)-3-(4-fluorobenzyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 29)
(S)—N-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-methylbenzyl)-2-oxo-5-phenyl-2,3-dihydro-1H-benzo[e][1,4]diazepine-8-carboxamide,
(Compound No. 30)
(S)-3-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 31)
(S)-1-benzyl-3-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 32)
(R)-3-((R)-sec-butyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 33)
(S)-1-benzyl-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 34)
(S)-3-benzyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide,
(Compound No. 35)
(R)-3-benzyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide,
(Compound No. 36)
(R)-3-benzyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 37)
(S)-3-isobutyl-1-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 38)
(S)-1-allyl-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 39)
(S)-1,3-diisobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 40)
(S)-3-isobutyl-1,5-dimethyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide,
(Compound No. 41)
(S)-1-benzyl-3-isobutyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide,
(Compound No. 42)
(S)-3-isobutyl-1-(2-methoxyethyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 43)
(S)-1-(2-(benzylamino)-2-oxoethyl)-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;
(Compound No. 44)
(S)-2-(5-(but-3-en-1-yl)-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide;
(Compound No. 45)
(S)-2-(5-(but-3-en-1-yl)-1-methyl-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide;
(Compound No. 46)
(S)-2-(1-benzyl-5-(but-3-en-1-yl)-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide,
(Compound No. 47)
(3S,4S)—N$^3$-benzyl-N$^4$-(4-chlorobenzyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)pyrrolidine-3,4-dicarboxamide;
(Compound No. 48)
(3S,4S)—N$^3$-(2-(1H-indol-3-yl)ethyl-N$^4$-(4-chlorobenzyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)pyrrolidine-3,4-dicarboxamide;
(Compound No. 49)
3-isobutoxy-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide,
(Compound No. 50)
3-(2-(1H-indol-3-yl)ethoxy)-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide,
(Compound No. 51)
3-(4-methoxyphenethoxy)-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide,
(Compound No. 52)
3-isobutoxy-N-(2-((4-methyl-3-(1-methyl-7-((6-methylpyridin-3-yl)amino)-2-oxo-1,4-dihydropyrimido[4,5-d]pyrimidin-3(2H)-yl)phenyl)amino)-2-oxoethyl)-4-nitrobenzamide,
(Compound No. 53)
(S)-3-isobutoxy-N-(1-((4-methyl-3-(1-methyl-7-((6-methylpyridin-3-yl)amino)-2-oxo-1,4-dihydropyrimido[4,5-d]pyrimidin-3(2H)-yl)phenyl)amino)-2-oxopropan-2-yl)-4-nitrobenzamide,
(Compound No. 54)
(S)-3-isobutoxy-N-(4-methyl-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopentan-2-yl)-4-nitrobenzamide;
(Compound No. 55)
(S)—N-3-(1H-indol-3-yl)-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopropan-2-yl)-3-isobutoxy-4-nitrobenzamide;
(Compound No. 56)
(S)-3-(4-methoxyphenethoxy)-N-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopropan-2-yl)-4-nitrobenzamide, and
(Compound No. 57) 2,2,2-trichloroethyl (3S,4S)-3-((4-chlorobenzyl)carbamoyl)-4-((4-methyl-3-(1-methyl-7-((6-methylpyridin-3-yl)amino)-2-oxo-1,4-dihydropyrimido[4,5-d]pyrimidin-3(2H)-yl)phenyl)carbamoyl)pyrrolidine-1-carboxylate.

In the definition of substituents in the present invention, the term "alkyl" means an aliphatic hydrocarbon radical. The alkyl may be "saturated alkyl" that does not contain an alkenyl or alkynyl moiety, or "unsaturated alkyl" that contains at least one alkenyl or alkynyl moiety. The term "alkenyl" means a group containing at least one carbon-carbon double bond, and the term "alkynyl" means a group containing at least one carbon-carbon triple bond. The alkyl may have a cyclic, branched or straight-chain form when used alone or in combination.

The term "aryl" means a carbocyclic aromatic monocyclic group containing 6 carbon atoms, which may be further fused singly or in combination with another radical with a second 5- or 6-membered carbocyclic group which may be aromatic, saturated or unsaturated. Examples of the aryl may include, but are not limited to, phenyl, indanyl, 1-naphthyl, 2-naphthyl, tetrahydronaphthyl and the like. The aryl may be linked to another group at an appropriate position on the aromatic ring.

The term "alkoxy" means an alkyl group linked to another group via an oxygen atom (i.e., —O-alkyl). The alkoxy group may or may not be substituted with at least one appropriate substituent. Examples of the alkoxy group include, but are not limited to, ($C_1$-$C_6$) alkoxy groups such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, -3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-butyl, —O-2-ethyl-1-butyl, —O-butyl, —O-isobutyl, —O-t-butyl, —O-pentyl, —O-isopentyl, —O-neopentyl and —O-hexyl.

The term "phenoxy" means a phenyl group (i.e., —O-aryl) linked to another group via an oxygen atom. The phenoxy group may or may not be substituted with at least one halogen, alkyl group, aryl group and heteroaryl group, but is not limited thereto.

The term "amino group" means an alkyl group linked to another group via a nitrogen atom (i.e., —NH— or —N-alkyl). The amino group may or may not be substituted with at least one appropriate substituent. Examples of the amino group include, but are not limited to, ($C_1$-$C_6$) amino groups, such as —NH-methyl, —NH-ethyl, —NH-propyl, —NH-isopropyl, —NH-2-methyl-1-propyl, —NH-2-methyl-2-propyl, —NH-2-methyl-1-butyl, —NH-3-methyl-1-butyl, —NH-2-methyl-3-butyl, —NH-2,2-dimethyl-1-propyl, —NH-2-methyl-1-pentyl, 3-N H-methyl-1-pentyl, —NH-4-methyl-1-pentyl, —NH-2-methyl-2-pentyl, —NH-3-methyl-2-pentyl, —NH-4-methyl-2-pentyl, —NH-2,2-dimethyl-1-butyl, —NH-3,3-dimethyl-butyl, —NH-2-ethyl-1-butyl, —NH-butyl, —NH-isobutyl, —NH-t-butyl, —NH-pentyl, —NH-isopentyl, —NH-neopentyl, —NH-hexyl, —N, N-dimethyl, —N-methyl-N-ethyl, —N-methyl-N-propyl, —N-methyl-isopropyl, —N-methyl-N-butyl, —N-methyl-N-isobutyl, —N-methyl-N-pentyl, —N-methyl-N-isopentyl, N-methyl-N-hexyl, N-methyl-N-isohexyl, —N, N-diethyl, —N-ethyl-N-propyl, —N-ethyl-N-isopropyl, —N-ethyl-N-butyl, —N-ethyl-N-isobutyl, —N-ethyl-N-pentyl, —N-ethyl-N-isopentyl, —N-ethyl-N-hexyl, —N-ethyl-N-isohexyl, —N, N-di propyl, —N-propyl-N-isopropyl, —N-propyl-N-butyl, —N-propyl-N-isobutyl, —N-propyl-N-pentyl, —N-propyl-N-isopentyl, —N-propyl-N-hexyl, —N-propyl-N-isohexyl, —N, N-dibutyl, —N-butyl-N-isobutyl, —N-butyl-N-pentyl, —N-butyl-N-isopentyl, —N-butyl-N-hexyl, —N-butyl-N-isohexyl, —N,N-dipentyl, —N-pentyl-N-hexyl, —N-pentyl-N-isohexyl, and —N, N-dihexyl.

The term "halogen atom" means fluorine (F), chlorine (Cl), bromine (Br) or iodine (I).

The term "heterocyclic group" means a heteroaromatic compound containing at least one heteroatom selected from the group consisting of N, O, and S, unless otherwise mentioned. Preferably, the heterocyclic group may include a pyrrolidine group, a furan group, a morpholine group, a piperazine group and a piperidine group, and more preferably a pyrrolidine group, a piperidine group, a piperazine group and a morpholine group, but is not limited thereto.

The term "heteroaryl group" means a heteroaromatic compound containing at least one heteroatom selected from the group consisting of N, O, and S, unless otherwise mentioned. Preferably, the heteroaryl group is a pyridine group, a pyrazine group, a pyrimidine group, a pyridazine group, a pyrazole group, an imidazole group, a triazole group, an indole group, an oxadiazole group, a thiadiazole group, a quinoline group, an isoquinoline group, an isoxazole group, an oxazole group, a thiazolyl group and a pyrrole group, but is not limited thereto.

Specific examples of compounds preferred as compounds according to the present invention are as follows:

(Compound No. 1)

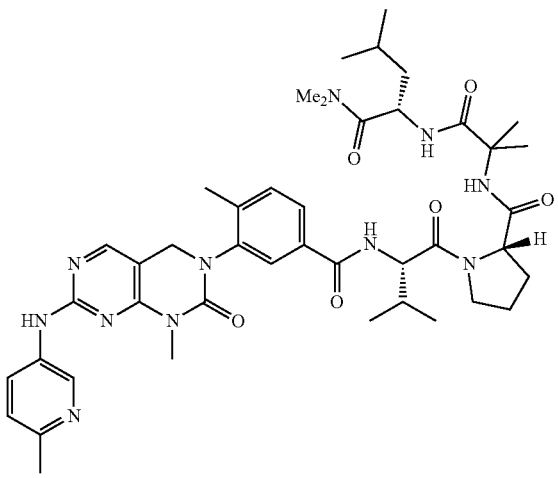

(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 2)

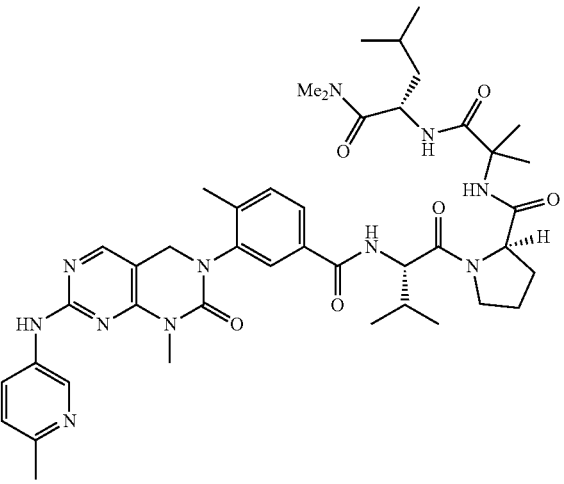

(R)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4- dihydropyrimido[4,5-d]pyrimidin-3(2H)-yl)benzoyl)-L-valyl)pyrrolidine-2-carboxamide, (R)—N-(1-(((S)-1-(dimethylamino)-4-methyl-1-oxopentan-2-yl)carbamoyl)cyclopropyl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-valyl)pyrrolidine-2-carboxamide, (Compound No. 3)

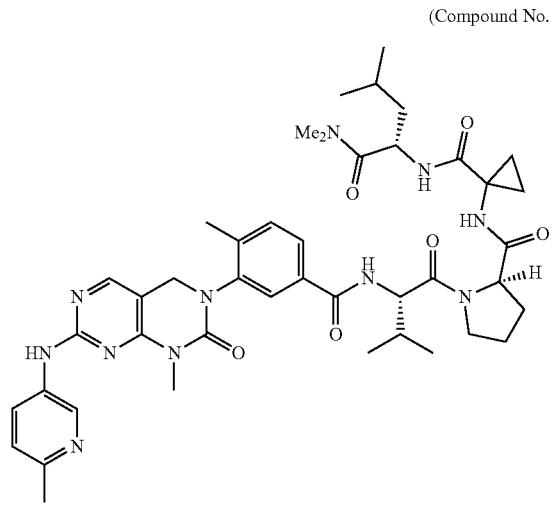

(Compound No. 4)

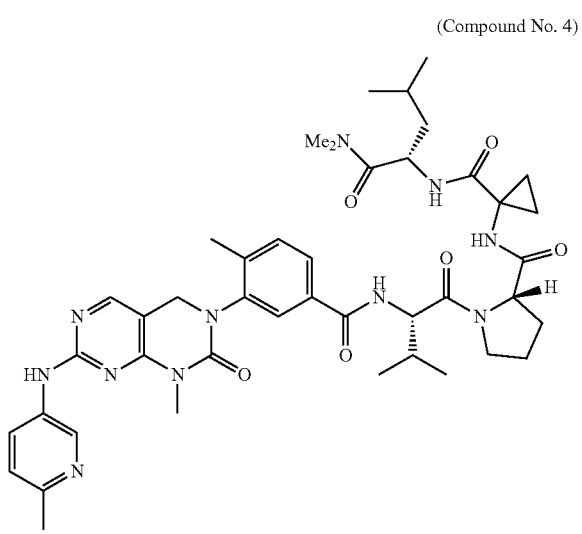 [SMILES: Cc1ccc(Nc2ncc3c(n2)N(C)C(=O)N(c2cc(C(=O)N[C@H](C(=O)N4CCC[C@H]4C(=O)NC4(C(=O)N[C@@H](CC(C)C)C(=O)N(C)C)CC4)C(C)C)ccc2C)C3)cn1]

(S)—N-(1-(((S)-1-(dimethylamino)-4-methyl-1-oxopentan-2-yl)carbamoyl)cyclopropyl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-valyl)pyrrolidine-2-carboxamide, (R)—N-(2-(((S-1-(dimethylamino)-4-methyl-1-oxopentan-2-yl)amino)-2-oxoethyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 5)

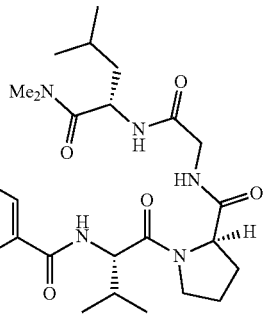

(Compound No. 6)

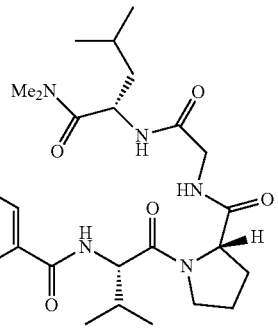

(S)—N-(2-(((S-1-(dimethylamino)-4-methyl-1-oxopentan-2-yl)amino-2-oxoethyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 7)

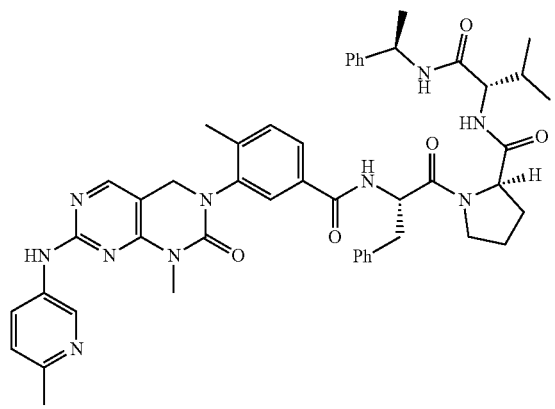

(R)—N—((S)-3-methyl-1-oxo-1-(((R)-1-phenylethyl)
amino)butan-2-yl)-1-((4-methyl-3-(1-methyl-7-((6-methylpyridin-3-yl)amino-2-oxo-1,4-dihydropyrimido[4,5-d]
pyrimidin-3(2H)-yl)benzoyl)-L-phenylalanyl)
pyrrolidine-2-carboxamide;

(S)—N—((S)-3-methyl-1-oxo-1-(((R-1-phenylethyl)amino)
butan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-valyl)pyrrolidine-2-carboxamide;

(Compound No. 8)

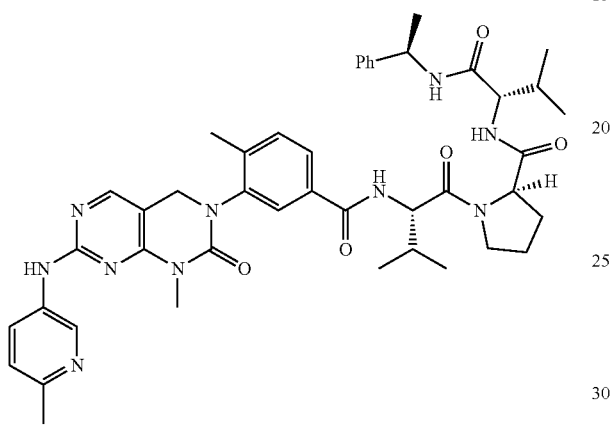

(Compound No. 10)

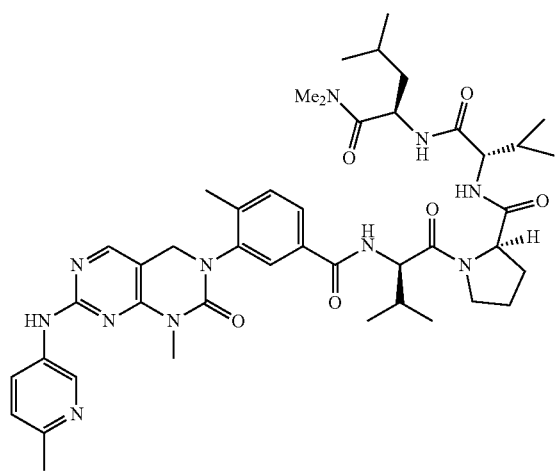

(R)—N—((S)-3-methyl-1-oxo-1-(((R)-1-phenylethyl)
amino)butan-2-yl)-1-((4-methyl-3-(1-methyl-7-((6-methylpyridin-3-yl)amino-2-oxo-1,4-dihydropyrimido[4,5-d]
pyrimidin-3(2H)-yl)benzoyl)-L-valyl)pyrrolidine-2-carboxamide;

(R)—N-(1-(((R-1-(dimethylamino)-4-methyl-1-oxopentan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-D-valyl)pyrrolidine-2-carboxamide, (Compound No. 9)

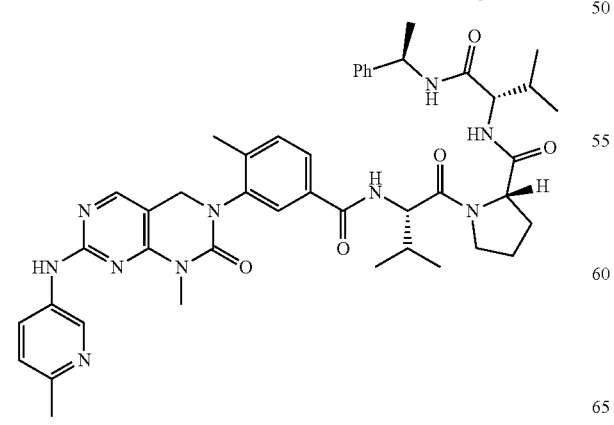

(Compound No. 11)

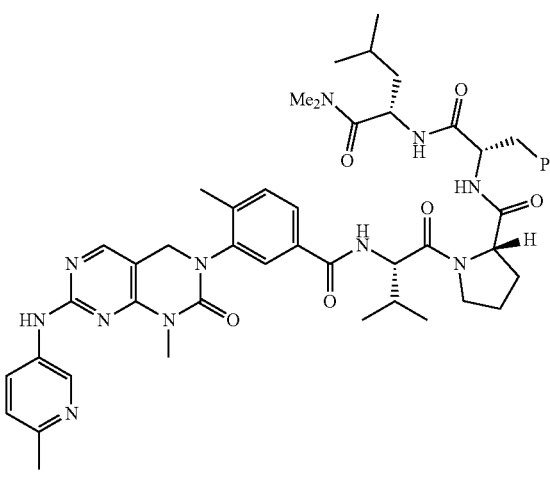

(S)—N—(((S-1-(dimethylamino)-4-methyl-1-oxopentan-2-yl)amino-1-oxo-3-phenylpropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-valyl)pyrrolidine-2-carboxamide, (S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)piperidine-2-carboxamide, (Compound No. 12)

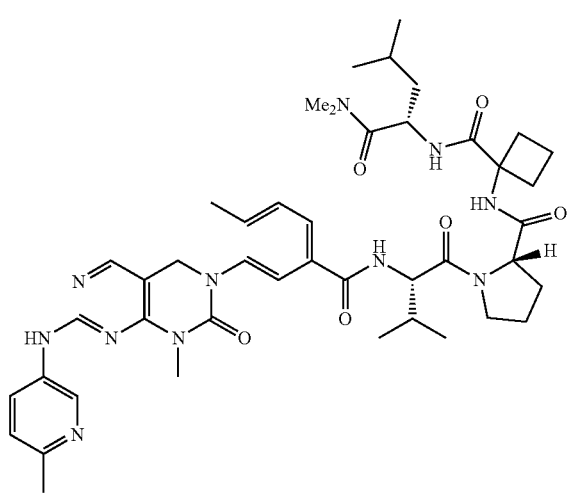

(Compound No. 14)

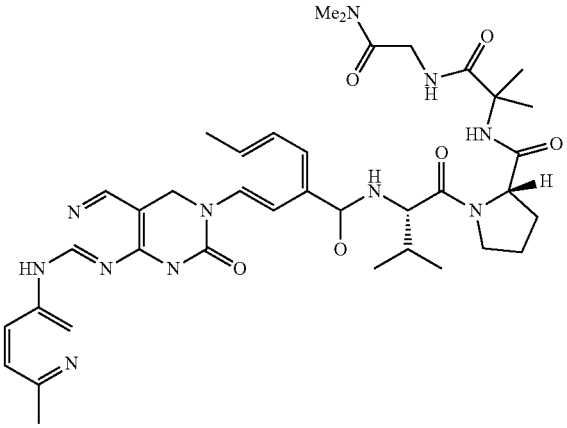

(S)—N-(1-(((S)-1-(dimethylamino)-4-methyl-1-oxopentan-2-yl)carbamoyl)cyclobutyl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-valyl)pyrrolidine-2-carboxamide, (S)—N-(1-((2-(dimethylamino)-2-oxoethyl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 15)

(Compound No. 13)

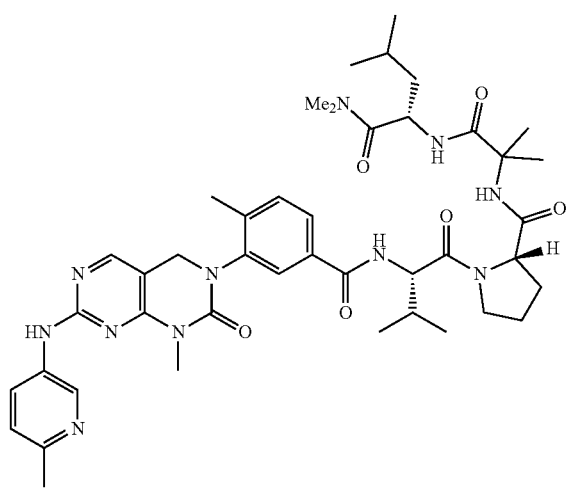

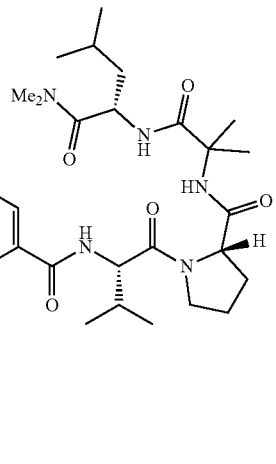

(S)—N-(1-(((S)-1-(dimethylamino)-4-methyl-1-oxopentan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-valyl)azetidine-2-carboxamide, (Compound No. 16)

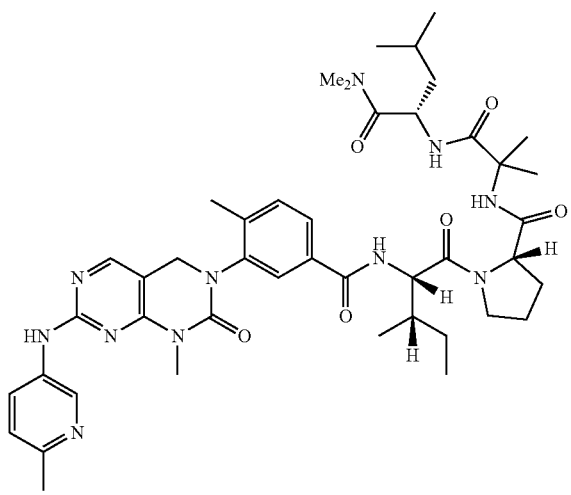

(S)—N-(1-(((S)-1-(dimethylamino)-4-methyl-1-oxopentan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-isoleucyl)pyrrolidine-2-carboxamide, (Compound No. 18)

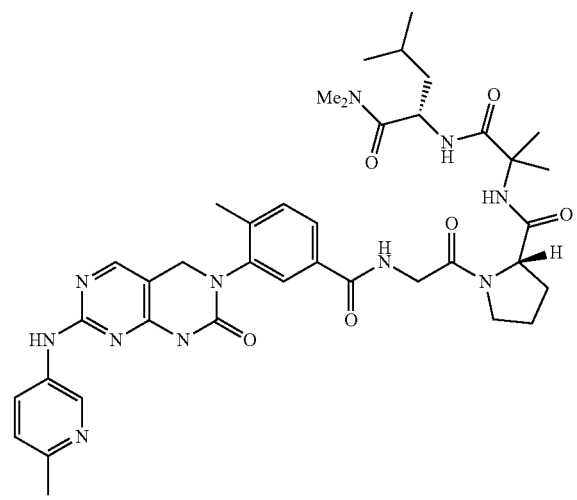

(S)—N-(1-(((S)-1-(dimethylamino)-4-methyl-1-oxopentan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)glycyl)pyrrolidine-2-carboxamide, (Compound No. 17)

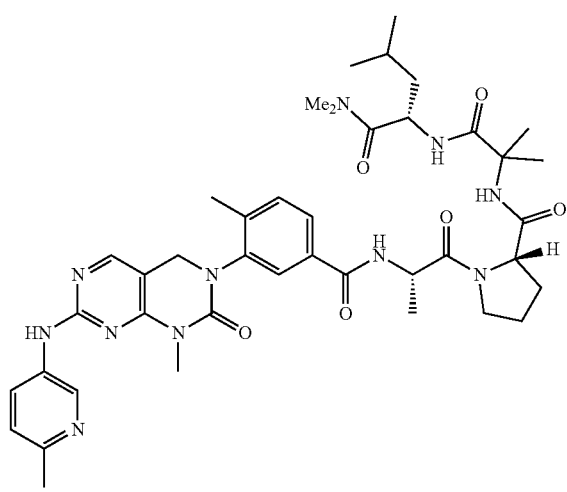

(S)—N-(1-(((S)-1-(dimethylamino)-4-methyl-1-oxopentan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-alanyl)pyrrolidine-2-carboxamide, (Compound No. 19)

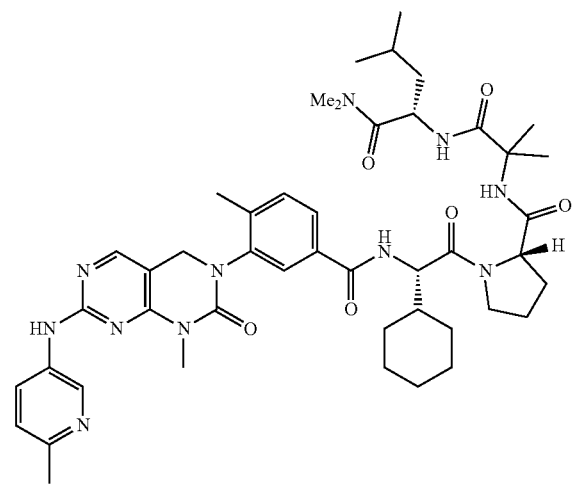

(S)-1-((S)-2-cyclohexyl-2-(4-methyl-3-(1-methyl-7-((6-methylpyridin-3-yl)amino)-2-oxo-1,4-dihydropyrimido[4,5-d]pyrimidin-3(2H)-yl)benzamido)acetyl)-N-(1-(((S)-1-dimethylamino)-4-methyl-1-oxopentan-2-yl)amino-2-methyl-1-oxopropan-2-yl]pyrrolidine-2-carboxamide;

(Compound No. 20)

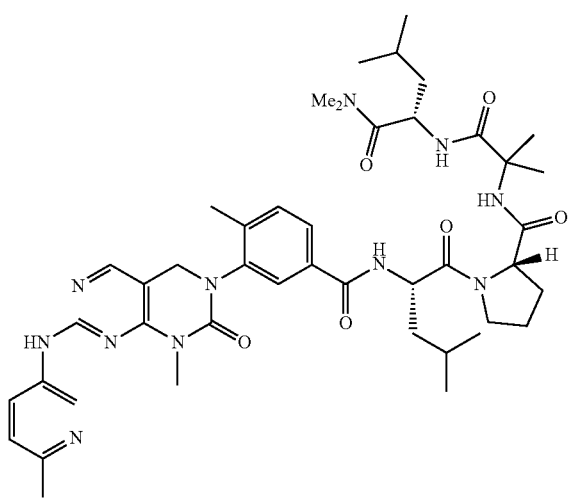

(S)—N-(1-(((S)-1-(dimethylamino)-4-methyl-1-oxopentan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-lucyl)pyrrolidine-2-carboxamide, (Compound No. 21)

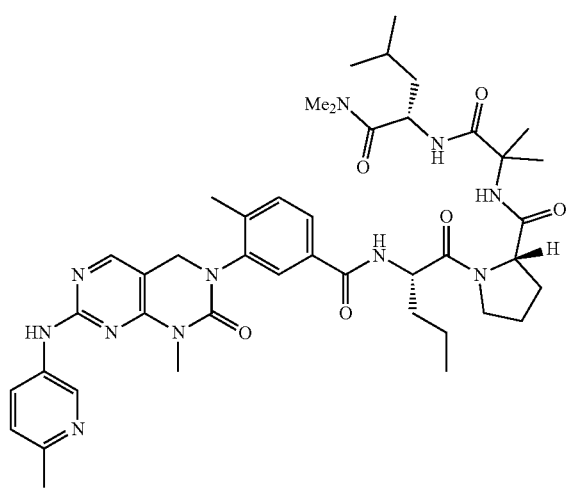

(S)—N-(1-(((S)-1-(dimethylamino)-4-methyl-1-oxopentan-2-yl)amino-2-methyl-1-oxopropan-2-yl)-1-((S)-2-(4-methyl-3-(1-methyl-7-((6-methylpyridin-3-yl)amino)-2-oxo-1,4-dihydropyrimido[4,5-d]pyrimidin-3(2H)-yl)benzamido)pentanoyl)pyrrolidine-2-carboxamide;

(Compound No. 22)

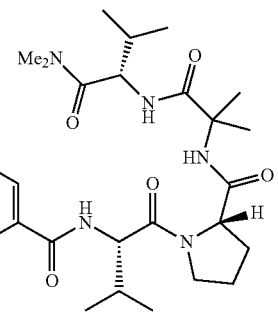

(S)—N-(1-(((S)-1-(dimethylamino)-3-methyl-1-oxobutan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-valyl)pyrrolidine-2-carboxamide, (Compound No. 23)

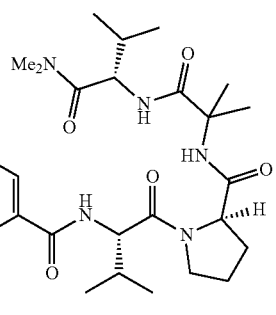

(R)—N-(1-(((S)-1-(dimethylamino)-3-methyl-1-oxobutan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-valyl)pyrrolidine-2-carboxamide, (Compound No. 24)

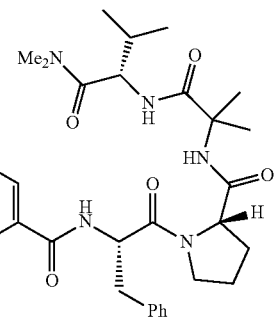

| 27 | 28 |
|---|---|
| (S)—N-(1-(((S)-1-(dimethylamino)-3-methyl-1-oxobutan-2-yl)amino-2-methyl-1-oxopropan-2-yl)-1-((4-methyl-3-(1-methyl-7-((6-methylpyridin-3-yl)amino-2-oxo-1,4-dihydropyrimido[4,5-d]pyrimidin-3(2H)-yl)benzoyl)-L-phenylalanyl)pyrrolidine-2-carboxamide, | (S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydro pyrimido[4,5-d]pyrimidin-3(2H)-yl)benzoyl)-L-alanyl)pyrrolidine-2-carboxamide; |

(Compound No. 25)

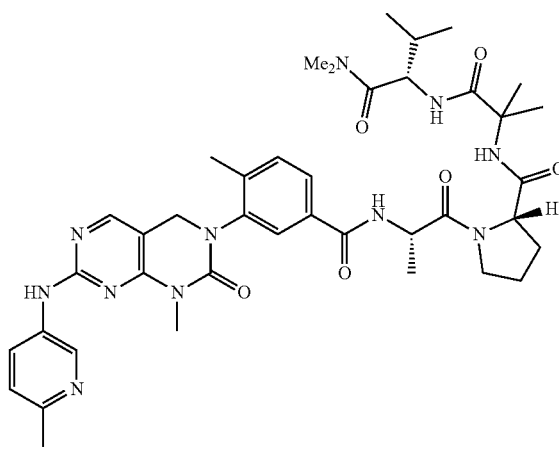

(Compound No. 26)

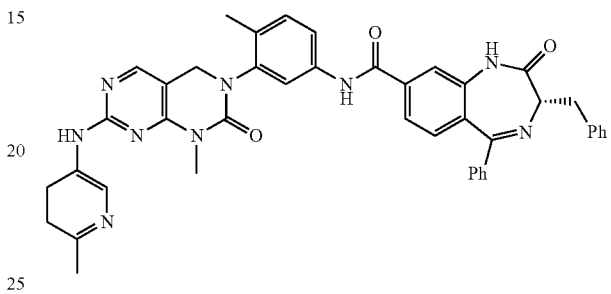

(S)-3-benzyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 27)

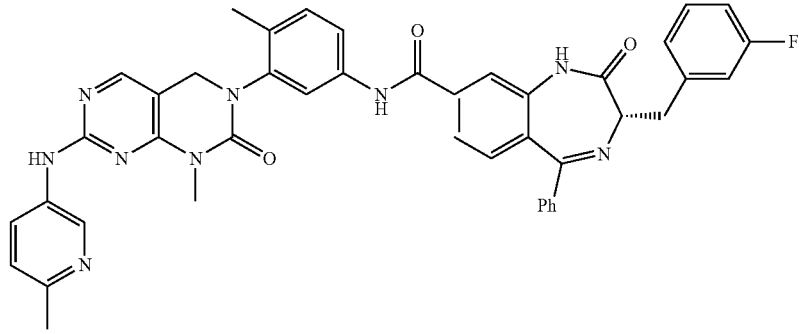

(S)-3-(3-fluorobenzyl)-N-(4-methyl-3-(1-methyl-7-((6-methylpyridin-3-yl)amino-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide:

(Compound No. 28)

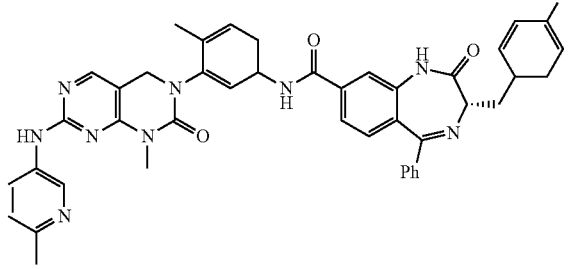

(S)-3-(4-fluorobenzyl)-N-(4-methyl-3-(1-methyl-7-((6-methylpyridin-3-yl)amino-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 29)

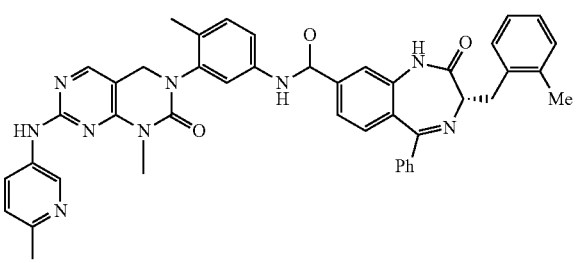

(S)—N-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-methylbenzyl)-2-oxo-5-phenyl-2,3-dihydro-1H-benzo[e][1,4]diazepine-8-carboxamide;

(Compound No. 30)

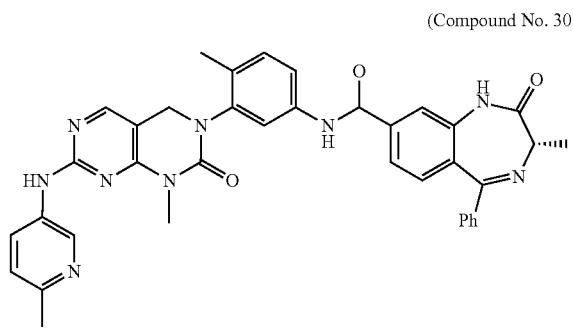

(S)-3-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 31)

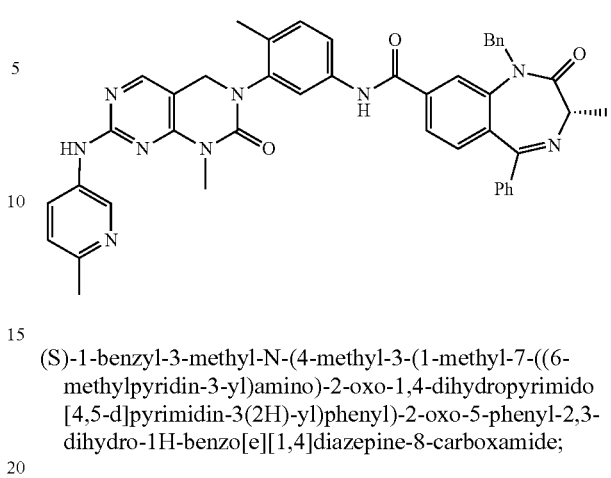

(S)-1-benzyl-3-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 32)

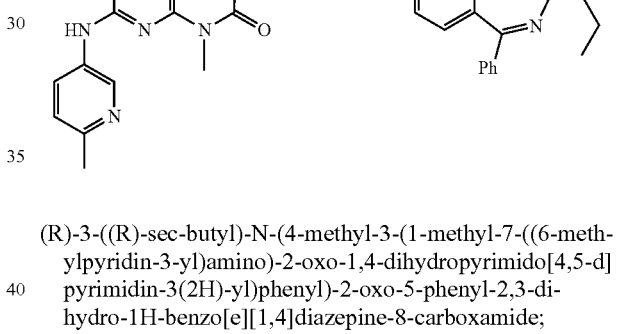

(R)-3-((R)-sec-butyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 33)

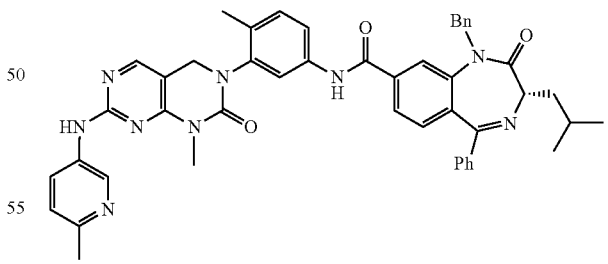

(S)-1-benzyl-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(S)-3-benzyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide;

(Compound No. 34)

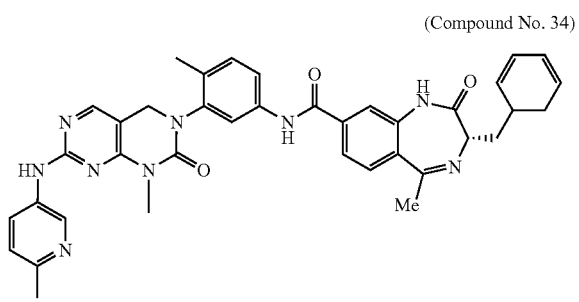 [SMILES: CC1=N[C@@H](CC2C=CC=CC2)C(=O)Nc2cc(C(=O)Nc3ccc(C)c(N4Cc5cnc(Nc6ccc(C)nc6)nc5N(C)C4=O)c3)ccc21]

(R)-3-benzyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide;

(Compound No. 35)

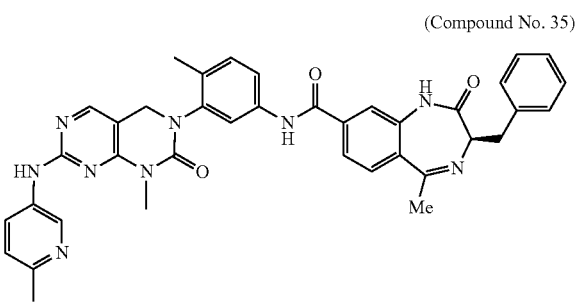 [SMILES: CC1=N[C@H](Cc2ccccc2)C(=O)Nc2cc(C(=O)Nc3ccc(C)c(N4Cc5cnc(Nc6ccc(C)nc6)nc5N(C)C4=O)c3)ccc21]

(R)-3-benzyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 36)

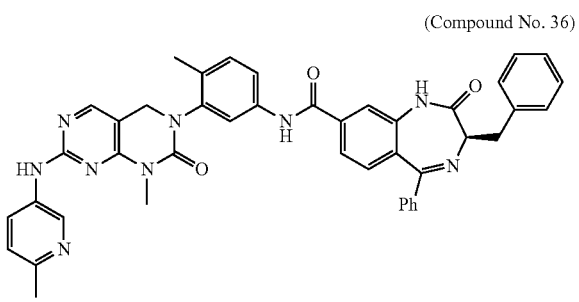 [SMILES: Cc1ccc(Nc2ncc3c(n2)N(C)C(=O)N(c2cc(NC(=O)c4ccc5c(c4)NC(=O)[C@@H](Cc4ccccc4)N=C5c4ccccc4)ccc2C)C3)cn1]

(Compound No. 37)

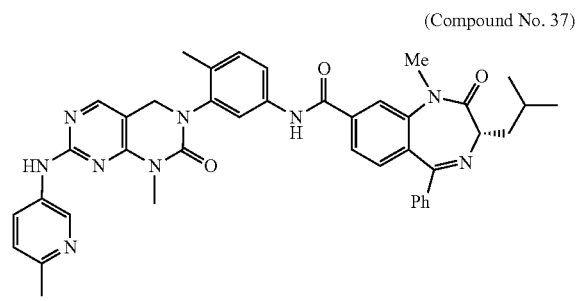 [SMILES: Cc1ccc(Nc2ncc3c(n2)N(C)C(=O)N(c2cc(NC(=O)c4ccc5c(c4)N(C)C(=O)[C@H](CC(C)C)N=C5c4ccccc4)ccc2C)C3)cn1]

(S)-3-isobutyl-1-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 38)

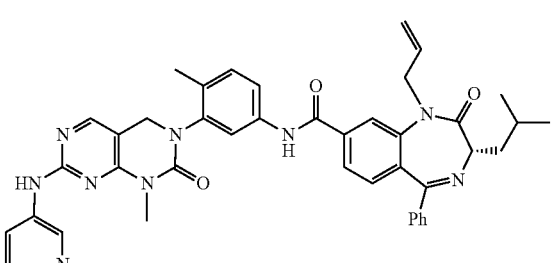

(S)-1-allyl-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 39)

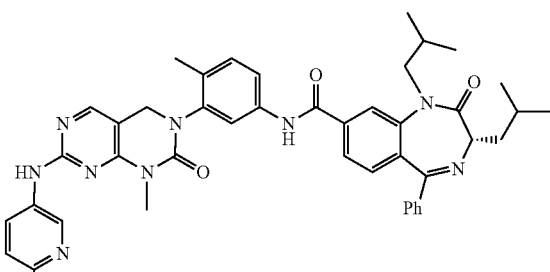

(S)-1,3-diisobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 40)

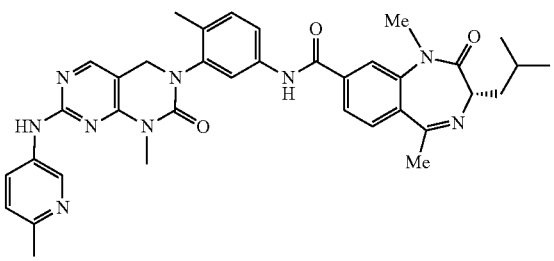

(S)-3-isobutyl-1,5-dimethyl-N-(4-methyl-3-(1-methyl-7-(((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide;

(Compound No. 41)

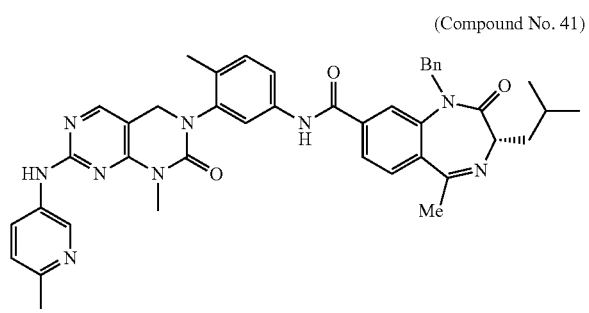 [SMILES: CC1=N[C@@H](CC(C)C)C(=O)N(Cc2ccccc2)c2cc(C(=O)Nc3ccc(C)c(N4Cc5cnc(Nc6ccc(C)nc6)nc5N(C)C4=O)c3)ccc21]

(S)-1-benzyl-3-isobutyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide;

(Compound No. 42)

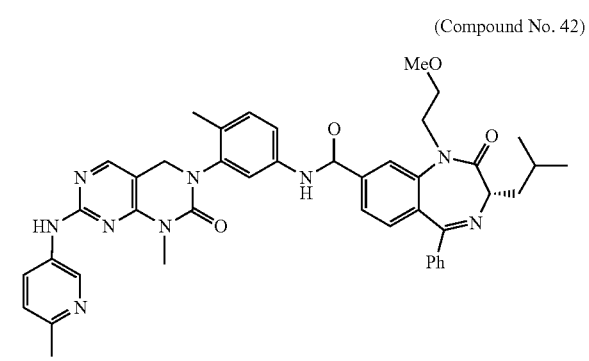 [SMILES: COCCN1C(=O)[C@H](CC(C)C)N=C(c2ccccc2)c2ccc(C(O)Nc3ccc(C)c(N4Cc5cnc(Nc6ccc(C)nc6)nc5N(C)C4=O)c3)cc21]

(S)-3-isobutyl-1-(2-methoxyethyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 43)

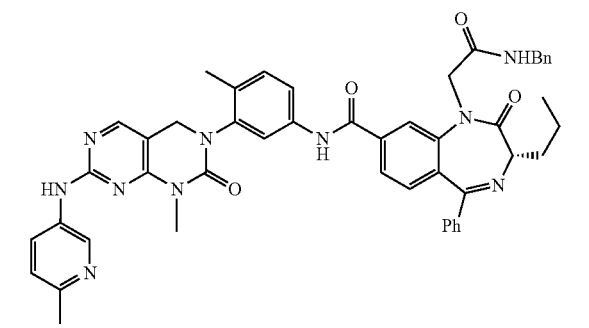

(S)-1-(2-(benzylamino)-2-oxoethyl)-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide;

(Compound No. 44)

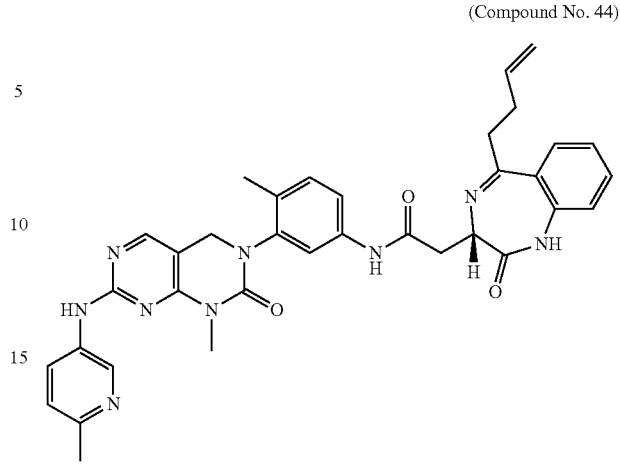

(S)-2-(5-(but-3-en-1-yl)-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide;

(Compound No. 45)

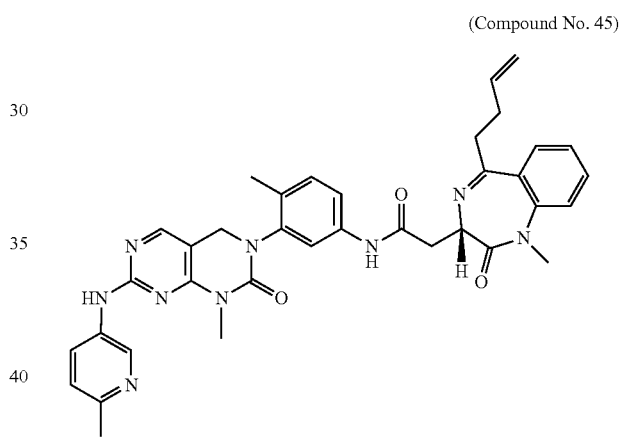

(S)-2-(5-(but-3-en-1-yl)-1-methyl-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide;

(Compound No. 46)

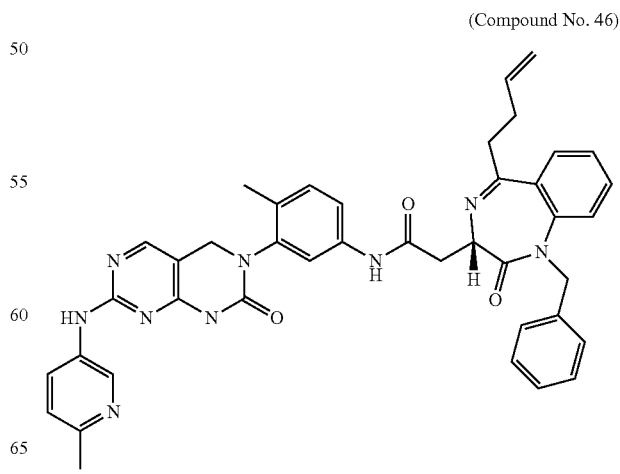

(S)-2-(1-benzyl-5-(but-3-en-1-yl)-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide;

(Compound No. 47)

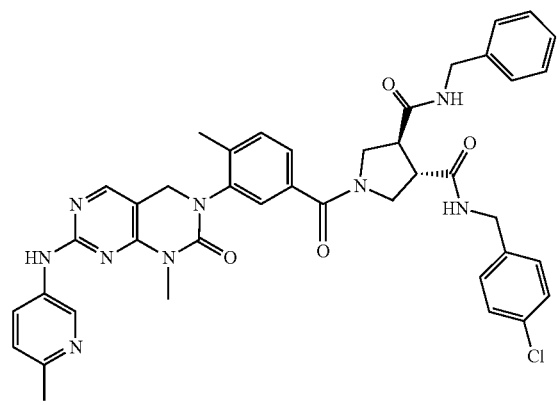

(3S,4S)—N³-benzyl-N4-(4-chlorobenzyl)-1-(4-methyl-3-(1-methyl-7-((6-methylpyridin-3-yl)amino)-2-oxo-1,4-dihydropyrimido[4,5-d]pyrimidin-3(2H)-yl)benzoyl)pyrrolidine-3,4-dicarboxamide;

(Compound No. 48)

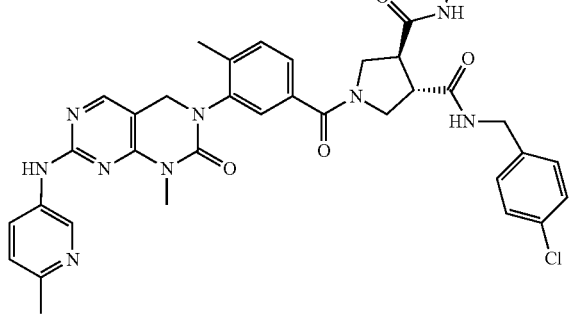

(3S,4S)—N³-(2-(1H-indol-3-yl)ethyl)-N⁴-(4-chlorobenzyl)-1-(4-methyl-3-(1-methyl-7-((6-methylpyridin-3-yl)amino)-2-oxo-1,4-dihydropyrimido[4,5-d]pyrimidin-3(2H)-yl)benzoyl)pyrrolidine-3,4-dicarboxamide;

(Compound No. 49)

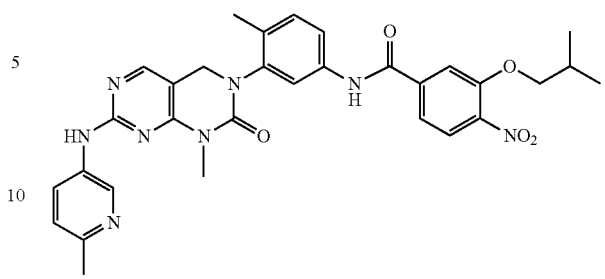

3-isobutoxy-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide;

(Compound No. 50)

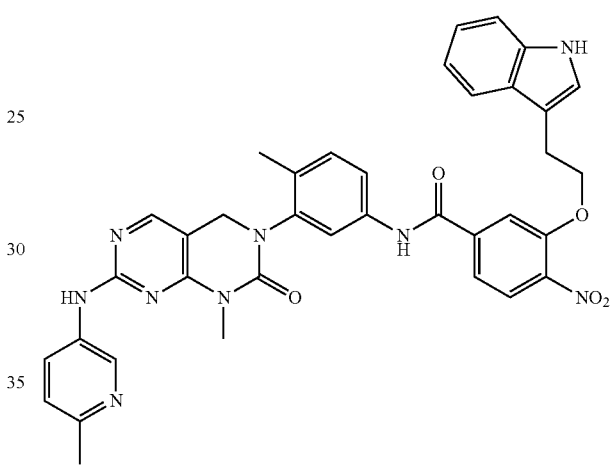

3-(2-(1H-indol-3-yl)ethoxy)-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide;

(Compound No. 51)

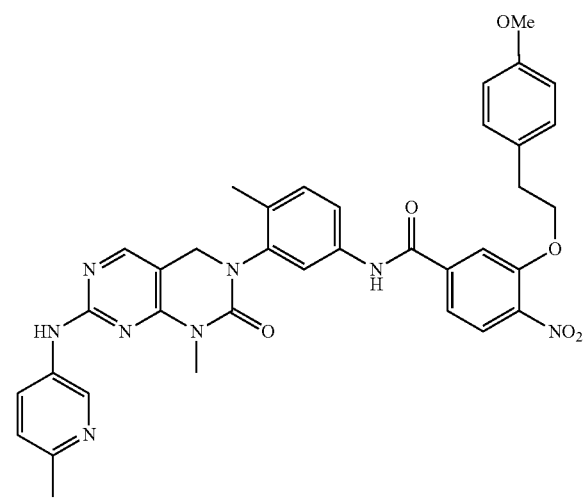

3-(4-methoxyphenethoxy)-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide;

(Compound No. 52)

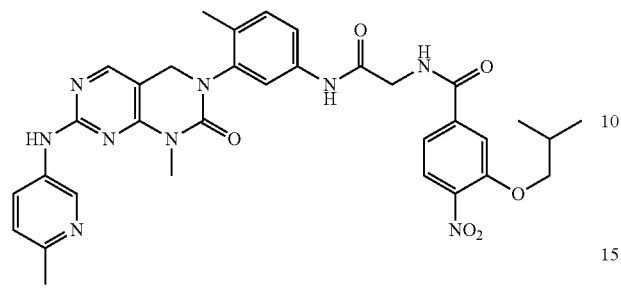

3-isobutoxy-N-(2-((4-methyl-3-(1-methyl-7-((6-methylpyridin-3-yl)amino)-2-oxo-1,4-dihydropyrimido[4,5-d]pyrimidin-3(2H)-yl)phenyl)amino)-2-oxoethyl)-4-nitrobenzamide;

(Compound No. 53)

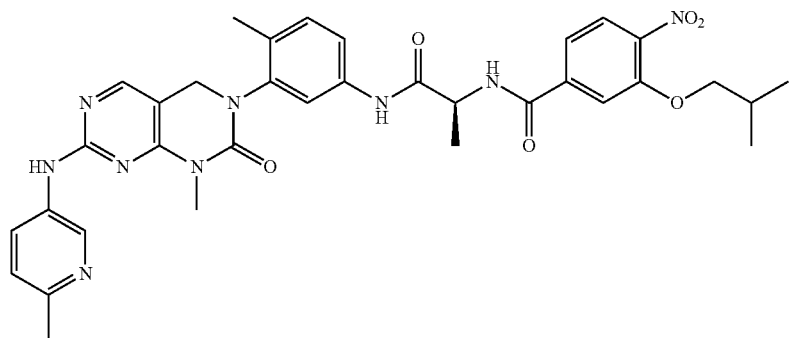

(S)-3-isobutoxy-N-(1-((4-methyl-3-(1-methyl-7-((6-methylpyridin-3-yl)amino)-2-oxo-1,4-dihydropyrimido[4,5-d]pyrimidin-3(2H)-yl)phenyl)amino)-2-oxopropan-2-yl)-4-nitrobenzamide;

(Compound No. 54)

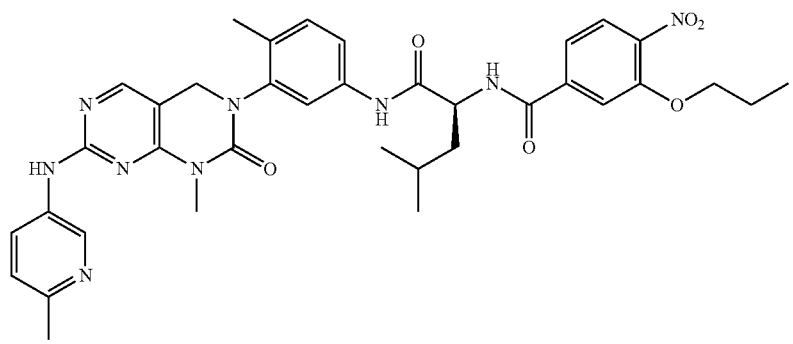

(S)-3-isobutoxy-N-(4-methyl-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopentan-2-yl)-4-nitrobenzamide;

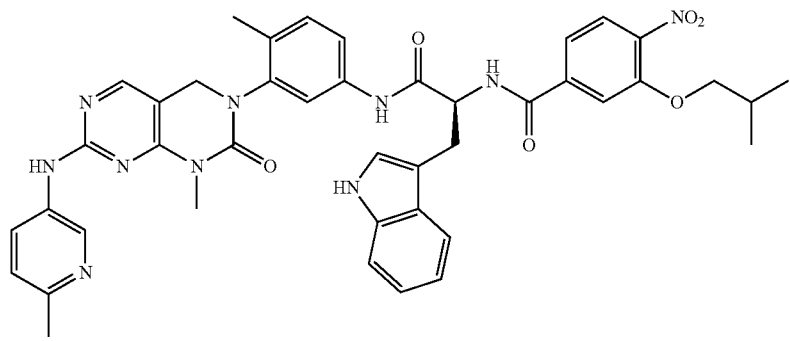

(Compound No. 55)

(S)—N-3-(1H-indol-3-yl)-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopropan-2-yl)-3-isobutoxy-4-nitrobenzamide;

The compound according to the present invention may be used in the form of a pharmaceutically acceptable salt derived from an inorganic or organic acid, and preferred pharmaceutically acceptable salts may include at least one

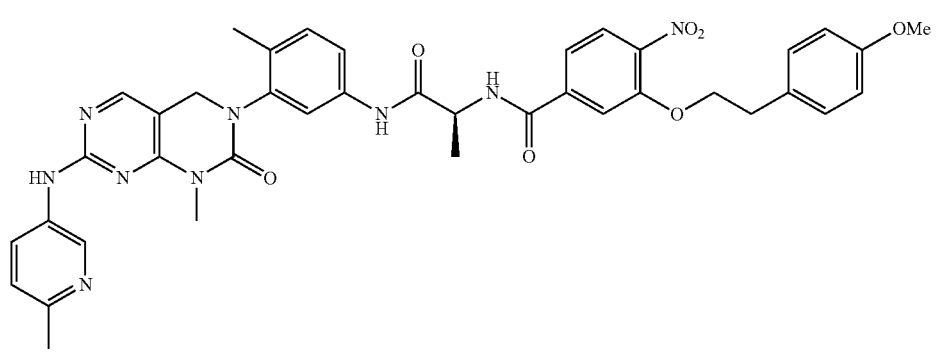

(Compound No. 56)

(S)-3-(4-methoxyphenethoxy)-N-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopropan-2-yl)-4-nitrobenzamide, and

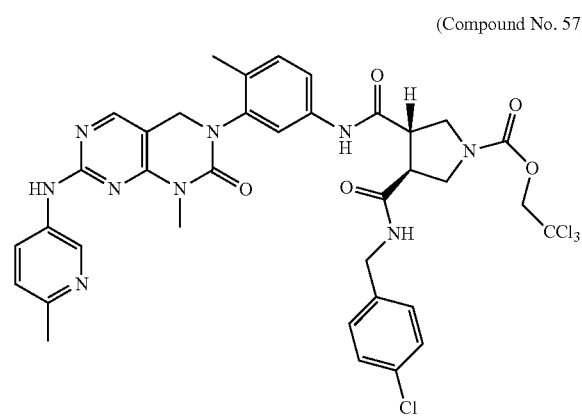

(Compound No. 57)

2,2,2-trichloroethyl (3S,4S)-3-((4-chlorobenzyl)carbamoyl)-4-((4-methyl-3-(1-methyl-7-((6-methylpyridin-3-yl)amino)-2-oxo-1,4-dihydropyrimido[4,5-d]pyrimidin-3(2H)-yl)phenyl)carbamoyl)pyrrolidine-1-carboxylate selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The compound represented by any one of Formulae 1 to 6 according to the present invention or a pharmaceutically acceptable salt thereof may include a hydrate and a solvate. The hydrate may be formed by bonding the compound represented by any one of Formulas 1 to 6 with a water molecule.

In another aspect, the present invention provides a pharmaceutical composition for preventing, alleviating or treating cancer containing, as an active ingredient, a compound selected from a compound represented by any one of Formulas 1 to 6 according to the present invention, a pharmaceutically acceptable salt thereof, a hydrate thereof and a stereoisomer thereof.

The pharmaceutical composition according to the present invention has excellent ability to inhibit the activity of protein kinase. The protein kinase may specifically include ABL1, ABL2/ARG, ARAF, BLK, BMX/ETK, BRAF, c-Src, CSK, DDR1, DDR2, EPHA2, EPHA4, ERBB4/HER2, ERBB4/HER4, EPHB1, FGR, FRK/PTK5, FYN, FGFR1, FMS, HCK, LCK, LIMK1, LYN, LYN B, MEK5, MLK1/MAP3K9, MLK3/MAP3K11, P38a/MAPK14, PDGFRa, PDGFRb, PEAK1, RAF1, YES/YES1, ARK5/NUAK1, Aurora C, BMPR2, BRSK2, BTK, c-Kit, CAMK1b, CAMK1d, CAMKK2, CK1d, CK2a, CK2a2, CLK1, CLK3, CTK/MATK, DAPK1, DYRK1/DYRK1A, DYRK1B, DYRK3, EGRF, EPHA2, EPHA3, EPHA4, EPHA5, EPHA8, EPHB1, EPHA3, EPHA5, EPHA8, EPHB2, EPHB4, ERBB2/HER2, ERK1, ERN1/IRE1, FLT4NEGFR3, GRK4, HIPK3, IKKa/CHUK, IRAK1, KDR/VEGFR2, KHS/MAP4K5, MAPKAPK5/PRAK, MASTL, MEK2, MEKK3, MKK6, MLK1/MAP3K9, MLK2/MAP3K10, MLK3/MAP3K11, MSK1/RPS6KA5, MSK2/RPS6KA4, MSSK1/STK23, MST4, MUSK, NEK11, NEK8, p38b/MAPK11, PAK5, PKCd, PKCeta, PKCG, PKMYT1, PKN3/PRK3, PLK3, PYK2, RET, RIPK4, RON/MST1R, ROS/ROS1, SIK1, ZAK/MLTK, WNK3, WNK2, TRKC, STK32B/YANK2, SNRK, SLK/STK2, SIK3, RSK1, ROCK1, PKG2/PRKG2, MRCKa/CDC42BPA, LIMK2, JAK2, JAK1, ITK, IRAK1, GSK3a, GCK/MAP4K2, FGFR2, FGFR1, FES/FPS, c-MET, c-Kit, ARAF, ALK6/BMPR1B, ALK1/ACVRL1, AKT3, or the like.

Therefore, the pharmaceutical composition of the present invention may be used for treating, preventing and alleviating cancer-related diseases caused by abnormal cell growth. Examples of the cancer-related diseases that can be prevented, treated or alleviated through treatment with the pharmaceutical composition of the present invention include stomach cancer, lung cancer, liver cancer, colorectal cancer, small intestine cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, kidney cancer, sarcoma, prostate cancer, urethral cancer, bladder cancer, blood cancer (including leukemia, multiple myeloma, myelodysplastic syndrome), lymphoma (including Hodgkin's disease, non-Hodgkin's lymphoma), psoriasis, fibroadenomas and the like.

In particular, the pharmaceutical composition of the present invention may be applied as a therapeutic agent for cancer-related diseases, inflammatory diseases and immune diseases caused by overexpression and mutation of LCK, DDR1, FGR, BMX, ABL2, BLX, BLK, LYN, DDR2, RAF1, c-src, CS and HCK kinases.

Preferably, the cancer is mediated and caused by protein kinase. Preferably, the protein kinase may include one or more selected from LCK, c-Src, p38a/MAPK14, ABL1, DDR1 and FGR. More preferably, the protein kinase may be LCK.

In another aspect, the present invention provides a pharmaceutical composition for preventing, alleviating or treating cancer containing any one of the compounds as an active ingredient.

In another aspect, the present invention provides a pharmaceutical composition for preventing, alleviating or treating cancer, wherein the cancer is caused by an LCK mutation.

In another aspect, the present invention provides a pharmaceutical composition acting as a therapeutic agent for cancer-related diseases, inflammatory diseases and immune diseases, wherein the pharmaceutical composition is applied to a patient overexpressing LCK.

In another embodiment of the present invention, the cancer includes one or more selected from the group consisting of colorectal cancer, thymic cancer, brain cancer, prostate cancer, leukemia, lung cancer, breast cancer, thyroid cancer, bladder cancer, stomach cancer, and blood cancer.

The pharmaceutical composition may be applied to experimental animals such as mice, rabbits, rats, guinea pigs or hamsters, or primates including humans, but is not limited thereto. Preferably, the pharmaceutical composition may be applied to primates including humans, more preferably humans.

As used herein, the term "treatment" includes alleviating or ameliorating symptoms, reducing the extent of a disease, delaying or alleviating disease progression, ameliorating, alleviating or stabilizing a disease condition, partial or full recovery, prolonging survival, and other beneficial treatment results.

In addition, as used herein, the treatment of cancer means treatment of all cancer cells, and the cancer includes angiogenesis of endothelial cells and mitosis thereof (solid tumor, tumor metastasis and benign tumor). For example, the cancer includes, but is not limited to, breast cancer, ovarian cancer, cervical cancer, prostate cancer, testicular cancer, genitourinary cancer, esophageal cancer, laryngeal cancer, glioblastoma, stomach cancer, skin cancer, keratoacanthomas, lung cancer, squamous cell carcinoma, large cell carcinoma, small cell carcinoma, lung adenocarcinoma, bone cancer, colon cancer, adenoma, pancreatic cancer, adenocarcinoma, carcinogenic cancer, follicular carcinoma, undifferentiated cancer, papillary cancer, normal hematoma, melanoma, sarcoma, bladder cancer, liver cancer, bile duct cancer, kidney cancer, myeloid disease, lymphoid disease, Hodgkin's disease, hair cell cancer, oral cavity cancer, pharyngeal (oral) cancer, lip cancer, tongue cancer, small intestine cancer, colorectal cancer, rectal cancer, brain cancer, central nervous system cancer, leukemia, hemangioma, trachoma and purulent sarcoma.

The content of the active ingredient, namely, the compound represented by any one of Formulae 1 to 6 above, the pharmaceutically acceptable salt thereof, the hydrate thereof and the stereoisomer thereof is appropriately adjusted by selection by those skilled in the art according to the use mode and use method of the pharmaceutical composition of the present invention.

For example, the pharmaceutical composition is present in an amount of 0.1 to 10% by weight, more preferably 0.5 to 5% by weight, based on the total weight of the compound selected from the compound represented by any one of Formulae 1 to 6, the pharmaceutically acceptable salt thereof, the hydrate thereof and the stereoisomer thereof.

The compound selected from the compound represented by any one of Formulae 1 to 6, the pharmaceutically acceptable salt thereof, the hydrate thereof and the stereoisomer thereof may be present in the pharmaceutical composition alone or in combination with a pharmacologically acceptable carrier, excipient, diluent or adjuvant.

Examples of the pharmaceutically acceptable carrier, excipient and diluent include, but are not limited thereto, one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, dextrin, calcium carbonate, propylene glycol, liquid paraffin, and physiological saline, and any common carrier, excipient, or diluent may be used. In addition, the pharmaceutical composition may further include an ordinary filler, extender, binder, disintegrating agent, anticoagulant, lubricant, wetting agent, pH-adjusting agent, nutrient, vitamin, electrolyte, alginic acid and salt thereof, pectic acid and salt thereof, protective colloid, glycerin, fragrance, emulsifier, preservative or the like.

The compound selected from the compound represented by any one of Formulae 1 to 6 or the pharmaceutically acceptable salt thereof may be administered in combination with another anticancer agent for treating cancer or tumors to improve an effect of treatment with the anticancer agent.

Specifically, the pharmaceutical composition may further include at least one other anti-cancer agent or therapeutic agent known to be effective for treating or preventing cancer in addition to the active ingredient, and thus may be used as a simultaneously or separately applied combination therapy. Other anti-cancer agents or therapeutic agents that may be applied to combination therapy may include, for example, at least one compound selected from the group consisting of Gleevec® (imatinib), Sutent® (sunitinib), Herceptin® (trastuzumab), Velcade® (bortezomib), dexamethasone, Nexavar® (sorafenib), aromatase inhibitors, or kinase inhibitors, but are not limited thereto.

The pharmaceutical composition may be administered orally or parenterally, and, for example, may be administered through various routes including oral, transdermal, subcutaneous, intravenous or intramuscular routes. In addition, the formulation of the composition may vary depending on the method of use, and may be formulated using methods well known in the art so as to provide rapid, sustained or delayed release of the active ingredient after administration to a mammal. In general, solid formulations for oral administration include tablets, troches, soft or hard capsules, pills, powders, granules and the like. These formulations, for example, can be prepared by mixing at least one excipient such as starch, calcium carbonate, sucrose, lactose, gelatin or the like. In addition, lubricants such as magnesium stearate and talc may be also used in addition to simple excipients. Liquid formulations for oral administration include suspensions, liquids and solutions, emulsions, syrups and the like. In addition to water and liquid paraffin, which are commonly used simple diluents, various excipients such as wetting agents, sweeteners, fragrances and preservatives may be included. Formulations for parenteral administration include creams, lotions, ointments, plasters, liquids and solutions, aerosols, fluid extracts, elixirs, infusions, sachets, patches, injections and the like. Injection formulations may be preferably in the form of an isotonic aqueous solution or suspension.

The pharmaceutical composition may further include an adjuvant such as a sterilant, a preservative, a stabilizer, a hydrating agent or an emulsifying accelerator, a salt and/or a buffer for controlling osmotic pressure, and other therapeutically useful substances. Alternatively, the pharmaceutical composition may be formulated according to an ordinary mixing, granulation or coating method or using a suitable method known in the art.

In addition, the dosage of the pharmaceutical composition may be determined in consideration of the administration method, the age, gender, severity of disease and condition of the patient, the rate of absorption of the active ingredient in the body, and the inactivation rate of the active ingredient and drugs used in combination therewith, and the pharmaceutical composition may be administered once or multiple times in a portionwise manner. The active ingredient of the pharmaceutical composition is preferably orally or parenterally administered to a mammal including a human in an amount of 0.001 to 100 mg/kg body weight, preferably 0.01 to 35 mg/kg body weight, on a daily basis, once or multiple times in a portionwise manner per day.

In another aspect, the present invention provides a method of treating cancer including administering a therapeutically effective amount of the compound represented by any one of Formulae 1 to 6, a pharmaceutically acceptable salt thereof, a hydrate thereof or a stereoisomer thereof.

Preferably, the treatment method may further include identifying a patient in need of prevention or treatment of cancer before the administration.

As used herein, the term "therapeutically effective amount" means an amount of an active ingredient that is effective for the prevention or treatment of cancer in a mammal, and the therapeutically effective amount may be controlled by a variety of factors such as the type of disease, the severity of the disease, the type and content of the active ingredient and other ingredients contained in the composition, the type of formulation, the age, weight, general state of health, gender and diet of the patient, the time of administration, route of administration, clearance rate of the composition in blood, duration of treatment, and drugs used simultaneously therewith. However, preferably, as described above, the compound may be administered in an amount of 0.001 to 100 mg/kg body weight, preferably 0.01 to 35 mg/kg body weight, on a daily basis, once or multiple times in a portionwise manner per day, via an oral or parenteral route.

In another aspect, the present invention provides a method of preparing the compound represented by any one of Formulae 1 to 6, a pharmaceutically acceptable salt thereof or a hydrate thereof.

Hereinafter, the present invention will be described in more detail with reference to Preparation Examples, Examples and Experimental Examples. However, the following Preparation Examples, Examples and Experimental Examples are provided only for better understanding of the present invention, and should not be construed as limiting the scope of the present invention.

Preparation Example 1

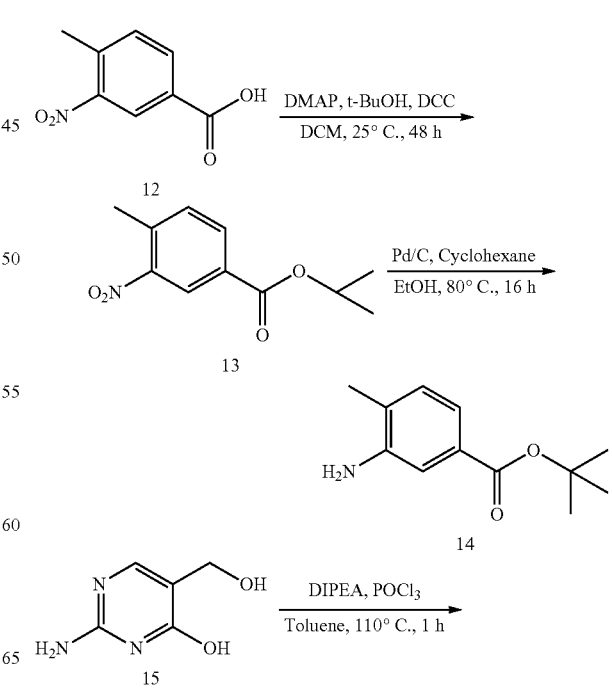

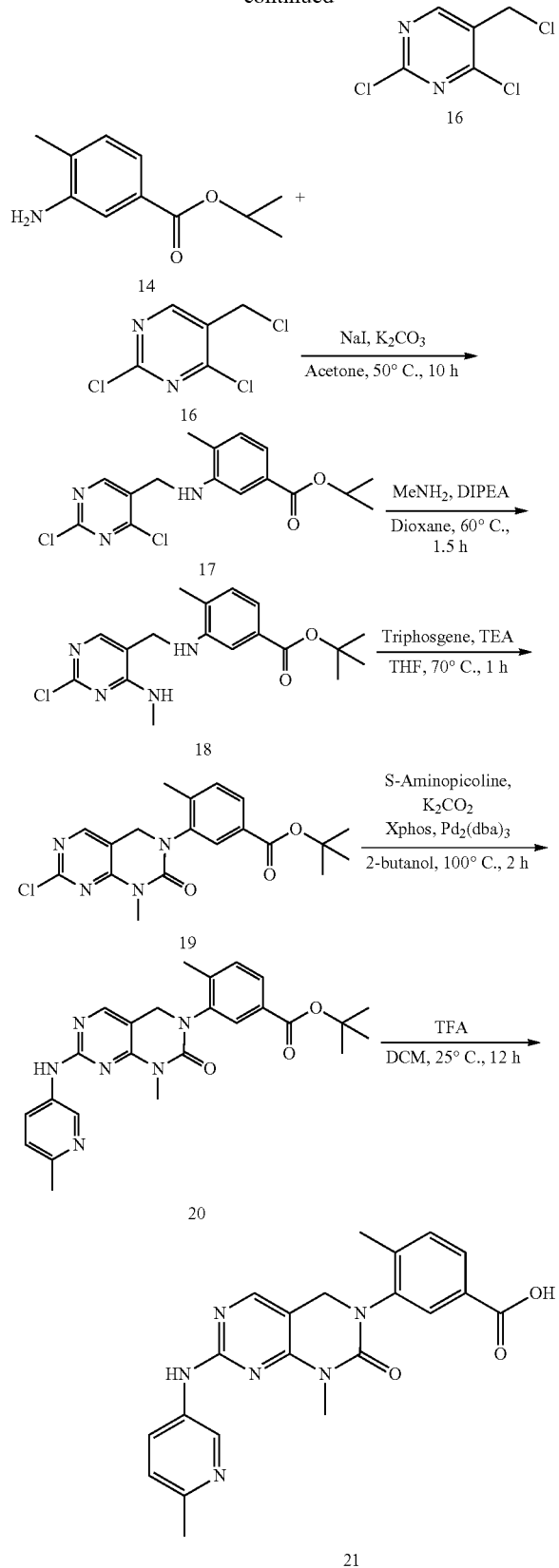

starting material to introduce a protective group into the carboxyl group through an esterification reaction. In the second reaction, the resulting product is reacted with palladium/carbon and cyclohexene at a temperature of 80° C. to reduce the nitro group to an amino group. In the third reaction, N,N-diisopropylethylamine and phosphoryl chloride are added to substitute the hydroxy group of the pyrimidine starting material with a chloro group. In the fourth reaction, sodium iodide and potassium carbonate are added to the benzoate skeleton to prepare a pyrimidine-introduced compound through an $S_N^2$ reaction. In the fifth reaction, methylamine is added to the resulting compound in the presence of a dioxane solvent to prepare a compound through an amination reaction. In the sixth reaction, triphosgene is added to the resulting product to perform a cyclization reaction through urea formation and thereby to prepare a compound. In the seventh reaction, a Buchwald-Hartwig amination reaction is performed using a ligand in the presence of a palladium catalyst to prepare an amine-introduced compound. In the eighth reaction, trifluoroacetic acid is added to the resulting compound to perform deprotection and thereby to prepare a carboxylic acid compound.

In addition, the intermediate compound synthesized during the preparation process according to Reaction Scheme above includes novel compounds, and these novel intermediate compounds also fall within the scope of the present invention.

Specific examples of 4-methyl-3-(1-methyl-7-((6-methylpyridin-3-yl)amino)-2-oxo-1,4-dihydropyrimido[4,d]pyrimidin-3(2H)-yl)benzoic acid represented by Formula 1 according to the present invention and novel intermediate compounds thereof are given below.

tert-butyl-4-methyl-3-nitrobenzoate
tert-butyl-3-amino-4-methylbenzoate
2,4-dichloro-5-(chloromethyl)pyrimidine
tert-butyl-3-(((2,4-dichloropyrimidin-5-yl)methyl)amino)-4-methylbenzoate
tert-butyl-3-(((2-chloro-4-(methylamino)pyrimidin-5-yl)methyl)amino)-4-methyl benzoate
tert-butyl-3-(7-chloro-1-methyl-2-oxo-1,4-dihydropyrimidido[4,5-d]pyrimidin-3(2H)-yl)-4-methylbenzoate
tert-butyl-4-methyl-3-(1-methyl-7-((6-methylpyridin-3-yl)amino)-2-oxo-1,4-dihydropyrimidido[4,5-d]pyrimidine-3(2H)-yl)benzoate
4-methyl-3-(1-methyl-7-((6-methylpyridin-3-yl)amino)-2-oxo-1,4-dihydropyrimidido[4,d]pyrimidine-3(2H)-yl) benzoic acid Step 1: tert-butyl-4-methyl-3-nitrobenzoate

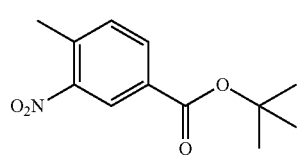 [SMILES: Cc1ccc(C(=O)OC(C)(C)C)cc1[N+](=O)[O-]]

4-methyl-3-nitrobenzoic acid (5 g, 27.6 mmol) was charged in a round-bottom flask and then dissolved in dichloromethane (138 mL). Then, 4-dimethylaminopyridine (0.34 g, 27.6 mmol), tert-butyl alcohol (2.98 mL, 33.1 mmol), and N,N'-dicyclohexylcarbodiimide (6.83 g, 33.1 mmol) were added thereto at 0° C. After stirring at room temperature for two days, the reaction was completed and then the resulting product was extracted with dichloromethane and water. The combined organic layer was dried over anhydrous magnesium sulfate, filtered, distilled under reduced pressure and then dried and the obtained residue was purified by column chromatography (EtOAc:hexane=1:6) to obtain tert-butyl-4-methyl-3-nitrobenzoate (4.97 g, 76%).

¹H NMR (400 MHz, CDCl₃) δ 8.52 (d, J=1.8 Hz, 1H), 8.09 (dd, J=7.9, 1.8 Hz, 1H), 7.40 (d, J=7.9 Hz, 1H), 2.65 (s, 3H), 2.17 (s, 2H), 1.61 (s, 9H).

Step 2: tert-butyl-3-amino-4-methylbenzoate

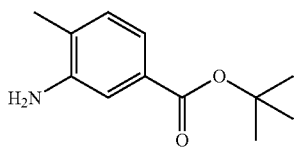

tert-butyl-4-methyl-3-nitrobenzoate (112.70 g, 0.475 mmol) was charged in a round-bottom flask and then dissolved in ethyl alcohol/cyclohexene (1/1, 0.2 M, 2.38 mL). Then, palladium/carbon (24.1 mg, 0.574 mmol) was added thereto. After stirring at 80° C. for 16 hours, the floating matter was filtered using celite. The collected organic layer was distillated under reduced pressure, and then the obtained residue was purified by column chromatography (EtOAc:hexane=1:4) to obtain tert-butyl-3-amino-4-methylbenzoate (91 mg, 92%).

¹H NMR (400 MHz, CDCl₃) δ 7.33 (dd, J=7.7, 1.7 Hz, 1H), 7.29 (d, J=1.7 Hz, 1H), 7.07 (d, J=7.7 Hz, 1H), 3.72 (s, 2H), 2.20 (s, 3H), 1.57 (s, 9H).

Step 3: 2,4-dichloro-5-(chloromethyl)pyrimidine

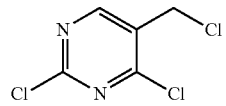

5-(hydroxymethyl)pyrimidine (15 g, 105.6 mmol) was charged in a round-bottom flask and dissolved in toluene (52.8 mL, 2 M). N,N-diisopropylethylamine was added thereto at 0° C. and then phosphoryl chloride (49.21 mL, 528 mmol) was slowly added dropwise, followed by stirring at 110° C. The solvent was removed by distillation under reduced pressure, and the obtained residue was purified by column chromatography (EtOAc:hexane=1:6) to obtain 2,4-dichloro-5-(chloromethyl)pyrimidine (14.81 g, 71%).

¹H NMR (400 MHz, CDCl₃) δ 8.66 (s, 1H), 4.64 (s, 2H).

Step 4: tert-butyl-3-(((2,4-dichloropyrimidin-5-yl)methyl)amino)-4-methylbenzoate

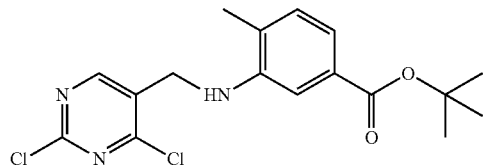 [SMILES: Cc1ccc(C(=O)OC(C)(C)C)cc1NCc1cnc(Cl)nc1Cl]

Tert-butyl-3-amino-4-methylbenzoate (5.32 g, 25.65 mmol) and 2,4-dichloro-5-(chloromethyl)pyrimidine (6.08 g, 30.8 mmol) were charged in a round-bottom flask and then dissolved in acetone (32.06 mL, 0.8 M). Then, sodium iodide (5.77 g, 38.5 mmol) and potassium carbonate (6.74 g, 48.7 mmol) were added thereto. The resulting mixture was stirred at 50° C. for 10 hours, the reaction was completed and then the resulting product was extracted with dichloromethane and water. The collected organic layer was dried over anhydrous magnesium sulfate, filtered, and distilled under reduced pressure, and then the obtained residue was purified by column chromatography (EtOAc:hexane=1:4) to obtain tert-butyl-3-(((2,4-dichloropyrimidin-5-yl)methyl)amino)-4-methylbenzoate (7.17 g, 76%).

¹H NMR (400 MHz, CDCl₃) δ 8.50 (s, 1H), 7.36 (dd, J=7.5, 1.6 Hz, 1H), 7.13 (d, J=7.7 Hz, 1H), 7.07 (d, J=1.6 Hz, 1H), 4.55 (d, J=6.0 Hz, 2H), 2.25 (s, 4H), 1.55 (s, 9H).

Step 5: tert-butyl-3-(((2-chloro-4-(methylamino)pyrimidin-5-yl)methyl)amino)-4-methylbenzoate

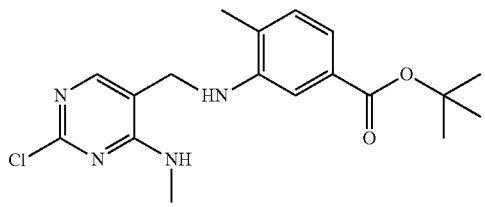 [SMILES: CNc1nc(Cl)ncc1CNc1cc(C(=O)OC(C)(C)C)ccc1C]

Tert-butyl-3-(((2,4-dichloropyrimidin-5-yl)methyl)amino)-4-methylbenzoate (7.17 g, 19.5 mmol) was charged in a round-bottom flask and then dissolved in 1,4-dioxane (64.9 mL, 0.3 M). Methylamine (3.97 mL, 38.9 mmol) and N,N-diisopropylethylamine (10.17 mL, 58.41 mmol) were added thereto, and then the resulting mixture was stirred at 60° C. for 1 hour 30 minutes. Then, when the reaction was completed, the reaction product was extracted with dichloromethane and water. The collected organic layer was dried over anhydrous magnesium sulfate and filtered, the solvent was removed by distillation under reduced pressure, and the obtained residue was purified by column chromatography (EtOAc:hexane=1:1) to obtain tert-butyl-3-(((2-chloro-4-(methylamino)pyrimidin-5-yl)methyl)amino)-4-methylbenzoate (6.72 g, 95%).

¹H NMR (400 MHz, CDCl₃) δ 7.96 (s, 1H), 7.45 (dd, J=7.7, 1.5 Hz, 1H), 7.40 (d, J=1.3 Hz, 1H), 7.15 (d, J=7.7 Hz, 1H), 6.02 (s, 1H), 4.20 (d, J=5.5 Hz, 2H), 3.36 (d, J=5.6 Hz, 1H), 3.04 (d, J=4.9 Hz, 3H), 2.18 (s, 3H), 1.55 (s, 9H).

Step 6: tert-butyl-3-(7-chloro-1-methyl-2-oxo-1,4-dihydropyrimidido[4,5-d]pyrimidin-3(2H)-yl)-4-methyl benzoate

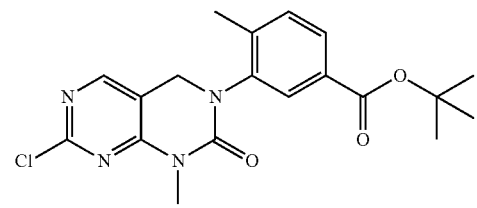 [SMILES: Cc1ccc(C(=O)OC(C)(C)C)cc1N1Cc2cnc(Cl)nc2N(C)C1=O]

Tert-butyl-3-(((2-chloro-4-(methylamino)pyrimidin-5-yl)methyl)amino)-4-methylbenzoate (4.26 g, 11.7 mmol) was added to a round-bottom flask and was dissolved in tetrahydrofuran (39.1 mL, 0.3 M). Then, triphosgene (1.74 g, 5.86 mmol) and triethylamine (8.13 mL, 58.6 mmol) were added thereto at 0° C. After the resulting mixture was stirred at 70° C. for 1 hour, the reaction was completed, and then the reaction product was extracted with dichloromethane and water. The collected organic layer was dried over anhydrous magnesium sulfate and filtered, the solvent was removed by distillation under reduced pressure, and the obtained residue was purified by column chromatography (EtOAc:hexane=1: 6->1:2) and solidified with hexane to obtain tert-butyl-3-(7-chloro-1-methyl-2-oxo-1,4-dihydropyrimidido[4,5-d]pyrimidin-3(2H)-yl)-4-methylbenzoate (1.75 g, 48%).

¹H NMR (400 MHz, CDCl₃) δ 8.12 (s, 1H), 7.90 (dd, J=7.9, 1.8 Hz, 1H), 7.85 (d, J=1.7 Hz, 1H), 7.36 (d, J=8.0 Hz, 1H), 4.83 (dd, J=14.8, 1.1 Hz, 1H), 4.55 (dd, J=14.8, 0.9 Hz, 1H), 3.47 (s, 3H), 2.28 (s, 3H), 1.58 (s, 9H).

Step 7: tert-butyl-4-methyl-3-(1-methyl-7-((6-methylpyridin-3-yl)amino)-2-oxo-1,4-dihydropyrimidido[4,5-d]pyrimidin-3(2H)-yl)benzoate

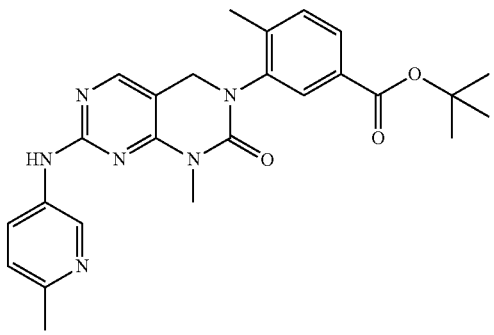 [SMILES: Cc1ccc(Nc2ncc3c(n2)N(C)C(=O)N(c2cc(C(=O)OC(C)(C)C)ccc2C)C3)cn1]

Tert-butyl-3-(7-chloro-1-methyl-2-oxo-1,4-dihydropyrimidido[4,5-d]pyrimidin-3 (2H)-yl)-4-methyl benzoate (1.75 g, 4.50 mmol) was charged in a round-bottom flask and then dissolved in 2-butanol (22.47 mL, 0.2 M). Then, 5-amino-2-methylpyridine (0.49 g, 4.54 mmol), potassium carbonate (3.11 g, 22.48 mmol), 2-dicyclohexylphosphino-2',4',6'-triisopropylbiphenyl (0.43 g, 0.899 mmol), and tris(dibenzylideneacetone)dipalladium (0) (0.82 g, 0.90 mmol) were added thereto, followed by stirring at 100° C. for 2 hours. When the reaction was completed, the floating matter was filtered using celite. The collected organic layer was distilled under reduced pressure and dried, and the obtained residue was purified by column chromatography (dichloromethane:methanol=20:1->10:1) and then solidified using diethyl ether and hexane to obtain tert-butyl-4-methyl-3-(1-methyl-7-((6-methylpyridin-3-yl)amino)-2-oxo-1,4-dihydropyrimidido[4,5-d]pyrimidin-3(2H)-yl)benzoate (1.55 g, 75%).

¹H NMR (400 MHz, CDCl₃) δ 8.72 (s, 1H), 8.00 (m, J=7.7 Hz, 2H), 7.88 (dd, J=7.9, 1.8 Hz, 1H), 7.86 (d, J=1.7 Hz, 1H), 7.34 (d, J=8.0 Hz, 1H), 7.16 (d, J=8.4 Hz, 1H), 7.04 (s, 1H), 4.76 (d, J=14.2 Hz, 1H), 4.46 (d, J=14.0 Hz, 1H), 3.45 (s, 3H), 2.56 (s, 3H), 2.29 (s, 3H), 1.58 (s, 9H).

Step 8: 4-methyl-3-(1-methyl-7-((6-methylpyridin-3-yl)amino)-2-oxo-1,4-dihydropyrimidido[4,d]pyrimidin-3(2H)-yl)benzoic acid

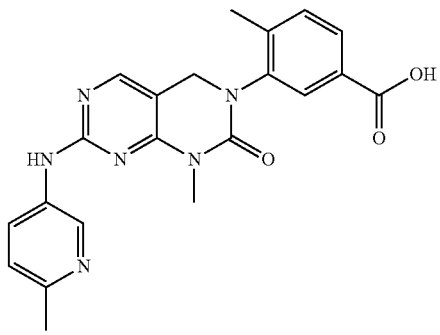 [SMILES: Cc1ccc(Nc2ncc3c(n2)N(C)C(=O)N(c2cc(C(=O)O)ccc2C)C3)cn1]

Tert-butyl-4-methyl-3-(1-methyl-7-((6-methylpyridin-3-yl)amino)-2-oxo-1,4-dihydropyrimidido[4,5-d]pyrimidin-3(2H)-yl)benzoate (0.11 g, 0.2386 mmol) was charged in a round-bottom flask and then dissolved in dichloromethane (2.39 mL, 0.1 M). Then, trifluoroacetic acid (0.36 mL, 4.77 mmol) was added thereto, followed by stirring at room temperature for one day. After the reaction was completed, the reaction solution was distilled under reduced pressure and dried, and the obtained residue was solidified using diethyl ether and hexane to obtain 4-methyl-3-(1-methyl-7-((6-methylpyridin-3-yl)amino)-2-oxo-1,4-dihydropyrimidido[4, d]pyrimidin-3(2H)-yl)benzoic acid (0.09 g, 95%).

¹H NMR (400 MHz, DMSO) δ 10.32 (s, 1H), 9.20 (s, 1H), 8.43 (d, J=9.0 Hz, 1H), 8.23 (s, 1H), 7.93 (d, J=1.8 Hz, 1H), 7.84 (dd, J=7.9, 1.8 Hz, 1H), 7.74 (d, J=8.1 Hz, 1H), 7.46 (d, J=8.0 Hz, 1H), 4.85 (d, J=14.1 Hz, 1H), 4.55 (d, J=14.1 Hz, 1H), 3.37 (s, 3H), 2.61 (s, 3H), 2.22 (s, 3H).

The process for preparing the compounds of Examples 1 to 6 and the process for preparing the compounds of Examples 10 to 25 are given below.

The corresponding target compounds can be synthesized through an amide coupling reaction using HATU between 4-methyl-3-(1-methyl-7-((6-methylpyridin-3-yl)amino)-2-oxo-1,4-dihydropyrimidido[4, d]pyrimidin-3(2H)-yl)benzoic acid (Compound 23), synthesized in step 8 of the intermediate preparation process, and various peptide compounds, as depicted in the following chemical reaction scheme:

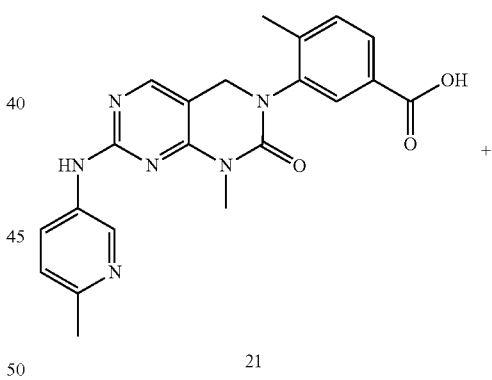

21

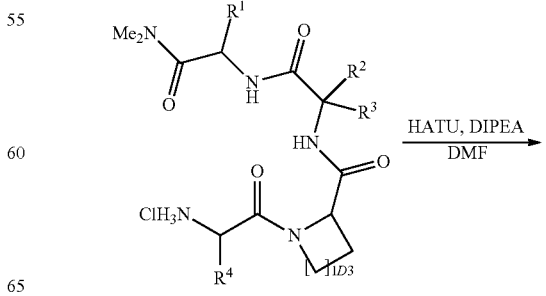

22

-continued

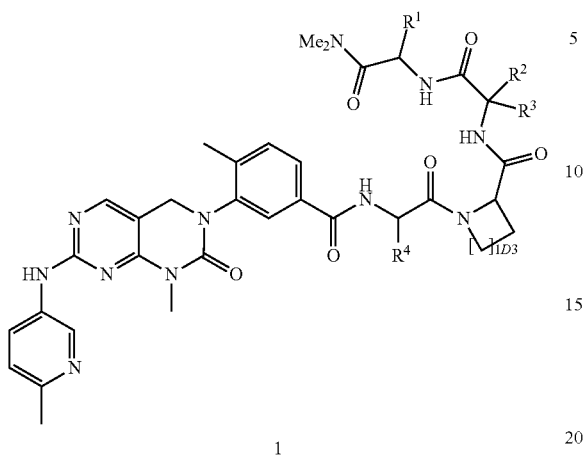

1

Benzoic acid 21 (1.0 eq.) and peptide 22 (1.0 eq.) (peptide 22 derivatives were synthesized in accordance with the following reference: J. Am. Chem. Soc. 2017, 139, 492-516) were charged in a round-bottom flask and dissolved in dimethylformamide (0.2 M). Then, HATU (2.0 eq.) and N,N-diisopropylethylamine (10.0 eq.) were added thereto and stirred for one day. When the reaction was completed, the resulting product was extracted with dichloromethane and an aqueous sodium hydrogen carbonate solution. The collected organic layer was washed several times with water, dried over anhydrous magnesium sulfate, and filtered, and the obtained residue was purified by column chromatography (dichloromethane:methanol=20:1→10:1) to obtain amide 1 (yield of 10 to 20%).

The process for preparing the compounds of Examples 7 to 9 is given below.

The corresponding target compounds can be synthesized through an amide coupling reaction using HATU between 4-methyl-3-(1-methyl-7-((6-methylpyridin-3-yl)amino)-2-oxo-1,4-dihydropyrimidido[4, d]pyrimidin-3(2H)-yl)benzoic acid (Compound 23), synthesized in step 8 of the intermediate preparation process, and various peptide compounds, as depicted in the following chemical reaction scheme:

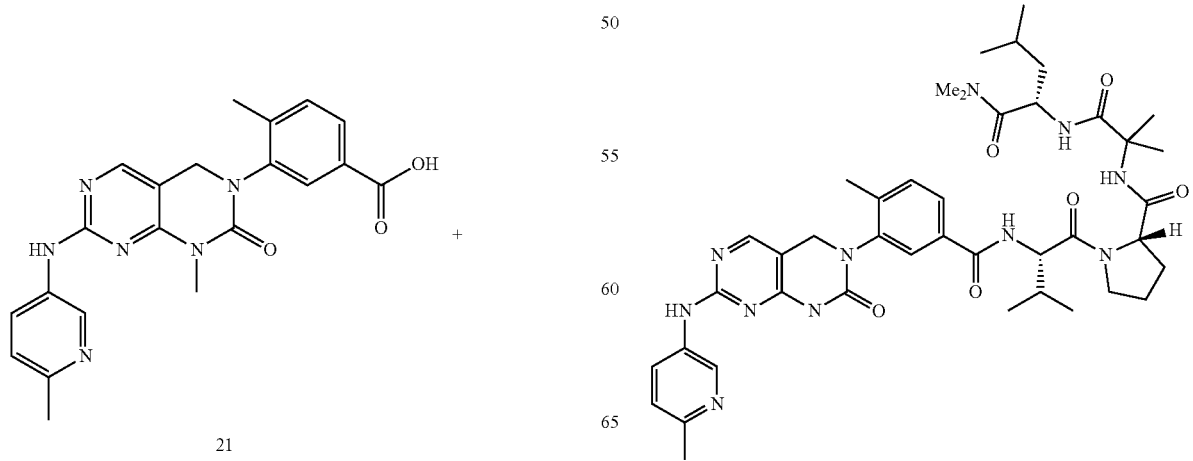

21

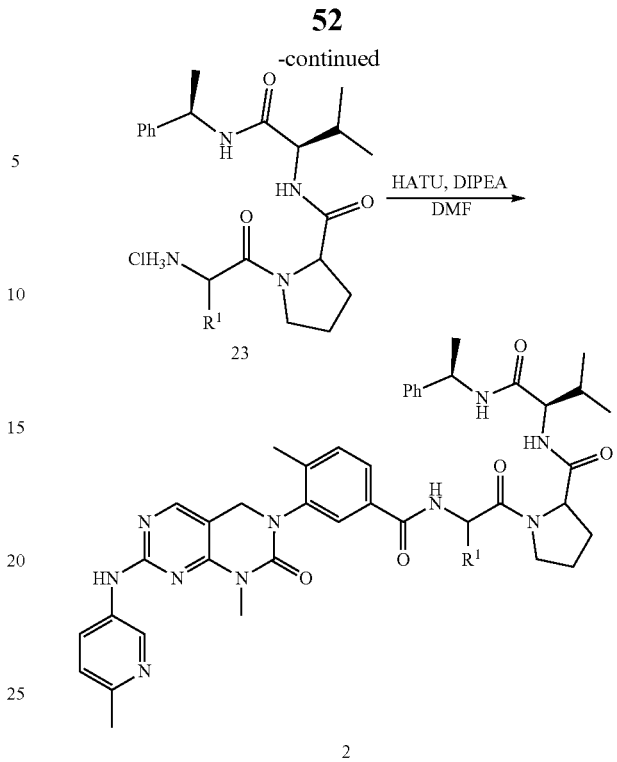

2

Benzoic acid 21 (1.0 eq.) and peptide 23 (1.0 eq.) (peptide 23 derivatives were synthesized in accordance with the following reference: J. Am. Chem. Soc. 2007, 129, 8710-8711) were charged in a round-bottom flask and were dissolved in dimethylformamide (0.2 M). Then, HATU (2.0 eq.) and N,N-diisopropylethylamine (10.0 eq.) were added thereto and stirred for one day. When the reaction was completed, the resulting product was extracted with dichloromethane and an aqueous sodium hydrogen carbonate solution. The collected organic layer was washed several times with water, dried over anhydrous magnesium sulfate, and filtered, and the obtained residue was purified by column chromatography (dichloromethane:methanol=20:1→10:1) to obtain amide 2 (yield of 10 to 20%).

Example 1

(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide HRMS (MM:ESI-APCI+) m/z calc'd for $C_{43}H_{60}N_{11}O_6$ [M+H]$^+$: 826.4728; found: 826.4734.

Example 2

(R)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

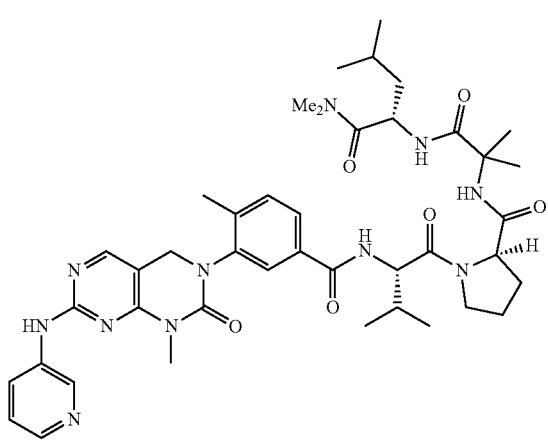 [SMILES: Cc1ccc(C(=O)N[C@H](C(=O)N2CCC[C@@H]2C(=O)NC(C)(C)C(=O)N[C@@H](CC(C)C)C(=O)N(C)C)C(C)C)cc1N1Cc2cnc(Nc3cccnc3)nc2N(C)C1=O]

HRMS (MM:ESI-APCI+) m/z calc'd for $C_{43}H_{60}N_{11}O_6$ [M+H]$^+$: 826.4728; found: 826.4738.

Example 3

(R)—N-(1-(((S)-1-(dimethylamino)-4-methyl-1-oxopentan-2-yl)carbamoyl)cyclopropyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

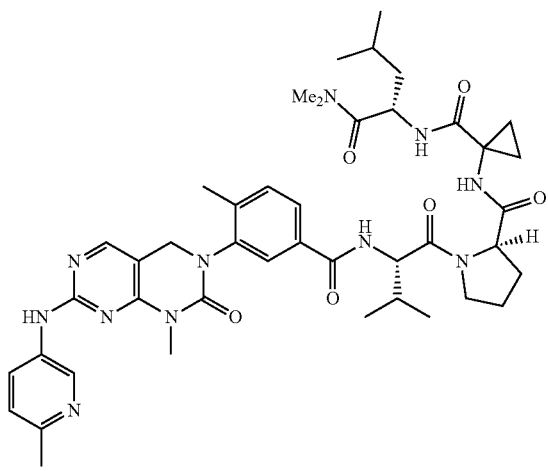 [SMILES: Cc1ccc(Nc2ncc3c(n2)N(C)C(=O)N(c2cc(C(=O)N[C@H](C(=O)N4CCC[C@@H]4C(=O)NC4(C(=O)N[C@@H](CC(C)C)C(=O)N(C)C)CC4)C(C)C)ccc2C)C3)cn1]

HRMS (MM: ESI-APCI+) m/z calc'd for $C_{43}H_{58}N_{11}O_6$ [M+H]$^+$: 824.4572, found: 824.4574.

Example 4

(S)—N-(1-(((S)-1-(dimethylamino)-4-methyl-1-oxopentan-2-yl)carbamoyl)cyclopropyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

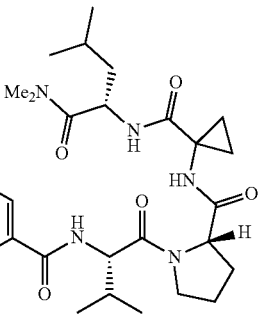

LRMS (MM: ESI-APCI+) m/z calc'd for $C_{43}H_{58}N_{11}O_6$ [M+H]$^+$:824, found:824.

Example 5

(R)—N-(2-(((S)-1-(dimethylamino)-4-methyl-1-oxopentan-2-yl)amino)-2-oxoethyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

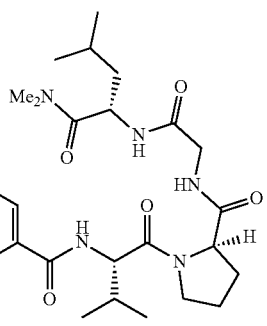

HRMS (MM:ESI-APCI+) m/z calc'd for $C_{41}H_{56}N_{11}O_6$ [M+H]$^+$: 798.4415; found: 798.4425.

Example 6

(S)—N-(2-(((S)-1-(dimethylamino)-4-methyl-1-oxopentan-2-yl)amino)-2-oxoethyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

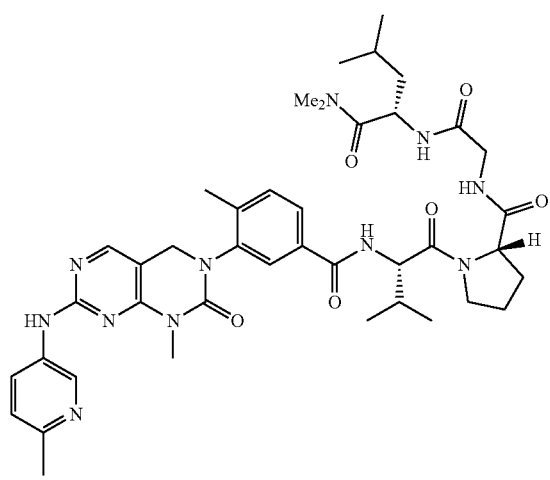 [SMILES: Cc1ccc(Nc2ncc3c(n2)N(C)C(=O)N(c2cc(C(=O)N[C@H](C(=O)N4CCC[C@H]4C(=O)NCC(=O)N[C@@H](CC(C)C)C(=O)N(C)C)C(C)C)ccc2C)C3)cn1]

HRMS (MM:ESI-APCI+) m/z calc'd for $C_{41}H_{56}N_{11}O_6$ [M+H]⁺: 798.4415; found: 798.4420.

Example 7

(R)—N—((S)-3-methyl-1-oxo-1-(((R)-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-phenylalanyl)pyrrolidine-2-carboxamide

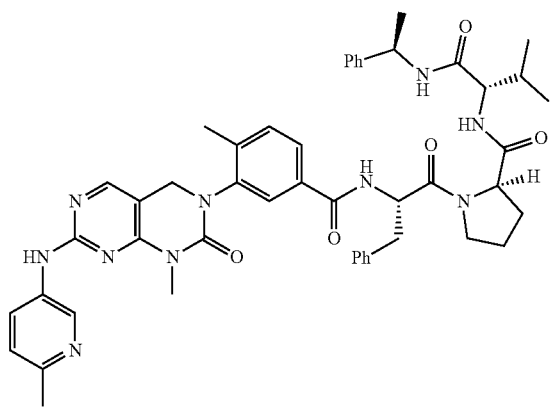 [SMILES: Cc1ccc(Nc2ncc3c(n2)N(C)C(=O)N(c2cc(C(=O)N[C@@H](Cc4ccccc4)C(=O)N4CCC[C@@H]4C(=O)N[C@H](C(=O)N[C@H](C)c4ccccc4)C(C)C)ccc2C)C3)cn1]

HRMS (MM:ESI-APCI+) m/z calc'd for $C_{48}H_{55}N_{10}O_5$ [M+H]⁺: 851.4357; found: 851.4377.

Example 8

(R)—N—((S)-3-methyl-1-oxo-1-(((R)-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

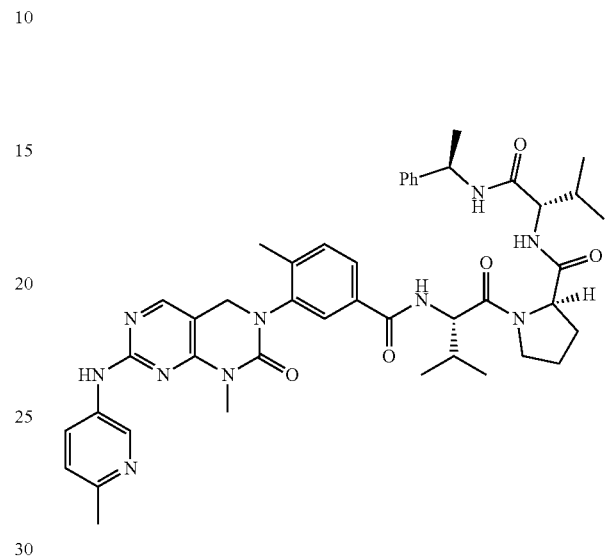

LRMS (MM:ESI-APCI+) m/z calc'd for $C_{44}H_{55}N_{10}O_5$ [M+H]⁺: 803; found: 803.

Example 9

(S)—N—((S)-3-methyl-1-oxo-1-(((R)-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

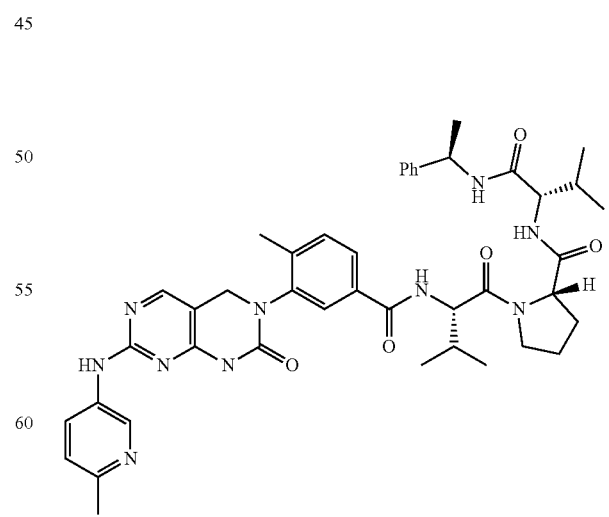

HRMS (MM:ESI-APCI+) m/z calc'd for $C_{44}H_{55}N_{10}O_5$ [M+H]⁺: 803.4357; found: 803.4371.

Example 10

(R)—N-(1-(((R)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-D-valyl)pyrrolidine-2-carboxamide

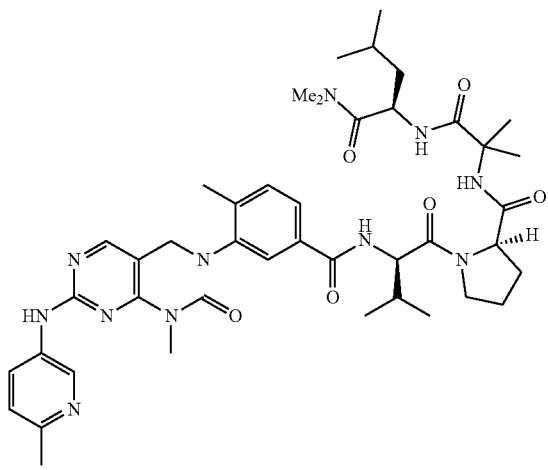 [SMILES: Cc1ccc(Nc2ncc(CNc3cc(C(=O)N[C@@H](C(=O)N4CCC[C@@H]4C(=O)NC(C)(C)C(=O)N[C@H](CC(C)C)C(=O)N(C)C)C(C)C)ccc3C)c(N(C)C=O)n2)cn1]

HRMS (MM:ESI-APCI+) m/z calc'd for $C_{43}H_{60}N_{11}O_6$ [M+H]$^+$: 826.4728; found: 826.4733.

Example 11

(S)—N—(((S)-1-(dimethylamino)-4-methyl-1-oxopentan-2-yl)amino)-1-oxo-3-phenylpropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

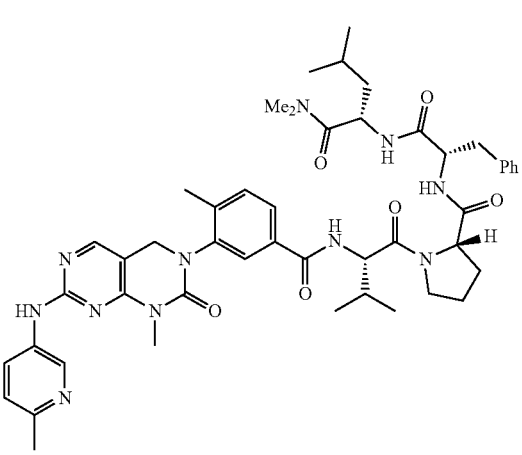 [SMILES: Cc1ccc(Nc2ncc3c(n2)N(C)C(=O)N(c2cc(C(=O)N[C@H](C(=O)N4CCC[C@H]4C(=O)N[C@@H](Cc4ccccc4)C(=O)N[C@@H](CC(C)C)C(=O)N(C)C)C(C)C)ccc2C)C3)cn1]

HRMS (MM:ESI-APCI+) m/z calc'd for $C_{48}H_{62}N_{11}O_6$ [M+H]$^+$: 888.4885; found: 888.4888.

Example 12

(S)—N-(1-(((S)-1-(dimethylamino)-4-methyl-1-oxopentan-2-yl)carbamoyl)cyclobutyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

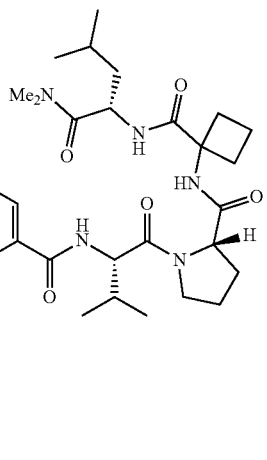

HRMS (MM:ESI-APCI+) m/z calc'd for $C_{44}H_{60}N_{11}O_6$ [M+H]$^+$: 838.4728; found: 838.4726.

Example 13

(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)piperidine-2-carboxamide

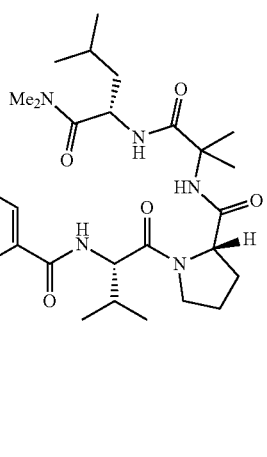

HRMS (MM:ESI-APCI+) m/z calc'd for $C_{44}H_{62}N_{11}O_6$ [M+H]$^+$: 840.4885; found: 840.4897.

Example 14

(S)—N-(1-((2-(dimethylamino)-2-oxoethyl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

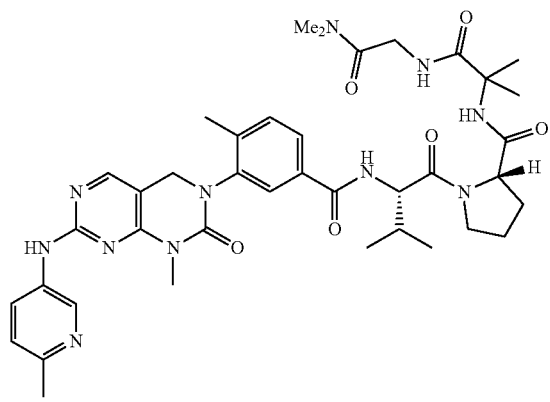 [SMILES: Cc1ccc(Nc2ncc3c(n2)N(C)C(=O)N(c2cc(C(=O)N[C@H](C(=O)N4CCC[C@H]4C(=O)NC(C)(C)C(=O)NCC(=O)N(C)C)C(C)C)ccc2C)C3)cn1]

HRMS (MM:ESI-APCI+) m/z calc'd for $C_{39}H_{52}N_{11}O_6$ [M+H]$^+$: 770.4102; found: 770.4101.

Example 15

(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)azetidine-2-carboxamide

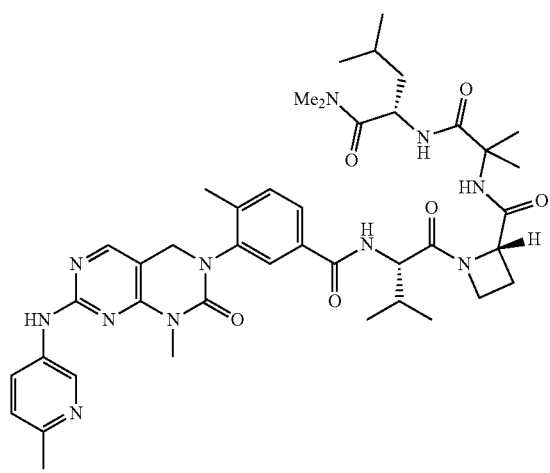 [SMILES: Cc1ccc(Nc2ncc3c(n2)N(C)C(=O)N(c2cc(C(=O)N[C@H](C(=O)N4CC[C@H]4C(=O)NC(C)(C)C(=O)N[C@@H](CC(C)C)C(=O)N(C)C)C(C)C)ccc2C)C3)cn1]

HRMS (MM:ESI-APCI+) m/z calc'd for $C_{42}H_{58}N_{11}O_6$ [M+H]$^+$:812.4572, found:812.4561.

Example 16

(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-isoleucyl)pyrrolidine-2-carboxamide

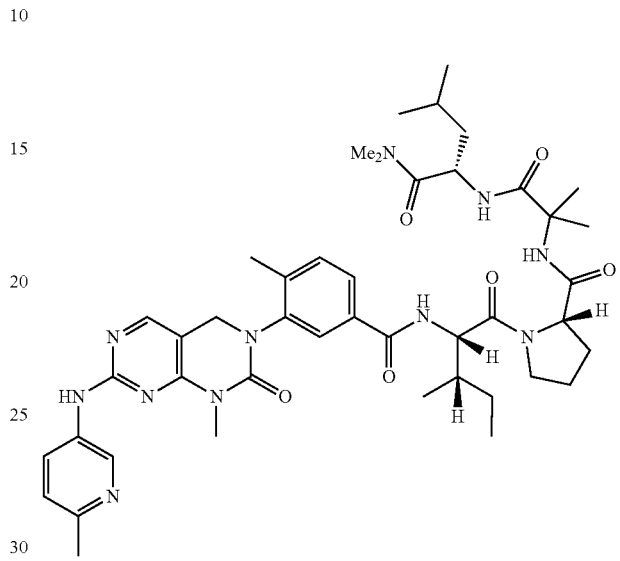

HRMS (MM:ESI-APCI+) m/z calc'd for $C_{44}H_{62}N_{11}O_6$ [M+H]$^+$:840.4885, found: 840.4885.

Example 17

(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-alanyl)pyrrolidine-2-carboxamide

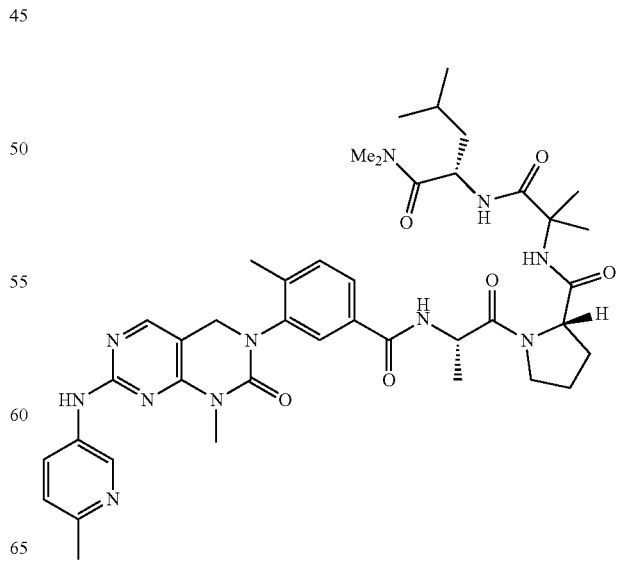

HRMS (MM:ESI-APCI+) m/z calc'd for $C_{41}H_{56}N_{11}O_6$ [M+H]$^+$: 798.4415; found: 798.4418.

Example 18

(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)glycyl)pyrrolidine-2-carboxamide

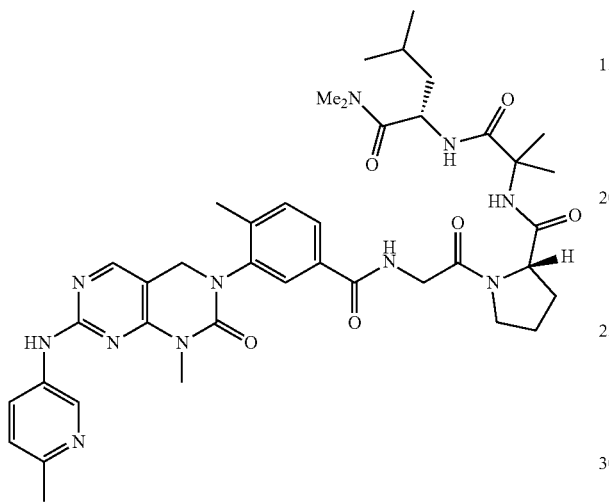

HRMS (MM:ESI-APCI+) m/z calc'd for $C_{40}H_{54}N_{11}O_6$ [M+H]$^+$:784.4259, found: 784.4257.

Example 19

(S)-1-((S)-2-cyclohexyl-2-((4-methyl-3-(1-methyl-7-((6-methylpyridin-3-yl)amino)-2-oxo-1,4-dihydropyrimido[4,5-d]pyrimidin-3(2H)-yl)benzamido)acetyl)-N-(1-(((S)-1-dimethylamino)-4-methyl-1-oxopentan-2-yl)amino)-2-methyl-1-oxopropan-2-yl]pyrrolidine-2-carboxamide

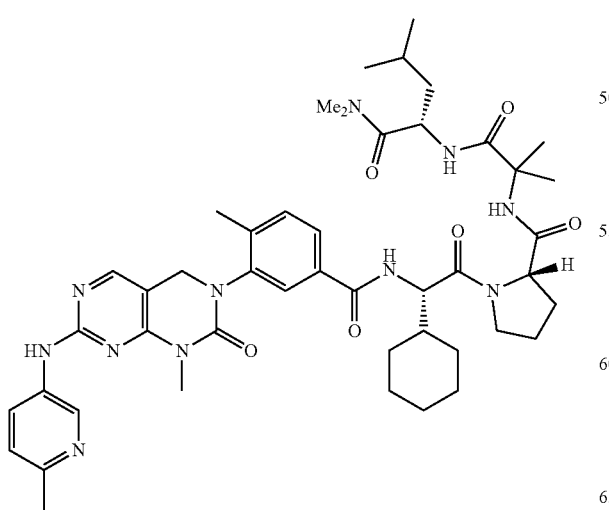

HRMS (MM:ESI-APCI+) m/z calc'd for $C_{46}H_{64}N_{11}O_6$ [M+H]$^+$:866.5041, found: 866.5021.

Example 20

(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-lucyl)pyrrolidine-2-carboxamide

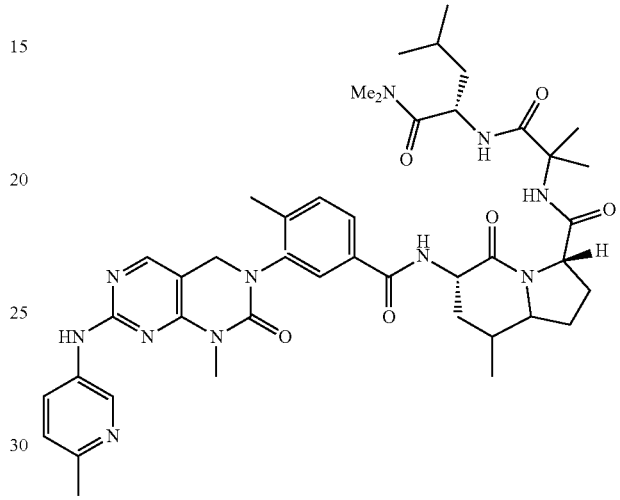

LRMS (MM:ESI-APCI+) m/z calc'd for $C_{44}H_{61}N_{11}O_6Na$ [M+Na]$^+$:862; found:862.

Example 21

(S)—N-(1-(((S)-1-(dimethylamino)-4-methyl-1-oxopentan-2-yl)amino)-2-methyl-1-oxopropan-2-yl)-1-((S)-2-(4-methyl-3-(1-methyl-7-((6-methylpyridin-3-yl)amino)-2-oxo-1,4-dihydropyrimido[4,5-d]pyrimidin-3(2H)-yl)benzamido)pentanoyl)pyrrolidine-2-carboxamide

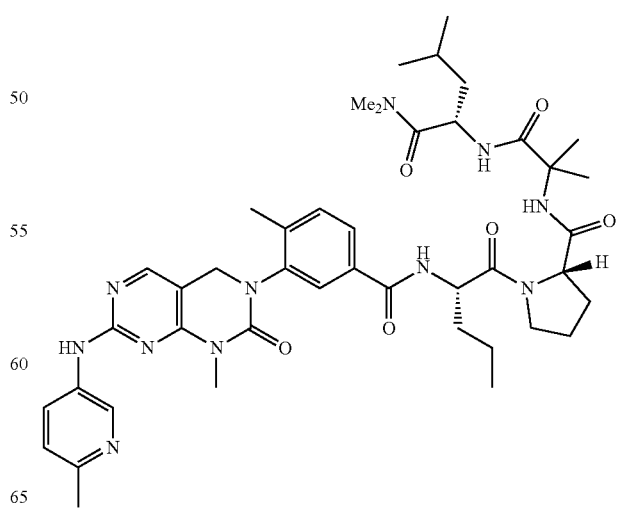

LRMS (MM:ESI-APCI+) m/z calc'd for $C_{43}H_{60}N_{11}O_6$ [M+H]$^+$:826, found:826.

Example 22

(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

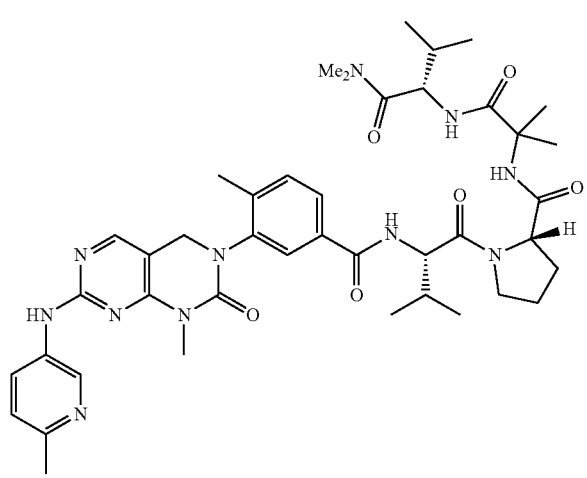 [SMILES: Cc1ccc(Nc2ncc3c(n2)N(C)C(=O)N(c2cc(C(=O)N[C@H](C(=O)N4CCC[C@H]4C(=O)NC(C)(C)C(=O)N[C@H](C(=O)N(C)C)C(C)C)C(C)C)ccc2C)C3)cn1]

LRMS (MM:ESI-APCI+) m/z calc'd for $C_{42}H_{58}N_{11}O_6$ [M+H]$^+$:812, found:812.

Example 23

(R)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide

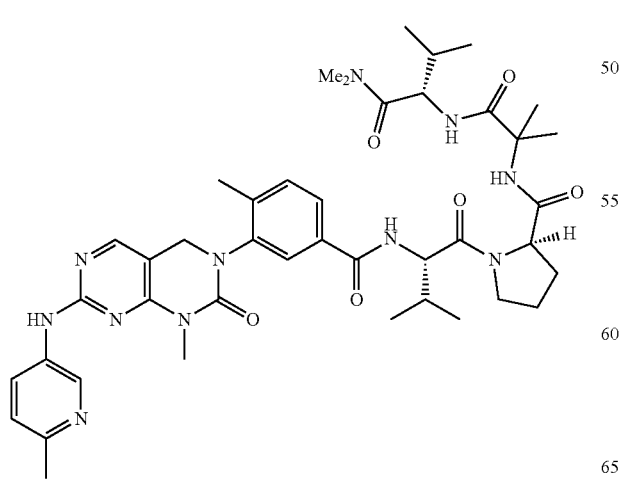

LRMS (MM:ESI-APCI+) m/z calc'd for $C_{42}H_{58}N_{11}O_6$ [M+H]$^+$:812; found:812.

Example 24

(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-phenylalanyl)pyrrolidine-2-carboxamide

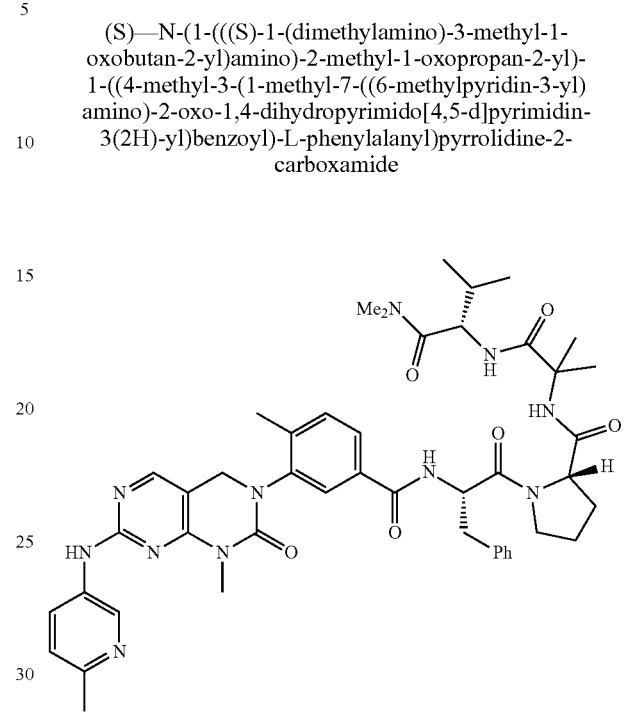

LRMS (MM:ESI-APCI+) m/z calc'd for $C_{46}H_{58}N_{11}O_6$ [M+H]$^+$:860; found:860.

Example 25

(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-alanyl)pyrrolidine-2-carboxamide

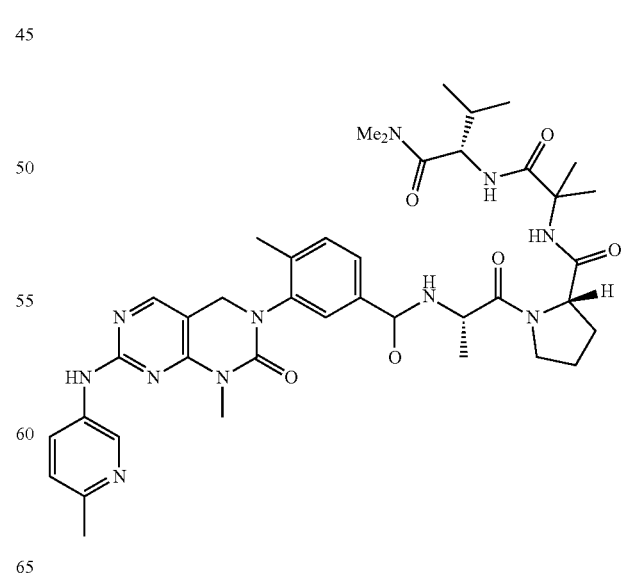

LRMS (MM:ESI-APCI+) m/z calc'd for $C_{40}H_{54}N_{11}O_6$ [M+H]$^+$:784, found:784.

Preparation Example 2

The process for preparing the compounds of Examples 26 to 43 is given below:

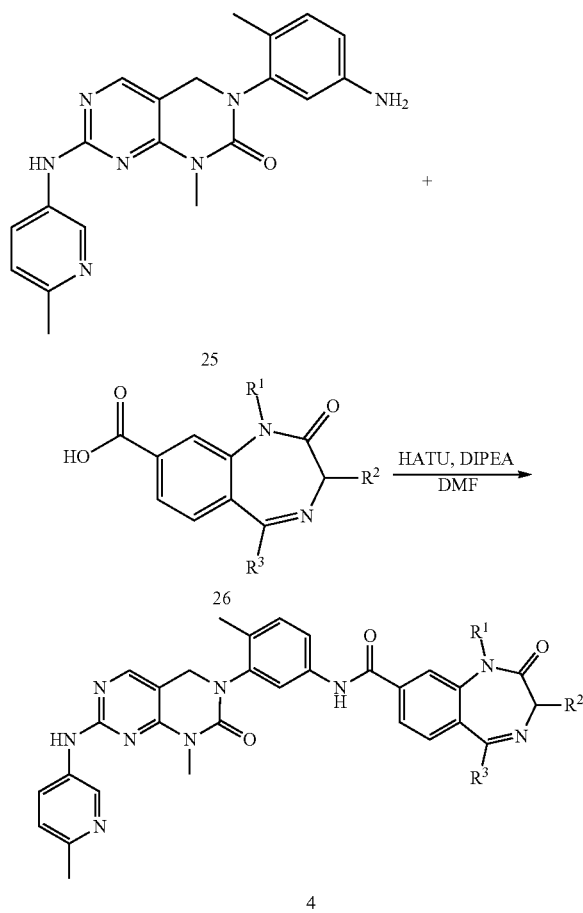

Aniline 25 (1.0 eq.) and carboxylic acid 26 (1.0 eq.) (benzodiazepine 26 derivatives were synthesized in accordance with the following reference: *Bioorg. Med. Chem.* 2015, 23, 7095-7109) were charged in a round-bottom flask and were dissolved in dimethylformamide (0.2 M). Then, HATU (2.0 eq.) and N,N-diisopropylethylamine (10.0 eq.) were added thereto and stirred for one day. When the reaction was completed, the resulting product was extracted with dichloromethane and an aqueous sodium hydrogen carbonate solution. The collected organic layer was washed several times with water, dried over anhydrous magnesium sulfate, and filtered, and the obtained residue was purified by column chromatography (dichloromethane:methanol=20:1→10:1) to obtain amide 4 (yield of 10 to 20%).

Example 26

(S)-3-benzyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

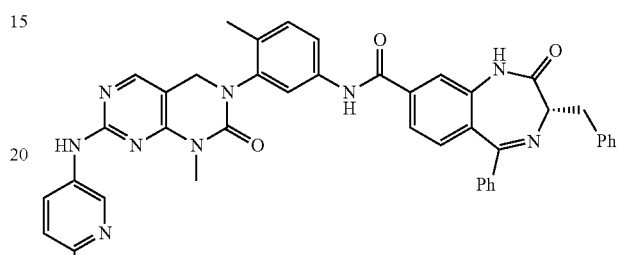

$^1$H NMR (400 MHz, DMSO) δ 10.83 (s, 1H), 10.50 (s, 1H), 9.64 (s, 1H), 8.80 (d, J=2.6 Hz, 1H), 8.16 (d, J=1.6 Hz, 1H), 8.05 (dd, J=8.4, 2.6 Hz, 1H), 7.83 (dd, J=4.0, 2.1 Hz, 1H), 7.76 (s, 1H), 7.69 (dd, J=8.2, 1.7 Hz, 1H), 7.59 (dd, J=8.4, 2.2 Hz, 1H), 7.51 (dt, J=8.6, 4.2 Hz, 1H), 7.44 (d, J=4.4 Hz, 4H), 7.40-7.24 (m, 6H), 7.18 (dd, J=8.0, 5.8 Hz, 2H), 4.71 (d, J=14.0 Hz, 1H), 4.52 (d, J=14.0 Hz, 1H), 3.73 (dd, J=8.1, 5.5 Hz, 1H), 3.42 (td, J=18.2, 16.0, 6.9 Hz, 2H), 3.32 (s, 3H), 2.40 (s, 3H), 2.13 (s, 3H); $^{13}$C NMR (101 MHz, DMSO) δ 170.58, 167.78, 164.89, 159.42, 157.49, 153.73, 152.56, 150.69, 141.65, 140.51, 139.76, 139.67, 139.01, 138.21, 135.18, 131.35, 131.25, 131.20, 130.93, 130.19, 129.78, 129.14, 128.81, 128.55, 126.71, 126.51, 122.93, 121.84, 121.21, 120.08, 119.52, 119.49, 103.42, 65.58, 47.12, 37.61, 28.71, 23.71, 17.28; HRMS (MM: ESI-APCI+) m/z calc'd for $C_{43}H_{38}N_9O_3[M+H]^+$:728.3098; found:728.3102.

Example 27

(S)-3-(3-fluorobenzyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

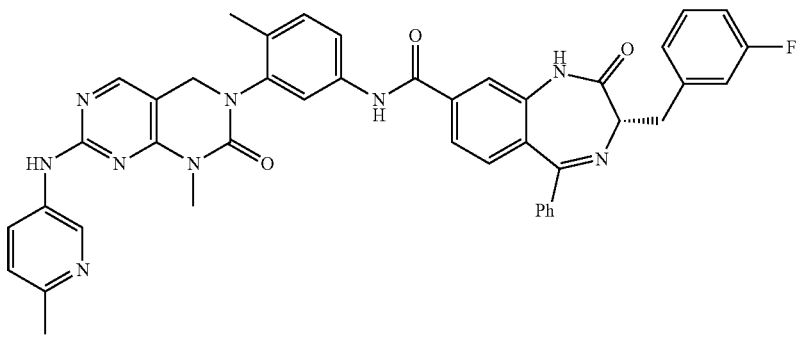 [SMILES: Cc1ccc(Nc2ncc3c(n2)N(C)C(=O)N(c2cc(NC(=O)c4ccc5c(c4)NC(=O)[C@H](Cc4cccc(F)c4)N=C5c4ccccc4)ccc2C)C3)cn1]

LRMS (MM:ESI-APCI+) m/z calc'd for $C_{43}H_{36}FN_9O_3Na[M+Na]^+$:768; found:768.

Example 28

(S)-3-(4-fluorobenzyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

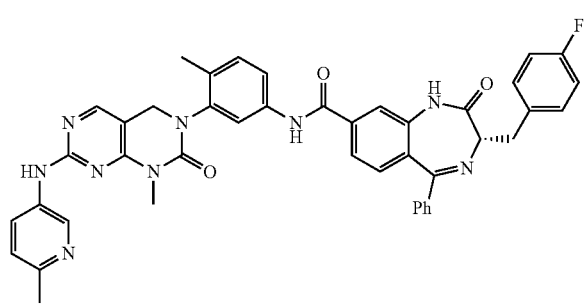 [SMILES: Cc1ccc(Nc2ncc3c(n2)N(C)C(=O)N(c2cc(NC(=O)c4ccc5c(c4)NC(=O)[C@H](Cc4ccc(F)cc4)N=C5c4ccccc4)ccc2C)C3)cn1]

$^1$H NMR (600 MHz, DMSO) δ 10.83 (s, 1H), 10.51 (s, 1H), 9.64 (s, 1H), 8.88-8.72 (m, 1H), 8.16 (s, 1H), 8.08-8.03 (m, 1H), 7.84 (d, J=5.8 Hz, 1H), 7.77 (s, 1H), 7.70 (d, J=8.3 Hz, 1H), 7.60 (d, J=8.3 Hz, 1H), 7.51 (t, J=7.0 Hz, 2H), 7.47-7.35 (m, 8H), 7.30 (d, J=8.4 Hz, 1H), 7.18 (d, J=8.4 Hz, 1H), 7.10 (t, J=8.7 Hz, 3H), 4.71 (d, J=14.0 Hz, 1H), 4.53 (d, J=14.0 Hz, 1H), 3.73 (t, J=6.8 Hz, 1H), 3.41 (dd, J=13.2, 5.3 Hz, 2H), 2.40 (s, 3H), 2.13 (s, 3H); $^{13}$C NMR (151 MHz, DMSO) δ 170.46, 167.77, 164.76, 161.98, 160.38, 159.30, 157.38, 153.62, 152.45, 150.58, 141.53, 140.39, 139.64, 138.89, 138.09, 135.62, 135.60, 135.07, 131.90, 131.85, 131.23, 131.14, 131.11, 130.83, 129.66, 129.03, 128.71, 126.59, 122.83, 121.73, 121.12, 119.98, 119.39, 115.15, 115.02, 103.31, 65.36, 47.00, 38.61, 36.62, 28.61, 23.60, 17.17; HRMS (MM:ESI-APCI+) m/z calc'd for $C_{43}H_{37}FN_9O_3[M+H]^+$:746.3003; found:746.3035.

Example 29

(S)—N-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-methylbenzyl)-2-oxo-5-phenyl-2,3-dihydro-1H-benzo[e][1,4]diazepine-8-carboxamide

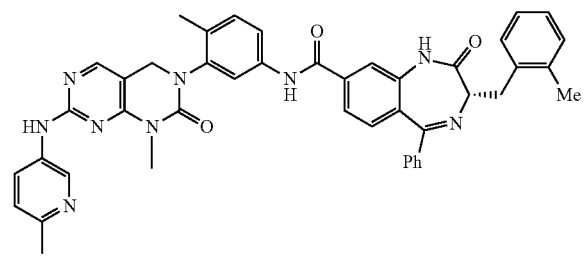 [SMILES: Cc1ccc(Nc2ncc3c(n2)N(C)C(=O)N(c2cc(NC(=O)c4ccc5c(c4)NC(=O)[C@H](Cc4ccccc4C)N=C5c4ccccc4)ccc2C)C3)cn1]

LRMS (MM:ESI-APCI+) m/z calc'd for $C_{44}H_{40}N_9O_3$ [M+H]$^+$:742; found: 742.

Example 30

(S)-3-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

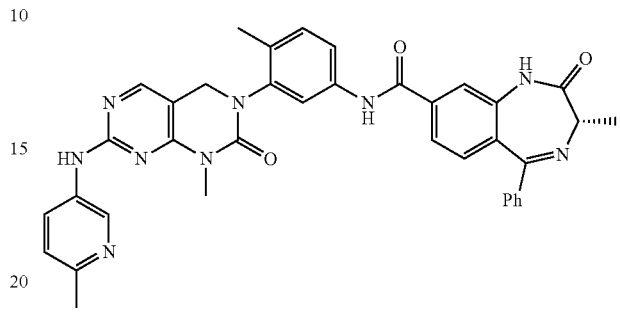

LRMS (MM:ESI-APCI+) m/z calc'd for $C_{37}H_{34}N_9O_3$ [M+H]$^+$:652; found:652.

Example 31

(S)-1-benzyl-3-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

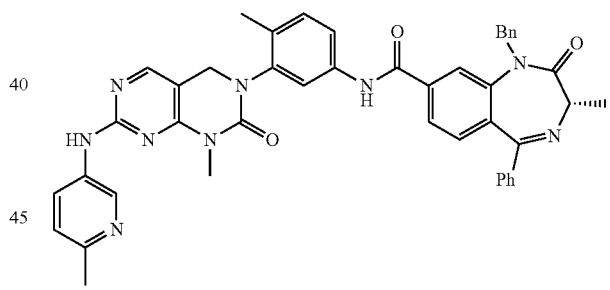

$^1$H NMR (600 MHz, DMSO) δ 10.47 (s, 1H), 9.64 (s, 1H), 8.80 (d, J=2.7 Hz, 1H), 8.21 (d, J=1.7 Hz, 1H), 8.16 (s, 1H), 8.06 (dd, J=8.4, 2.7 Hz, 1H), 7.81 (dd, J=4.7, 2.2 Hz, 1H), 7.75 (dd, J=8.1, 1.7 Hz, 1H), 7.61 (ddd, J=7.3, 4.6, 2.1 Hz, 1H), 7.51 (t, J=7.4 Hz, 1H), 7.42 (t, J=7.6 Hz, 2H), 7.31 (dq, J=6.7, 2.4, 1.6 Hz, 4H), 7.18 (d, J=8.5 Hz, 1H), 7.15-7.08 (m, 3H), 7.00-6.95 (m, 2H), 5.58 (d, J=15.6 Hz, 1H), 5.04 (d, J=15.6 Hz, 1H), 4.70 (d, J=14.0 Hz, 1H), 4.53 (d, J=14.0 Hz, 1H), 3.86 (q, J=6.2 Hz, 1H), 3.34 (s, 3H), 2.41 (s, 3H), 2.14 (s, 3H), 1.61 (d, J=6.3 Hz, 3H); $^{13}$C NMR (151 MHz, DMSO) δ 169.71, 167.06, 164.08, 158.93, 157.02, 153.24, 152.11, 150.17, 141.48, 141.18, 139.94, 137.86, 137.59, 137.45, 137.08, 134.72, 132.49, 130.96, 130.78, 130.44, 129.61, 129.00, 128.38, 128.25, 127.10, 127.04, 126.29, 123.54, 122.49, 122.28, 119.79, 119.29, 102.95, 58.37, 53.60, 48.93, 46.63, 41.84, 28.23, 23.18, 18.08, 17.48, 16.79, 16.72; LRMS (MM:ESI-APCI+) m/z calc'd for $C_{44}H_{40}N_9O_3[M+H]^+$:742; found:742.

Example 32

(R)-3-((R)-sec-butyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

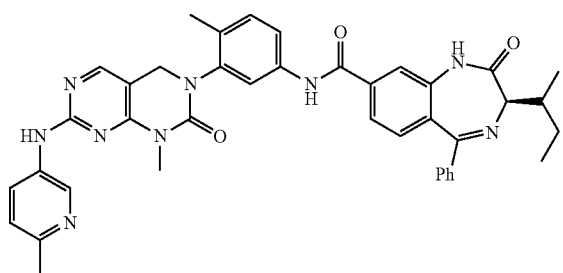 [SMILES: CCC(C)[C@H]1N=C(c2ccccc2)c2ccc(C(=O)Nc3ccc(C)c(N4Cc5cnc(Nc6ccc(C)nc6)nc5N(C)C4=O)c3)cc2NC1=O]

LRMS (MM:ESI-APCI+) m/z calc'd for $C_{40}H_{40}N_9O_3$ [M+H]$^+$:694; found:694.

Example 33

(S)-1-benzyl-3-isobutyl-N-(4-methyl-3-(1-methyl-7-((6-methylpyridin-3-yl) amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

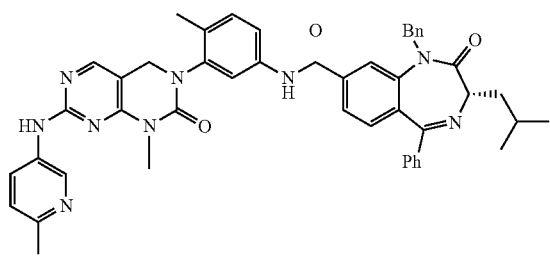

HRMS (MM:ESI-APCI+) m/z calc'd for $C_{47}H_{46}N_9O_3$ [M+H]$^+$:784.3724; found: 784.3715.

Example 34

(S)-3-benzyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide

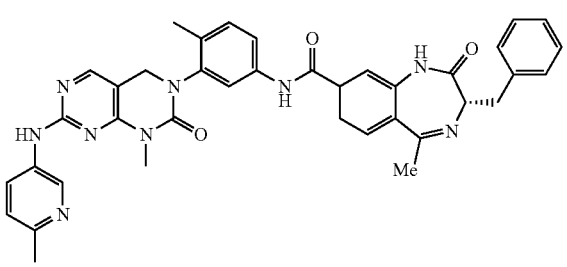 [SMILES: CC1=N[C@@H](Cc2ccccc2)C(=O)NC2=CC(C(=O)Nc3ccc(C)c(N4Cc5cnc(Nc6ccc(C)nc6)nc5N(C)C4=O)c3)CC=C21]

$^1$H NMR (600 MHz, DMSO) δ 10.66 (s, 1H), 10.44 (s, 1H), 9.66 (s, 1H), 8.81 (d, J=2.7 Hz, 1H), 8.15 (d, J=3.0 Hz, 1H), 8.06 (dd, J=8.5, 2.6 Hz, 1H), 7.88-7.79 (m, 2H), 7.75-7.71 (m, 1H), 7.64 (s, 1H), 7.59 (d, J=8.2 Hz, 1H), 7.29 (d, J=8.4 Hz, 1H), 7.27-7.16 (m, 5H), 7.14 (t, J=7.3 Hz, 1H), 4.70 (d, J=13.7 Hz, 1H), 4.55-4.45 (m, 1H), 3.55 (d, J=14.0 Hz, 1H), 3.52 (s, 3H), 3.44-3.40 (m, 1H), 3.34 (s, 3H), 3.16 (dt, J=15.0, 7.5 Hz, 1H), 2.41 (s, 6H), 2.13 (s, 3H); $^{13}$C NMR (151 MHz, DMSO) δ 169.93, 167.27, 164.76, 159.28, 157.37, 153.59, 152.45, 150.45, 141.52, 140.14, 139.58, 138.08, 137.61, 137.59, 135.14, 131.19, 131.12, 130.88, 129.90, 129.87, 129.14, 128.40, 126.75, 126.30, 122.93, 122.23, 120.87, 119.95, 119.42, 119.38, 103.34, 64.85, 46.99, 37.34, 28.61, 25.86, 23.49, 17.16; HRMS (MM:ESI-APCI+) m/z calc'd for $C_{38}H_{36}N_9O_3$[M+H]$^+$:666.2941, found: 666.2943.

Example 35

(R)-3-benzyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide

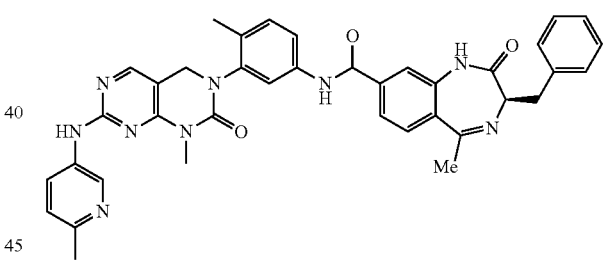

$^1$H NMR (600 MHz, DMSO) δ 10.66 (s, 1H), 10.44 (s, 1H), 9.66 (s, 1H), 8.81 (d, J=2.7 Hz, 1H), 8.15 (d, J=3.0 Hz, 1H), 8.06 (dd, J=8.5, 2.6 Hz, 1H), 7.88-7.79 (m, 2H), 7.75-7.71 (m, 1H), 7.64 (s, 1H), 7.59 (d, J=8.2 Hz, 1H), 7.29 (d, J=8.4 Hz, 1H), 7.27-7.16 (m, 5H), 7.14 (t, J=7.3 Hz, 1H), 4.70 (d, J=13.7 Hz, 1H), 4.55-4.45 (m, 1H), 3.55 (d, J=14.0 Hz, 1H), 3.52 (s, 3H), 3.44-3.40 (m, 1H), 3.34 (s, 3H), 3.16 (dt, J=15.0, 7.5 Hz, 1H), 2.41 (s, 6H), 2.13 (s, 3H); $^{13}$C NMR (151 MHz, DMSO) δ 169.93, 167.27, 164.76, 159.28, 157.37, 153.59, 152.45, 150.45, 141.52, 140.14, 139.58, 138.08, 137.61, 137.59, 135.14, 131.19, 131.12, 130.88, 129.90, 129.87, 129.14, 128.40, 126.75, 126.30, 122.93, 122.23, 120.87, 119.95, 119.42, 119.38, 103.34, 64.85, 46.99, 37.34, 28.61, 25.86, 23.49, 17.16; HRMS (MM:ESI-APCI+) m/z calc'd for $C_{38}H_{36}N_9O_3$[M+H]$^+$:666.2941, found:666.2947.

Example 36

(R)-3-benzyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

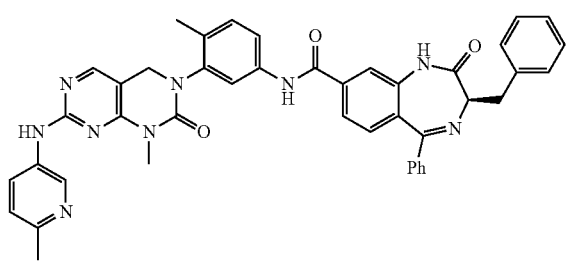 [SMILES: Cc1ccc(Nc2ncc3c(n2)N(C)C(=O)N(c2cc(NC(=O)c4ccc5c(c4)NC(=O)[C@@H](Cc4ccccc4)N=C5c4ccccc4)ccc2C)C3)cn1]

LRMS (MM:ESI-APCI+) m/z calc'd for $C_{43}H_{38}N_9O_3$ [M+H]$^+$:728; found:728.

Example 37

(S)-3-isobutyl-1-methyl-N-(4-methyl-3-(1-methyl-7-((6-methylpyridin-3-yl) amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

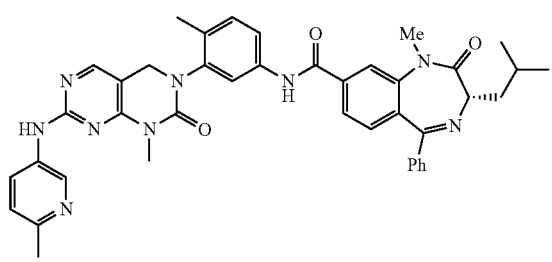 [SMILES: Cc1ccc(Nc2ncc3c(n2)N(C)C(=O)N(c2cc(NC(=O)c4ccc5c(c4)N(C)C(=O)[C@H](CC(C)C)N=C5c4ccccc4)ccc2C)C3)cn1]

$^1$H NMR (600 MHz, DMSO) δ 10.53 (s, 1H), 9.76 (s, 1H), 8.87 (t, J=2.5 Hz, 1H), 8.18 (s, 1H), 8.12 (d, J=8.5 Hz, 1H), 8.06 (s, 1H), 7.85-7.81 (m, 1H), 7.80 (d, J=8.2 Hz, 1H), 7.65-7.61 (m, 1H), 7.55 (d, J=7.6 Hz, 2H), 7.52 (d, J=7.3 Hz, 1H), 7.46 (dd, J=11.7, 7.8 Hz, 3H), 7.33 (d, J=8.4 Hz, 1H), 7.27 (d, J=8.5 Hz, 1H), 4.72 (d, J=14.0 Hz, 1H), 4.55 (d, J=14.0 Hz, 1H), 3.62 (ddq, J=9.6, 6.8, 3.4, 2.8 Hz, 1H), 3.57 (dt, J=8.9, 5.4 Hz, 1H), 3.35 (s, 3H), 3.14 (qd, J=7.4, 4.1 Hz, 2H), 2.44 (s, 3H), 2.15 (s, 4H), 1.92-1.78 (m, 2H), 0.94 (d, J=6.4 Hz, 3H), 0.76 (d, J=6.3 Hz, 3H); $^{13}$C NMR (151 MHz, DMSO) b 170.28, 167.36, 164.71, 159.15, 157.42, 153.61, 152.45, 149.85, 143.69, 141.53, 138.36, 138.03, 137.98, 135.53, 131.31, 131.17, 130.91, 130.80, 130.16, 129.57, 128.76, 123.56, 123.31, 121.38, 120.16, 119.61, 103.59, 61.52, 53.96, 46.99, 42.21, 35.10, 28.64, 24.53, 23.74, 22.93, 22.14, 18.45, 17.17, 17.09, 12.86; HRMS (MM:ESI-APCI+) m/z calc'd for $C_{41}H_{42}N_9O_3$[M+H]$^+$:708.3411; found: 708.3407.

Example 38

(S)-1-allyl-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

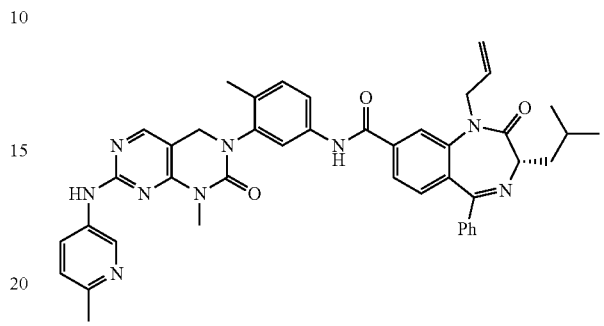

$^1$H NMR (600 MHz, DMSO) δ 10.51 (s, 1H), 9.65 (s, 1H), 8.89-8.64 (m, 1H), 8.14 (d, J=31.3 Hz, 2H), 8.08-8.01 (m, 1H), 7.81 (m, 2H), 7.62 (d, J=8.3 Hz, 1H), 7.57-7.39 (m, 6H), 7.32 (d, J=8.3 Hz, 1H), 7.18 (d, J=8.3 Hz, 1H), 5.76 (ddt, J=16.1, 10.3, 5.0 Hz, 1H), 5.04 (d, J=10.4 Hz, 1H), 4.98 (d, J=17.3 Hz, 1H), 4.73 (dd, J=18.1, 7.8 Hz, 2H), 4.60-4.50 (m, 2H), 3.64 (dd, J=8.8, 4.5 Hz, 1H), 3.34 (s, 3H), 2.40 (s, 3H), 2.14 (s, 3H), 2.11 (m, 1H), 1.88 (dd, J=12.9, 7.1 Hz, 2H), 0.94 (d, J=5.7 Hz, 3H), 0.77 (d, J=5.6 Hz, 3H); $^{13}$C NMR (151 MHz, DMSO) δ 169.22, 167.53, 164.63, 159.31, 157.38, 153.62, 152.48, 150.58, 142.44, 141.56, 140.39, 138.37, 138.02, 138.00, 135.06, 133.77, 131.85, 131.33, 131.16, 130.93, 130.15, 129.45, 128.84, 126.59, 123.70, 122.08, 122.00, 120.15, 120.13, 119.63, 119.60, 116.64, 103.31, 61.69, 49.16, 47.00, 40.42, 28.61, 24.63, 23.66, 23.60, 22.30, 17.17; HRMS (MM: ESI-APCI+) m/z calc'd for $C_{43}H_{44}N_9O_3$[M+H]$^+$:734.3567; found:734.3565.

Example 39

(S)-1,3-diisobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

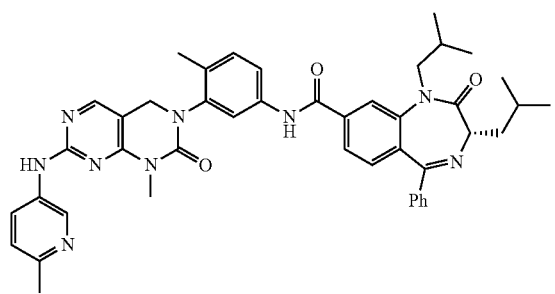 [SMILES: Cc1ccc(Nc2ncc3c(n2)N(C)C(=O)N(c2cc(NC(=O)c4ccc5c(c4)N(CC(C)C)C(=O)[C@H](CC(C)C)N=C5c4ccccc4)ccc2C)C3)cn1]

$^1$H NMR (600 MHz, DMSO) δ 10.48 (s, 1H), 9.65 (s, 1H), 8.80 (d, J=2.6 Hz, 1H), 8.17 (d, J=3.0 Hz, 2H), 8.05 (dd, J=8.6, 2.7 Hz, 1H), 7.86-7.77 (m, 2H), 7.64 (dt, J=5.9, 2.9 Hz, 1H), 7.57-7.51 (m, 3H), 7.48 (t, J=7.4 Hz, 2H), 7.44 (d,

J=8.1 Hz, 1H), 7.33 (d, J=8.4 Hz, 1H), 7.18 (d, J=8.5 Hz, 1H), 4.71 (d, J=13.9 Hz, 1H), 4.54 (d, J=14.0 Hz, 1H), 4.21 (dd, J=13.8, 8.9 Hz, 1H), 3.66 (dd, J=13.8, 5.9 Hz, 1H), 3.57 (dd, J=8.9, 4.4 Hz, 1H), 3.34 (s, 3H), 2.41 (s, 3H), 2.15 (s, 3H), 2.14-2.09 (m, 1H), 1.83 (tt, J=13.0, 7.4 Hz, 2H), 1.66 (p, J=6.7 Hz, 1H), 0.93 (d, J=6.1 Hz, 3H), 0.75 (d, J=6.1 Hz, 3H), 0.71 (d, J=6.6 Hz, 3H), 0.53 (d, J=6.6 Hz, 3H); $^{13}$C NMR (151 MHz, DMSO) δ 170.12, 167.31, 164.54, 159.31, 157.39, 153.63, 152.48, 150.58, 142.48, 141.55, 140.39, 138.16, 137.97, 135.06, 132.44, 131.34, 131.15, 130.93, 130.09, 129.35, 128.88, 126.59, 123.91, 122.83, 122.41, 120.25, 119.77, 119.73, 103.31, 61.72, 52.75, 47.01, 31.32, 28.61, 27.11, 24.59, 23.71, 23.60, 22.43, 22.24, 20.23, 19.50, 17.18, 14.33; HRMS (MM: ESI-APCI+) m/z calc'd for $C_{44}H_{48}N_9O_3$[M+H]$^+$: 750.3880; found:750.3883.

Example 40

(S)-3-isobutyl-1,5-dimethyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide Example 41

(S)-1-benzyl-3-isobutyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide

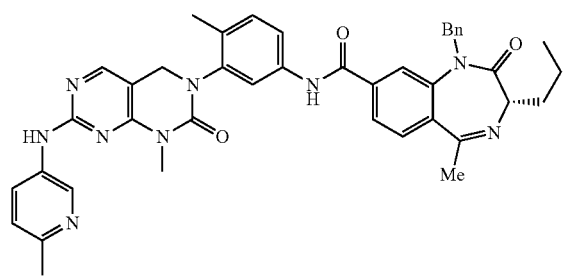

LRMS (MM:ESI-APCI+) m/z calc'd for $C_{42}H_{44}N_9O_3$ [M+H]$^+$:722; found:722.

Example 42

(S)-3-isobutyl-1-(2-methoxyethyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

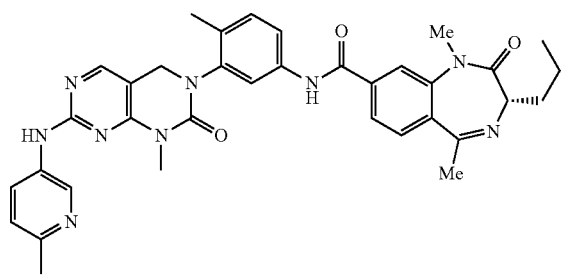 [SMILES: CCC[C@@H]1N=C(C)c2ccc(C(=O)Nc3ccc(C)c(N4Cc5cnc(Nc6ccc(C)nc6)nc5N(C)C4=O)c3)cc2N(C)C1=O]

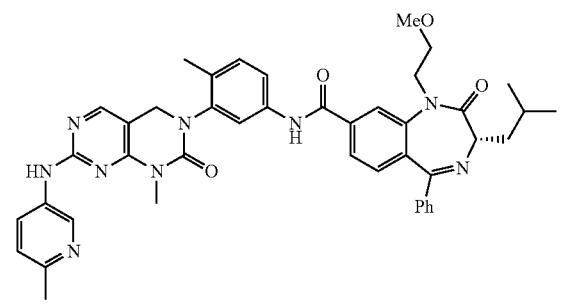 [SMILES: COCCN1C(=O)[C@H](CC(C)C)N=C(c2ccccc2)c2ccc(C(=O)Nc3ccc(C)c(N4Cc5cnc(Nc6ccc(C)nc6)nc5N(C)C4=O)c3)cc21]

$^1$H NMR (600 MHz, DMSO) δ 10.45 (s, 1H), 9.64 (s, 1H), 8.80 (d, J=2.7 Hz, 1H), 8.16 (s, 1H), 8.05 (dd, J=8.5, 2.7 Hz, 1H), 7.95 (s, 1H), 7.88 (d, J=8.1 Hz, 1H), 7.85-7.77 (m, 2H), 7.68-7.61 (m, 1H), 7.32 (d, J=8.4 Hz, 1H), 7.17 (d, J=8.4 Hz, 1H), 4.70 (d, J=13.9 Hz, 1H), 4.53 (d, J=14.0 Hz, 1H), 3.40 (m, 1H), 3.36 (s, 3H), 3.34 (s, 3H), 2.43 (s, 3H), 2.40 (s, 3H), 2.14 (s, 3H), 1.93 (ddd, J=13.5, 8.4, 5.2 Hz, 1H), 1.72 (ddp, J=33.0, 13.6, 6.6, 6.1 Hz, 2H), 0.85 (d, J=6.4 Hz, 3H), 0.70 (d, J=6.3 Hz, 3H); $^{13}$C NMR (151 MHz, DMSO) δ 170.07, 167.18, 164.65, 159.31, 157.39, 153.61, 152.48, 150.57, 141.77, 141.54, 140.39, 138.00, 137.50, 135.06, 132.63, 131.27, 131.14, 128.14, 126.59, 123.59, 122.82, 121.23, 121.20, 120.14, 119.66, 103.31, 60.66, 47.00, 35.06, 28.61, 25.44, 24.23, 23.60, 23.58, 22.11, 17.17; HRMS (MM: ESI-APCI+) m/z calc'd for $C_{36}H_{40}N_9O_3$ [M+H]$^+$:646.3254; found:646.3265.

$^1$H NMR (600 MHz, DMSO) δ 10.51 (s, 1H), 9.65 (s, 1H), 8.80 (d, J=2.7 Hz, 1H), 8.16 (d, J=2.8 Hz, 2H), 8.05 (dd, J=8.5, 2.7 Hz, 1H), 7.85-7.76 (m, 2H), 7.64 (dd, J=8.4, 2.2 Hz, 1H), 7.55-7.50 (m, 3H), 7.49-7.44 (m, 2H), 7.39 (d, J=8.1 Hz, 1H), 7.33 (d, J=8.4 Hz, 1H), 7.18 (d, J=8.5 Hz, 1H), 4.71 (d, J=14.0 Hz, 1H), 4.54 (d, J=14.0 Hz, 1H), 4.40 (dt, J=14.5, 5.6 Hz, 1H), 3.99 (ddd, J=14.4, 6.5, 4.2 Hz, 1H), 3.58 (dd, J=8.7, 4.5 Hz, 1H), 3.42-3.35 (m, 2H), 3.34 (s, 3H), 2.95 (s, 3H), 2.41 (s, 3H), 2.14 (s, 3H), 2.11 (q, J=8.8 Hz, 1H), 1.86-1.80 (m, 2H), 0.93 (d, J=5.9 Hz, 3H), 0.76 (d, J=5.9 Hz, 3H); $^{13}$C NMR (151 MHz, DMSO) δ 169.32, 167.58, 164.67, 159.31, 157.39, 153.62, 152.48, 150.58, 142.78, 141.56, 140.39, 138.48, 138.04, 138.03, 137.81, 135.06, 132.37, 131.29, 131.16, 131.14, 130.78, 129.81, 129.42, 128.69, 126.59, 123.91, 122.86, 122.83, 120.16, 120.14, 119.64, 119.60, 103.31, 69.70, 61.57, 58.27, 47.01, 28.61, 24.63, 23.67, 23.60, 22.29, 17.18; HRMS (MM: ESI-APCI+) m/z calc'd for $C_{43}H_{46}N_9O_4$[M+H]$^+$:752.3673; found:752.3667.

Example 43

(S)-1-(2-(benzylamino)-2-oxoethyl)-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide

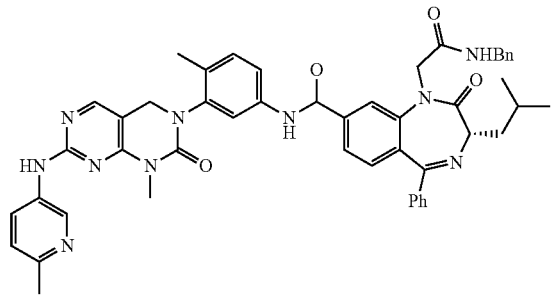

¹H NMR (600 MHz, DMSO) δ 10.54 (s, 1H), 9.65 (s, 1H), 8.81 (d, J=2.8 Hz, 1H), 8.67 (t, J=6.0 Hz, 1H), 8.17 (s, 1H), 8.09-7.99 (m, 2H), 7.82 (q, J=2.4 Hz, 1H), 7.80-7.77 (m, 1H), 7.63 (dd, J=8.1, 2.4 Hz, 1H), 7.56-7.53 (m, 2H), 7.51 (t, J=7.3 Hz, 1H), 7.45 (t, J=7.5 Hz, 2H), 7.40 (d, J=8.1 Hz, 1H), 7.34 (d, J=8.5 Hz, 1H), 7.25 (dt, J=15.7, 7.6 Hz, 4H), 7.18 (dd, J=8.1, 4.6 Hz, 2H), 4.66 (dtd, J=46.8, 16.2, 15.1, 3.8 Hz, 3H), 4.55 (d, J=14.0 Hz, 1H), 4.34 (dd, J=15.4, 6.0 Hz, 1H), 4.26 (dd, J=15.4, 5.7 Hz, 1H), 3.66 (qd, J=4.5, 1.9 Hz, 1H), 3.35 (s, 3H), 2.41 (s, 3H), 2.15 (s, 3H), 2.13 (d, J=8.8 Hz, 1H), 1.90-1.82 (m, 2H), 0.95 (d, J=6.1 Hz, 3H), 0.78 (d, J=5.9 Hz, 3H); ¹³CNMR (151 MHz, DMSO) δ 169.56, 167.99, 167.90, 164.84, 159.32, 157.39, 153.62, 152.49, 150.55, 143.08, 141.58, 140.35, 139.43, 138.73, 138.07, 138.05, 137.94, 135.08, 131.62, 131.32, 131.19, 130.70, 130.04, 129.66, 128.61, 128.59, 127.44, 127.08, 126.63, 123.43, 122.84, 122.13, 122.12, 120.09, 119.60, 119.56, 103.30, 63.16, 61.40, 50.68, 47.02, 42.48, 40.22, 28.61, 24.61, 23.73, 23.57, 22.25, 17.18; HRMS (MM: ESI-APCI+) m/z calc'd for $C_{49}H_{49}N_{10}O_4[M+H]^+$: 841.3938; found: 841.3947.

Preparation Example 3

The process for preparing the compounds of Examples 44 to 46 is given below:

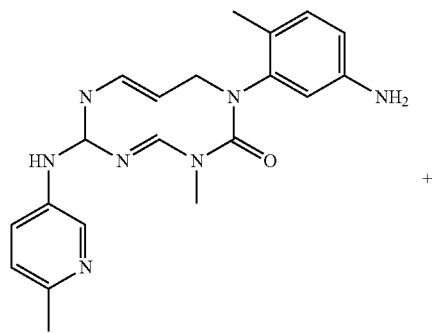

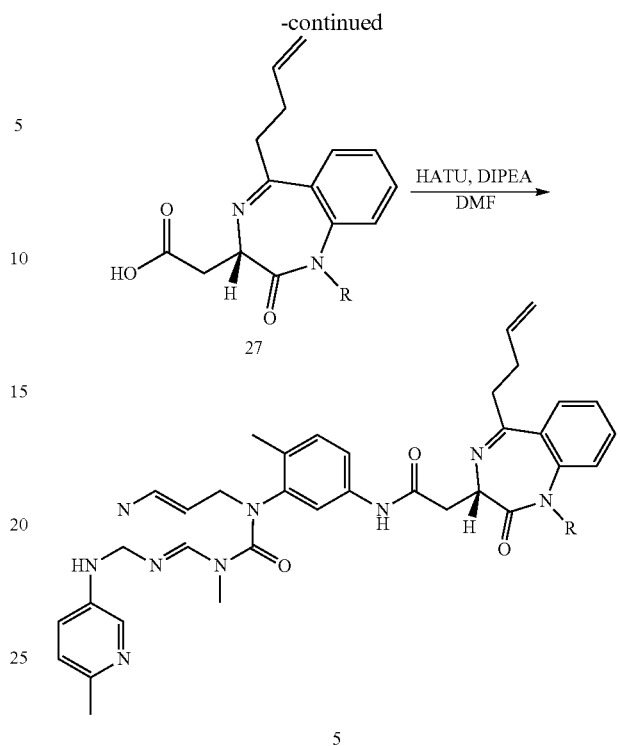

Aniline 25 (1.0 eq.) and carboxylic acid 27 (1.0 eq.) (benzodiazepine 27 derivatives were synthesized in accordance with the following reference: Org. Lett. 2015, 17, 3592-3595) were charged in a round-bottom flask and were dissolved in dimethylformamide (0.2 M). Then, HATU (2.0 eq.) and N,N-diisopropylethylamine (10.0 eq.) were added thereto and stirred for one day. When the reaction was completed, the resulting product was extracted with dichloromethane and an aqueous sodium hydrogen carbonate solution. The collected organic layer was washed several times with water, dried over anhydrous magnesium sulfate and filtered, and the obtained residue was purified by column chromatography (dichloromethane:methanol=20:1→10:1) to obtain amide 5 (yield of 10 to 20%).

Example 44

(S)-2-(5-(but-3-en-1-yl)-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide

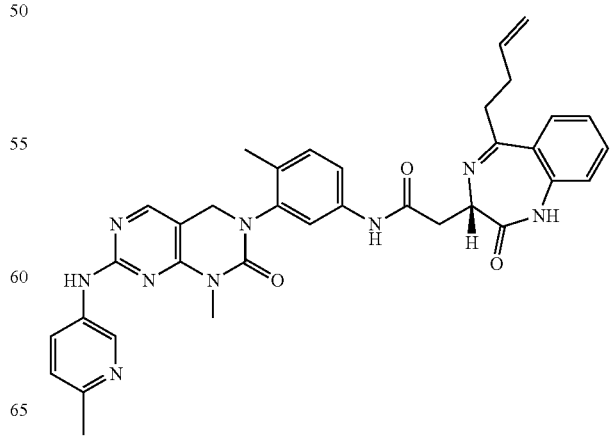

LRMS (MM:ESI-APCI+) m/z calc'd for $C_{35}H_{36}N_9O_3$ [M+H]$^+$:630; found:630.

Example 45

(S)-2-(5-(but-3-en-1-yl)-1-methyl-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide

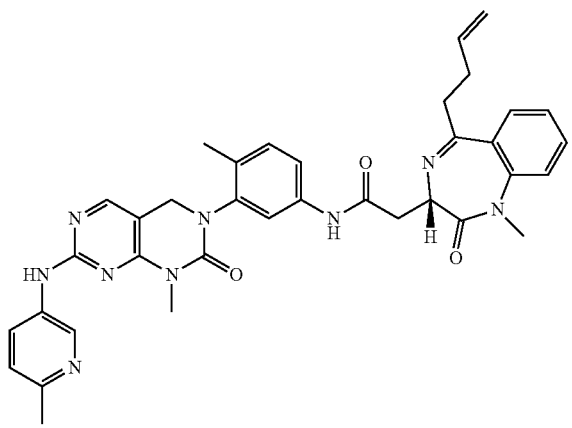 [SMILES: C=CCCC1=N[C@@H](CC(=O)Nc2ccc(C)c(N3Cc4cnc(Nc5ccc(C)nc5)nc4N(C)C3=O)c2)C(=O)N(C)c2ccccc21]

$^1$H NMR (600 MHz, DMSO) δ 10.18 (s, 1H), 9.69 (s, 1H), 8.83 (s, 1H), 8.13 (s, 1H), 8.08 (d, J=8.5 Hz, 1H), 7.71 (d, J=7.8 Hz, 1H), 7.67 (d, J=14.5 Hz, 1H), 7.60 (t, J=7.9 Hz, 1H), 7.50 (d, J=8.4 Hz, 1H), 7.32 (t, J=8.2 Hz, 2H), 7.22 (dd, J=14.1, 8.4 Hz, 2H), 5.67 (dt, J=16.6, 8.4 Hz, 1H), 4.84 (d, J=13.6 Hz, 2H), 4.63 (d, J=14.0 Hz, 1H), 4.47 (d, J=14.1 Hz, 1H), 3.90 (d, J=7.2 Hz, 1H), 3.31 (s, 3H), 3.25 (s, 3H), 3.12 (td, J=15.8, 6.9 Hz, 1H), 2.97 (ddt, J=30.1, 14.6, 7.4 Hz, 2H), 2.75 (dt, J=15.4, 7.9 Hz, 1H), 2.42 (s, 3H), 2.21 (m, 1H), 2.14 (m, 1H), 2.08 (s, 3H); $^{13}$C NMR (151 MHz, DMSO) δ 170.61, 169.82, 169.67, 159.18, 157.39, 153.53, 152.39, 150.08, 142.17, 141.47, 138.45, 137.66, 131.59, 131.07, 130.00, 129.83, 127.62, 127.32, 124.88, 123.29, 122.25, 118.45, 118.04, 115.54, 103.48, 59.82, 46.92, 39.00, 36.78, 34.93, 31.22, 31.20, 28.58, 23.16, 18.45, 17.04; HRMS (MM: ESI-APCI+) m/z calc'd for $C_{36}H_{38}N_9O_3$ [M+H]$^+$:644.3098; found:644.3099.

Example 46

(S)-2-(1-benzyl-5-(but-3-en-1-yl)-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide

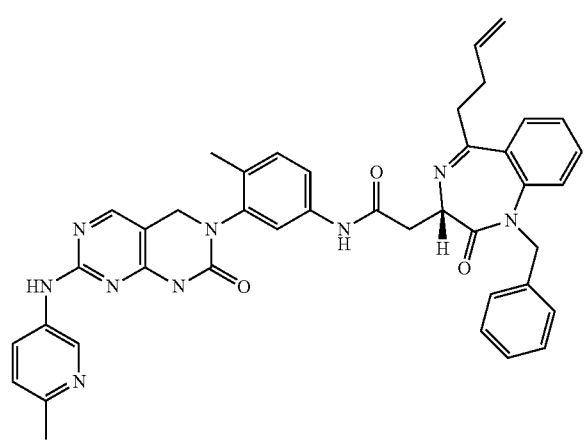 [SMILES: C=CCCC1=N[C@@H](CC(=O)Nc2ccc(C)c(N3Cc4cnc(Nc5ccc(C)nc5)nc4NC3=O)c2)C(=O)N(Cc2ccccc2)c2ccccc21]

$^1$H NMR (400 MHz, DMSO) δ 10.20 (s, 1H), 9.63 (s, 1H), 8.79 (d, J=2.6 Hz, 1H), 8.13 (d, J=1.7 Hz, 1H), 8.05 (dd, J=8.4, 2.7 Hz, 1H), 7.72-7.62 (m, 2H), 7.62-7.48 (m, 2H), 7.34 (td, J=8.3, 2.2 Hz, 1H), 7.27 (t, J=7.4 Hz, 1H), 7.24-7.13 (m, 5H), 7.03 (d, J=7.3 Hz, 2H), 5.79-5.66 (m, 1H), 5.33 (dd, J=15.7, 3.8 Hz, 1H), 4.97-4.85 (m, 3H), 4.63 (d, J=14.1 Hz, 1H), 4.48 (d, J=14.1 Hz, 1H), 4.02 (t, J=7.1 Hz, 1H), 3.34 (s, 3H), 3.22 (ddd, J=16.8, 9.9, 7.4 Hz, 1H), 3.10-2.99 (m, 1H), 2.79-2.70 (m, 2H), 2.40 (s, 3H), 2.09 (s, 3H), 1.98 (q, J=7.5 Hz, 2H), $^{13}$C NMR (101 MHz, DMSO) δ 170.79, 169.79, 169.35, 169.33, 159.41, 157.50, 153.66, 152.53, 150.67, 141.62, 140.53, 140.51, 138.54, 138.04, 137.62, 135.18, 131.66, 131.18, 131.14, 130.15, 128.79, 127.72, 127.61, 127.56, 126.69, 125.49, 122.98, 122.91, 118.63, 118.27, 115.55, 103.42, 59.96, 49.63, 47.06, 39.01, 36.96, 31.09, 31.07, 28.67, 23.70, 17.16; HRMS (MM: ESI-APCI+) m/z calc'd for $C_{42}H_{42}N_9O_3$[M+H]$^+$:720.3411, found:720.3410.

Preparation Example 4

The process for preparing the compounds of Examples 47 and 48 is given below:

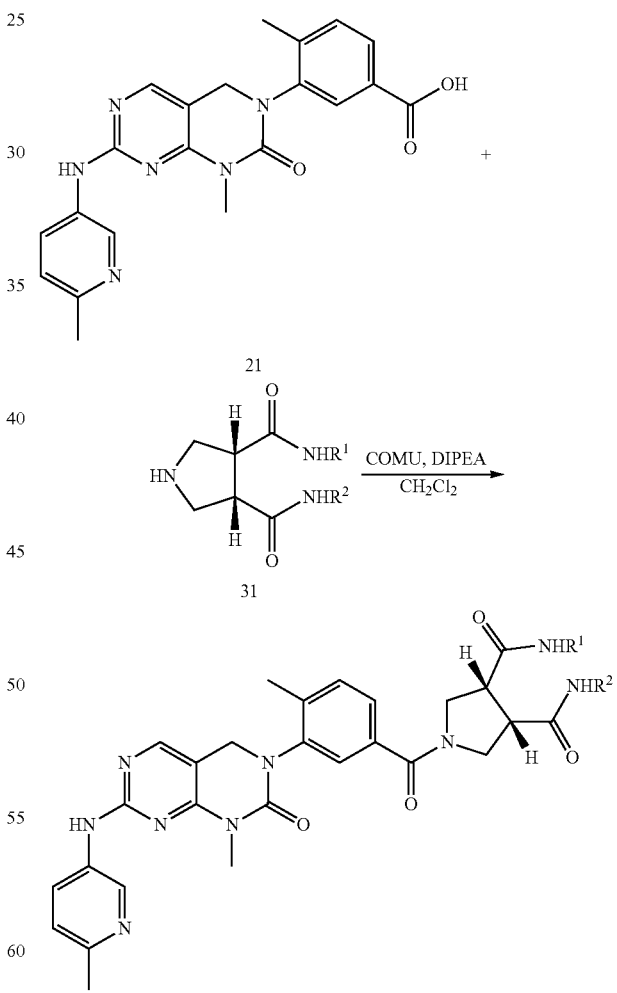

Benzoic acid 21 (1.0 eq.) and amine 31 (1.0 eq.) (amine 31 derivatives were synthesized in accordance with the following reference: *J. Am. Chem. Soc.* 2011, 133, 10184-

10194) were charged in a round-bottom flask and were dissolved in dimethylformamide (0.2 M). Then, COMU (1.2 eq.) and N,N-diisopropylethylamine (2.5 eq.) were added thereto and stirred for one day. When the reaction was completed, the resulting product was extracted with dichloromethane and an aqueous sodium hydrogen carbonate solution. The collected organic layer was washed several times with water, dried over anhydrous magnesium sulfate and filtered, and the obtained residue was purified by column chromatography (dichloromethane:methanol=20:1→10:1) to obtain amide 8 (yield of 10 to 42%).

Example 47

(3S,4S)—$N^3$-benzyl-$N^4$-(4-chlorobenzyl)-1-(4-methyl-3-(1-methyl-7-((6-methylpyridin-3-yl)amino)-2-oxo-1,4-dihydropyrimido[4,5-d]pyrimidin-3(2H)-yl)benzo yl)pyrrolidine-3,4-dicarboxamide

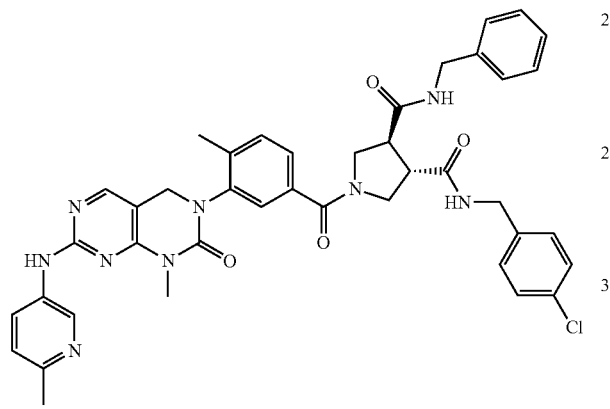

LRMS (MM:ESI-APCI+) m/z calc'd for $C_{41}H_{41}ClN_9O_4$ [M+H]$^+$:758; found:758.

Example 48

(3S,4S)—$N^3$-(2-(1H-indol-3-yl)ethyl)-$N^4$-(4-chlorobenzyl)-1-(4-methyl-3-(1-m ethyl-7-((6-methylpyridin-3-yl)amino)-2-oxo-1,4-dihydropyrimido[4,5-d]pyrimidin-3(2H)-yl)benzoyl)pyrrolidine-3,4-dicarboxamide

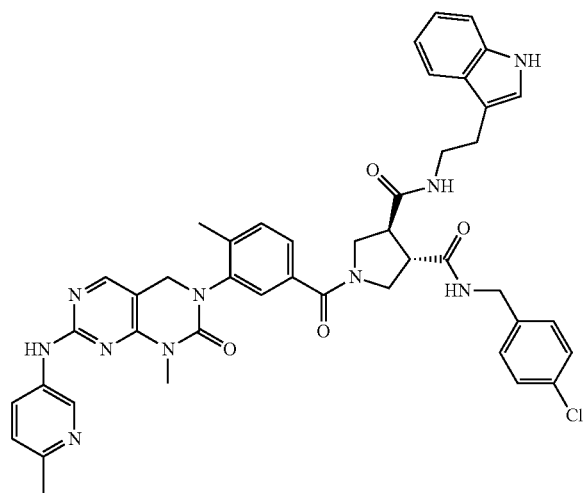 [SMILES: Cc1ccc(Nc2ncc3c(n2)N(C)C(=O)N(c2cc(C(=O)N4C[C@@H](C(=O)NCCc5c[nH]c6ccccc56)[C@H](C(=O)NCc5ccc(Cl)cc5)C4)ccc2C)C3)cn1]

LRMS (MM:ESI-APCI+) m/z calc'd for $C_{44}H_{44}ClN_{10}O_4$ [M+H]$^+$:811; found:811.

Preparation Example 5

The process for preparing the compounds of Examples 49 to 51 is given below:

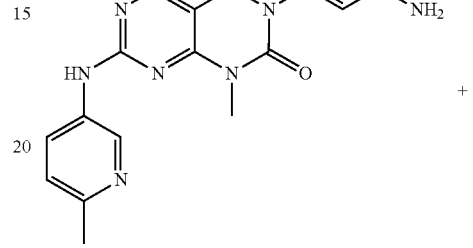

25

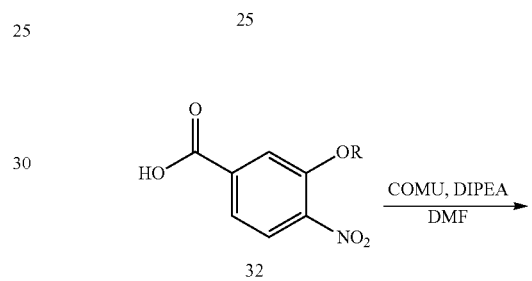

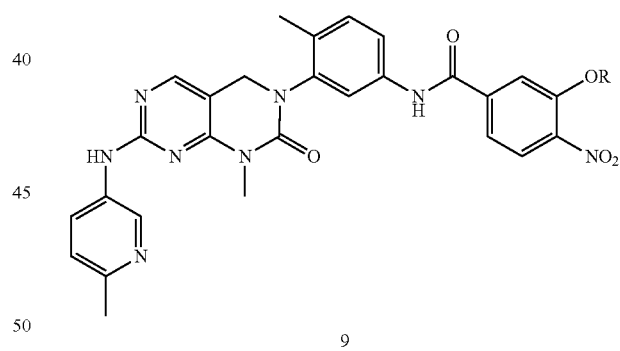

9

Aniline 25 (1.0 eq.) and benzoic acid 32 (1.0 eq.) (benzoic acid 32 derivatives were synthesized in accordance with the following reference: *J. Am. Chem. Soc.* 2009, 131, 5564-5572) were charged in a round-bottom flask and were dissolved in dimethylformamide (0.2 M). Then, COMU (2.0 eq.) and N,N-diisopropylethylamine (5.0 eq.) were added thereto and stirred for one day. When the reaction was completed, the resulting product was extracted with dichloromethane and an aqueous sodium hydrogen carbonate solution. The collected organic layer was washed several times with water, dried over anhydrous magnesium sulfate, and filtered, and the obtained residue was purified by column chromatography (dichloromethane:methanol=20:1→10:1) to obtain amide 9 (yield of 10 to 54%).

Example 49

3-isobutoxy-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide

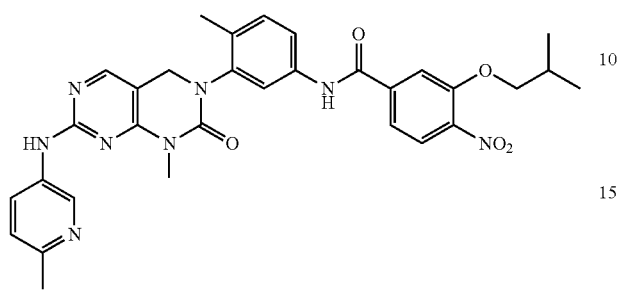

LRMS (MM:ESI-APCI+) m/z calc'd for $C_{31}H_{32}N_8O_5Na$ [M+Na]$^+$:619; found:619.

Example 50

3-(2-(1H-indol-3-yl)ethoxy)-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide

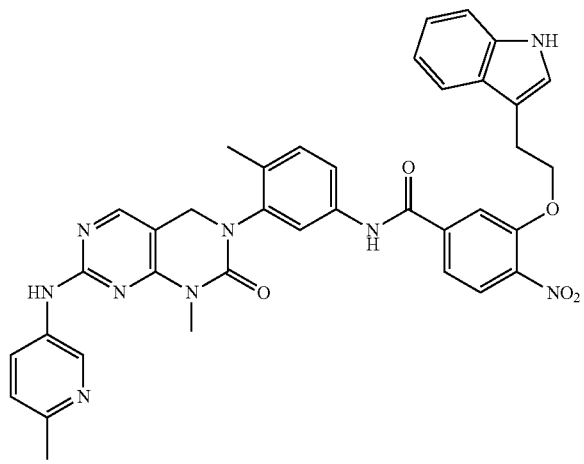 [SMILES: Cc1ccc(Nc2ncc3c(n2)N(C)C(=O)N(c2cc(NC(=O)c4ccc([N+](=O)[O-])c(OCCc5c[nH]c6ccccc56)c4)ccc2C)C3)cn1]

LRMS (MM:ESI-APCI+) m/z calc'd for $C_{37}H_{34}N_9O_5$ [M+H]$^+$:684; found:684.

Example 51

3-(4-methoxyphenethoxy)-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide

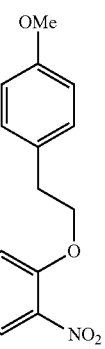

LRMS (MM:ESI-APCI+) m/z calc'd for $C_{36}H_{34}N_8O_6Na$ [M+Na]$^+$:697; found:697.

Preparation Example 6

The process for preparing the compounds of Examples 52 to 56 is given below:

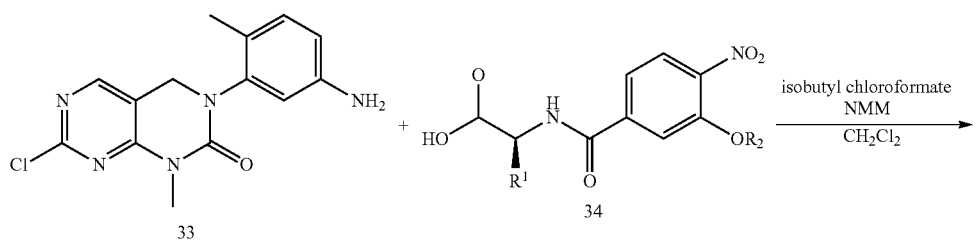

-continued

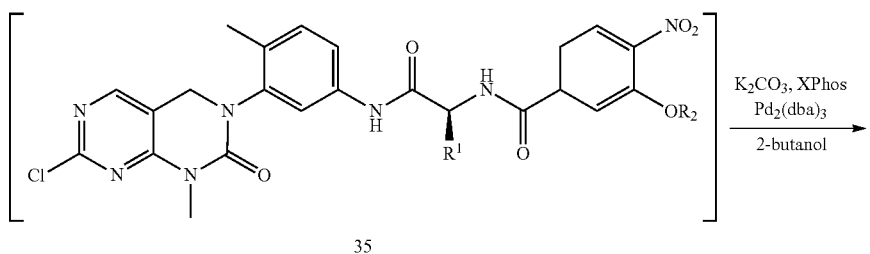

35

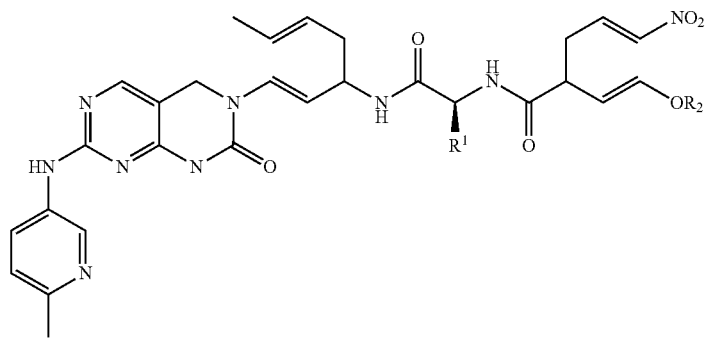

10

Acid 34 (1.5 eq.) (acid 34 derivatives were synthesized in accordance with the following reference: *J. Am. Chem. Soc.* 2009, 131, 5564-5572) and NMM (1.6 eq.) were charged in a round-bottom flask and dissolved in dimethylformamide (0.1 M). Then, isobutyl chloroformate (1.6 eq.) was slowly added thereto at 0° C. After stirring at 0° C. for 30 minutes, aniline 33 was added and refluxed for 20 hours. After the reaction was stopped with an aqueous ammonium chloride solution, the resulting product was extracted with ethyl acetate and water. The collected organic layer was washed several times with water, dried over anhydrous magnesium sulfate and filtered, and the obtained residue was purified by column chromatography (dichloromethane:methanol=20:1→10:1) to obtain amide 35 (yield of 70 to 84%).

Amide 35 (1.0 eq.), potassium carbonate (5.0 eq.), 5-amino-2-methylpyridine (1.01 eq.), XPhos (0.2 eq.) and Pd$_2$(dba)$_3$ (0.2 eq.) were charged in a round-bottom flask and were dissolved in 2-butanol (0.2 M). Then, the resulting solution was stirred at 100° C. for 2 hours and then cooled to room temperature. After filtration, the solvent was concentrated under reduced pressure and purified by column chromatography (dichloromethane:methanol=20:1→10:1) to obtain amide 10 (yield of 61 to 85%).

Example 52

3-isobutoxy-N-(2-((4-methyl-3-(1-methyl-7-((6-methylpyridin-3-yl)amino)-2-oxo-1,4-dihydropyrimido[4,5-d]pyrimidin-3(2H)-yl)phenyl)amino)-2-oxoethyl)-4-nitrobenzamide

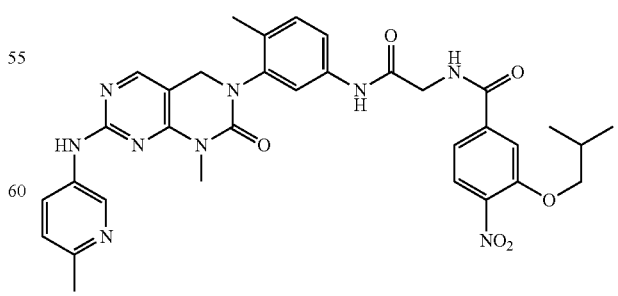

LRMS (MM:ESI-APCI+) m/z calc'd for $C_{33}H_{36}N_9O_6$ [M+H]$^+$:654; found:654.

Example 53

(S)-3-isobutoxy-N-(1-((4-methyl-3-(1-methyl-7-((6-methylpyridin-3-yl)amino)-2-oxo-1,4-dihydropyrimido[4,5-d]pyrimidin-3(2H)-yl)phenyl)amino)-2-oxopropan-2-yl)-4-nitrobenzamide

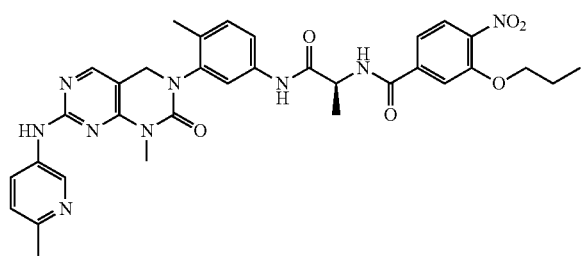 [SMILES: CCCOc1cc(C(=O)N[C@@H](C)C(=O)Nc2ccc(C)c(N3Cc4cnc(Nc5ccc(C)nc5)nc4N(C)C3=O)c2)ccc1[N+](=O)[O-]]

LRMS (MM:ESI-APCI+) m/z calc'd for $C_{34}H_{38}N_9O_6$ [M+H]$^+$:668; found:668.

Example 54

(S)-3-isobutoxy-N-(4-methyl-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopentan-2-yl)-4-nitrobenzamide

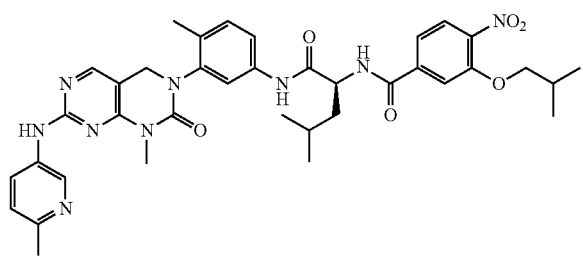 [SMILES: Cc1ccc(Nc2ncc3c(n2)N(C)C(=O)N(c2cc(NC(=O)[C@H](CC(C)C)NC(=O)c4ccc([N+](=O)[O-])c(OCC(C)C)c4)ccc2C)C3)cn1]

LRMS (MM:ESI-APCI+) m/z calc'd for $C_{37}H_{43}N_9O_6Na$ [M+Na]$^+$:732; found:732.

Example 55

(S)—N-3-(1H-indol-3-yl)-1-((4-methyl-3-(1-methyl-7-((6-methylpyridin-3-yl) amino)-2-oxo-1,4-dihydropyrimido[4,5-d]pyrimidin-3(2H)-yl)phenyl) amino)-1-oxopropan-2-yl)-3-isobutoxy-4-nitrobenzamide

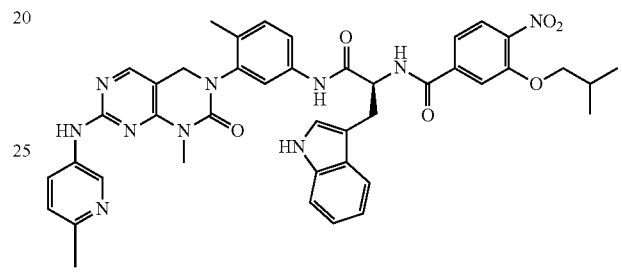

LRMS (MM:ESI-APCI+) m/z calc'd for $C_{42}H_{43}N_{10}O_6$ [M+H]$^+$:783; found:783.

Example 56

(S)-3-(4-methoxyphenethoxy)-N-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopropan-2-yl)-4-nitrobenzamide LRMS (MM:ESI-APCI+) m/z calc'd for $C_{39}H_{40}N_9O_7$ [M+H]$^+$:746; found:746.

Preparation Example 7

The process for preparing the compound of Example 57 is given below:

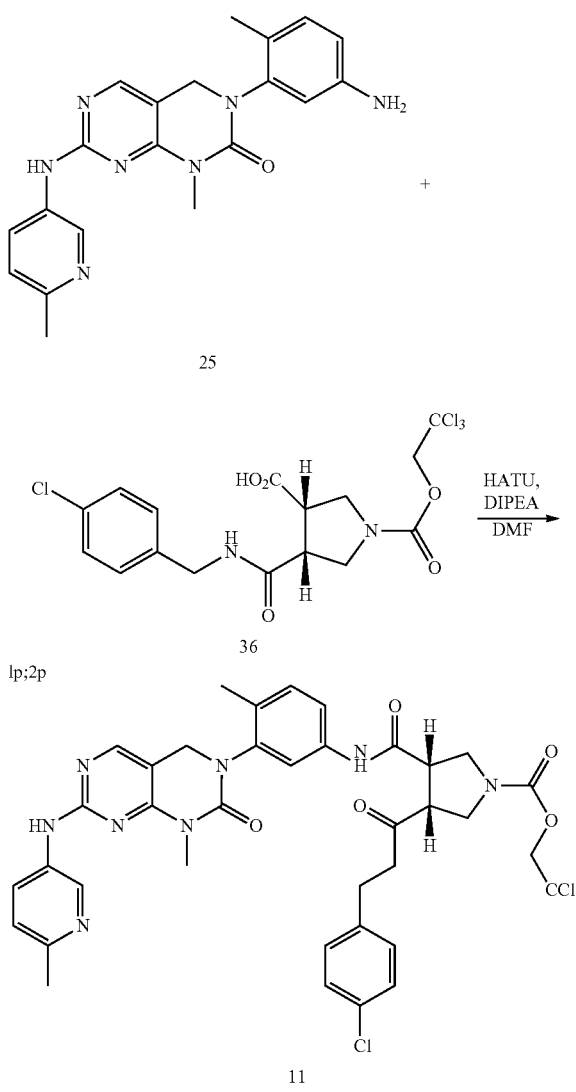

Aniline 25 (1.0 eq.) and acid 36 (1.0 eq.) (acid 36 derivatives were synthesized in accordance with the following reference: *J. Am. Chem. Soc.* 2009, 131, 5564-5572) were charged in a round-bottom flask and were dissolved in dimethylformamide (0.1 M). Then, HATU (2.0 eq.) and N,N-diisopropylethylamine (5.0 eq.) were added thereto and stirred for one day. When the reaction was completed, the resulting product was extracted with dichloromethane and an aqueous sodium hydrogen carbonate solution. The collected organic layer was washed several times with water, dried over anhydrous magnesium sulfate and filtered, and the obtained residue was purified by column chromatography (dichloromethane:methanol=20:1→10:1) to obtain amide 11 (yield of 47%).

Example 57: 2,2,2-trichloroethyl (3S,4S)-3-((4-chlorobenzyl)carbamoyl)-4-((4-methyl-3-(1-methyl-7-((6-methylpyridin-3-yl)amino)-2-oxo-1,4-dihydropyrimido[4,5-d]pyrimidin-3(2H)-yl)phenyl)carbamoyl)pyrrolidine-1-carboxylate

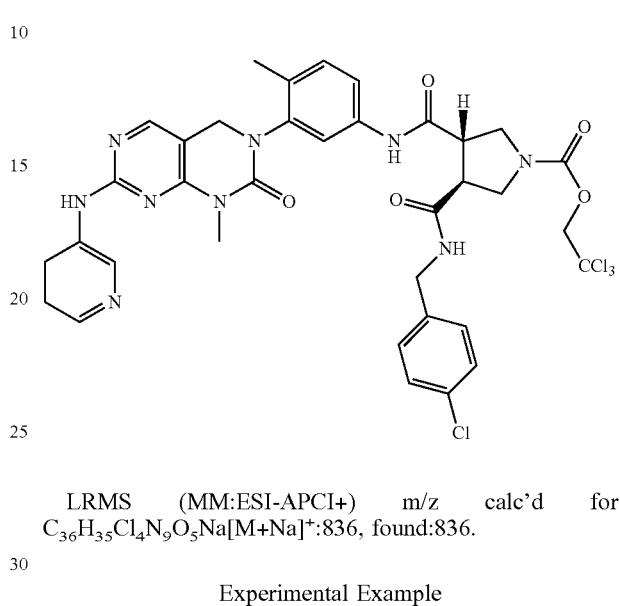

LRMS (MM:ESI-APCI+) m/z calc'd for $C_{36}H_{35}Cl_4N_9O_5Na[M+Na]^+$:836, found:836.

Experimental Example

Experimental Example 1. Measurement of Kinase Inhibitory Activity

In order to measure the inhibitory activity (% inhibitory capacity) against protein kinases of the compounds of the present invention, biochemical assays were performed using a full kinase panel.

The experimental compounds used herein were the compounds of Compound Nos. 1 and 33. The residual enzyme activity (%) was calculated by measuring the inhibitory activity against kinases upon treatment with the experimental compound at a single concentration of 1 μM. Kinases having calculated residual enzyme activity (%) of 30% or less (that is, inhibition of 70% or more) are shown below.

<Kinases Having Inhibitory Activity of 70% or More>

LCK, DDR1, FGR, BMX, ABL2, BLX, BLK, LYN, DDR2, RAF1, c-Src, CSK, HCK

Experimental Example 2. Inhibitory Activity Against LCK, c-Src, p38a/MAPK14, ABL1, DDR1 and FGR Kinases $IC_{50}$ values were calculated by measuring the inhibitory activity against LCK, c-Src, p38a/MAPK14, ABL1, DDR1 and FGR kinases of the compounds of the present invention. The calculated $IC_{50}$ values are shown in Tables 1 to 3 below:

$IC_{50}$ activity

A=1 to 200 nM

B=200 to 400 nM

C=400 to 600 nM

D=>600 nM

TABLE 1

| | LCK | c-Src | p38a/MAPK14 | ABL1 | ABL1 (T315I) | DDR1 | FGR |
|---|---|---|---|---|---|---|---|
| Example 1 | A | D | D | B | D | A | A |
| Example 2 | A | B | D | B | D | — | — |
| Example 3 | A | D | — | — | — | — | — |
| Example 4 | A | B | — | — | — | — | — |
| Example 5 | A | D | — | — | — | — | — |
| Example 6 | A | D | — | — | — | — | — |
| Example 7 | A | C | — | — | — | — | — |
| Example 8 | C | D | — | — | — | — | — |
| Example 9 | A | D | — | — | — | — | — |
| Example 10 | B | D | — | — | — | — | — |
| Example 11 | A | A | — | — | — | — | — |
| Example 12 | A | D | — | — | — | — | — |
| Example 13 | A | C | — | — | — | — | — |
| Example 14 | A | D | — | — | — | — | — |
| Example 15 | B | D | — | A | — | — | — |
| Example 16 | A | B | — | A | — | — | — |
| Example 17 | A | B | — | A | — | — | — |
| Example 18 | B | C | — | A | — | — | — |
| Example 19 | A | C | — | B | — | — | — |
| Example 20 | A | A | — | A | — | — | — |
| Example 21 | A | C | — | A | — | — | — |
| Example 22 | D | D | — | — | — | — | — |
| Example 23 | D | D | — | — | — | — | — |
| Example 24 | A | D | — | — | — | — | — |
| Example 25 | B | D | — | — | — | — | — |

TABLE 2

| | LYN | LCK | c-Src | p38a/MAPK14 | ABL1 | ABL1 (T315I) | DDR1 | FGR |
|---|---|---|---|---|---|---|---|---|
| Example 26 | — | A | A | D | A | D | — | — |
| Example 27 | — | A | A | — | — | — | — | — |
| Example 28 | — | A | A | — | — | — | — | — |
| Example 29 | — | A | A | — | — | — | — | — |
| Example 30 | — | A | A | A | A | D | — | — |
| Example 31 | A | A | A | A | A | D | — | — |
| Example 32 | — | A | A | B | A | D | — | — |
| Example 33 | A | A | C | D | C | D | A | A |
| Example 34 | A | A | A | — | — | — | — | — |
| Example 35 | A | A | A | — | — | — | — | — |
| Example 36 | — | A | A | — | — | — | — | — |
| Example 37 | A | A | A | — | — | — | — | — |
| Example 38 | A | A | B | — | — | — | — | — |
| Example 39 | — | A | C | — | — | — | — | — |
| Example 40 | — | A | A | — | — | — | — | — |
| Example 41 | — | A | A | — | — | — | — | — |
| Example 42 | — | A | A | — | — | — | — | — |
| Example 43 | — | A | A | — | — | — | — | — |
| Example 44 | — | A | A | — | — | — | — | — |
| Example 45 | — | A | A | — | — | — | — | — |
| Example 46 | — | A | A | — | — | — | — | — |

TABLE 3

| | LCK | c-Src | p38a/MAPK14 | ABL1 | ABL1 (T315I) |
|---|---|---|---|---|---|
| Example 47 | A | A | A | A | — |
| Example 48 | A | A | C | A | — |
| Example 49 | A | — | A | A | D |
| Example 50 | A | — | B | A | — |
| Example 51 | A | — | A | A | — |
| Example 52 | A | — | C | A | D |
| Example 53 | C | — | D | D | — |
| Example 54 | A | — | D | A | D |
| Example 55 | D | — | — | D | — |
| Example 56 | A | — | D | A | — |
| Example 57 | A | A | A | A | — |

Formulation Example

Meanwhile, the novel compound represented by any one of Formulae 1 to 6 according to the present invention can be formulated in various forms according to the purpose thereof. Examples of some formulation methods including incorporation of the compound represented by any one of Formulae 1 to 6 according to the present invention as an active ingredient are as follows, but the present invention is not limited thereto.

Formulation Example 1: Tablet (Direct Pressing)

5.0 mg of the active ingredient was sieved, and 14.1 mg of lactose, 0.8 mg of crospovidone USNF and 0.1 mg of magnesium stearate were mixed therewith, and the mixture was pressed into tablets.

Formulation Example 2: Tablet (Wet Granulation)

5.0 mg of the active ingredient was sieved and was mixed with 16.0 mg of lactose and 4.0 mg of starch. 0.3 mg of Polysorbate 80 was dissolved in pure water, and an appropriate amount of the resulting solution was added to the mixture, followed by granulation. The granules were dried, sieved and mixed with 2.7 mg of colloidal silicon dioxide and 2.0 mg of magnesium stearate. The granules were pressed into tablets.

Formulation Example 3. Powders and Capsules 5.0 mg of the active ingredient was sieved and then mixed with 14.8 mg of lactose, 10.0 mg of polyvinylpyrrolidone and 0.2 mg of magnesium stearate. Hard No. 5 gelatin capsules were filled with the resulting mixture using an appropriate device.

Formulation Example 4. Injection

Injections were prepared by incorporating 100 mg of the active ingredient as well as 180 mg of mannitol, 26 mg of $Na_2HPO_4 \cdot 12H_2O$ and 2,974 mg of distilled water.

As is apparent from the foregoing, the compound according to the present invention has excellent ability to inhibit the activity of protein kinases such as ABL1, ABL2/ARG, ARAF, BLK, BMX/ETK, BRAF, c-Src, CSK, DDR1, DDR2, EPHA2, EPHA4, ERBB4/HER2, ERBB4/HER4, EPHB1, FGR, FRK/PTK5, FYN, FGFR1, FMS, HCK, LCK, LIMK1, LYN, LYN B, MEK5, MLK1/MAP3K9, MLK3/MAP3K11, P38a/MAPK14, PDGFRa, PDGFRb, PEAK1, RAF1, YES/YES1, ARK5/NUAK1, Aurora C, BMPR2, BRSK2, BTK, c-Kit, CAMK1b, CAMK1d, CAMKK2, CK1d, CK2a, CK2a2, CLK1, CLK3, CTK/MATK, DAPK1, DYRK1/DYRK1A, DYRK1B, DYRK3, EGRF, EPHA2, EPHA3, EPHA4, EPHA5, EPHA8, EPHB1, EPHA3, EPHA5, EPHA8, EPHB2, EPHB4, ERBB2/HER2, ERK1, ERN1/IRE1, FLT4/VEGFR3, GRK4, HIPK3, IKKa/CHUK, IRAK1, KDR/VEGFR2, KHS/MAP4K5, MAPKAPK5/PRAK, MASTL, MEK2, MEKK3, MKK6, MLK1/MAP3K9, MLK2/MAP3K10, MLK3/MAP3K11, MSK1/RPS6KA5, MSK2/RPS6KA4, MSSK1/STK23, MST4, MUSK, NEK11, NEK8, p38b/MAPK11, PAK5, PKCd, PKCeta, PKCG, PKMYT1, PKN3/PRK3, PLK3, PYK2, RET, RIPK4, RON/MST1R, ROS/ROS1, SIK1, ZAK/MLTK, WNK3, WNK2, TRKC, STK32B/YANK2, SNRK, SLK/STK2, SIK3, RSK1, ROCK1, PKG2/PRKG2, MRCKa/CDC42BPA, LIMK2, JAK2, JAK1, ITK, IRAK1, GSK3a, GCK/MAP4K2, FGFR2, FGFR1, FES/FPS, c-MET, c-Kit, ARAF, ALK6/BMPR1B, ALK1/ACVRL1 and AKT3. Therefore, the compound of the present invention may be used for treating, preventing and alleviating cancer-related diseases caused by abnormal cell growth.

The compound according to the present invention, a pharmaceutically acceptable salt thereof, a hydrate thereof, a stereoisomer thereof and a pharmaceutical composition for preventing or treating cancer containing the same, as an active ingredient, exhibits low cytotoxicity, and excellent inhibitory activity and anti-proliferative activity selective for cancer cells, thus being useful for the prevention or treatment of cancer.

Examples of cancer-related diseases that can be prevented, treated or alleviated through treatment with the compound of the present invention include stomach cancer, lung cancer, liver cancer, colorectal cancer, small intestine cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, kidney cancer, sarcoma, prostate cancer, urethral cancer, bladder cancer, blood cancer (including leukemia, multiple myeloma, and myelodysplastic syndrome), lymphoma (including Hodgkin's disease and non-Hodgkin's lymphoma), psoriasis, fibroadenomas and the like.

In particular, the compound according to the present invention has excellent inhibitory activity selective against LCK kinase, thus being effective for the treatment of cancer-associated diseases requiring LCK kinase inhibition.

Although embodiments of the present invention have been described above, it will be obvious to those skilled in the art that the present invention can be implemented in other specific embodiments without changing the technical concepts or essential features of the present invention. Therefore, it should be construed that the aforementioned embodiments are illustrative and not restrictive in all respects.

What is claimed is:

1. A compound selected from a pyrimido[4,5-d]pyrimidin-2-one derivative compound represented by any one of the following Formulae 1 to 6, a pharmaceutically acceptable salt thereof, a hydrate thereof and a stereoisomer thereof:

[Formula 1]
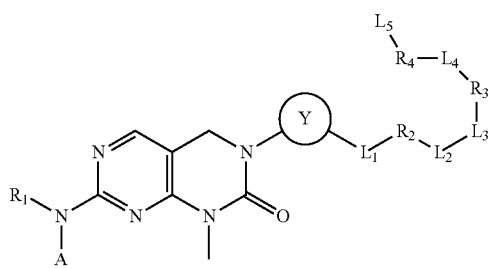

[Formula 2]
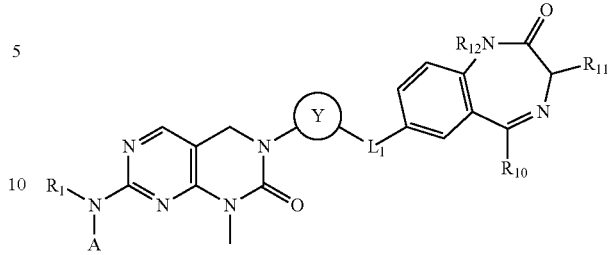

[Formula 3]
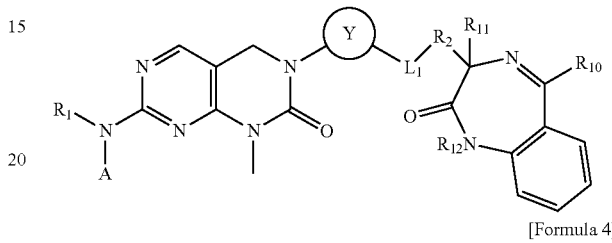

[Formula 4]
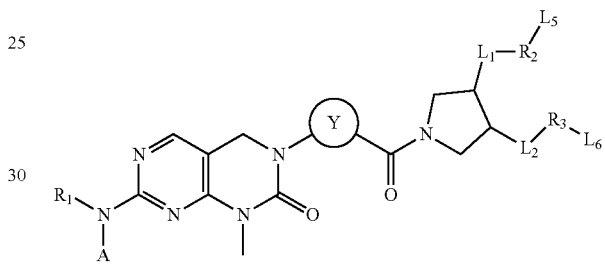

[Formula 5]
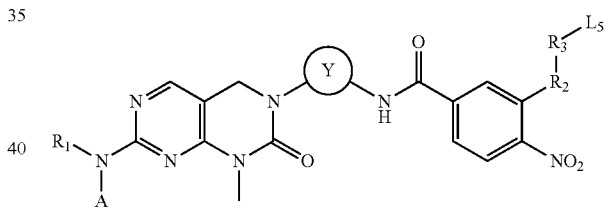

[Formula 6]
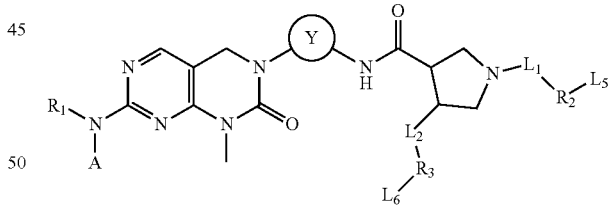

wherein $R_1$ is hydrogen; a $C_1$-$C_{13}$ alkyl group; a $C_3$-$C_{10}$ cyclic group; or a $C_3$-$C_{10}$ heterocyclic group;

A is hydrogen; a $C_1$-$C_{13}$ alkyl group; a $C_6$-$C_{10}$ aryl group; a $C_3$-$C_{10}$ cyclic group; a $C_3$-$C_{10}$ heteroaryl group; a $C_3$-$C_{10}$ heterocyclic group; or —C(O)—$C_1$-$C_{13}$ alkyl);

Y is a $C_6$-$C_{10}$ aryl group; or a 5-membered to 9-membered heteroaryl group containing one to four heteroatoms selected from nitrogen (N), oxygen (O) and sulfur (S) atoms;

$L_1$, $L_2$, $L_3$ and $L_4$ are each independently selected from the group consisting of —$NR_5$—; —$NR_5CH_2$—; —$NR_5CO$)—; —C(O)$NR_5$—; —$NR_5C(O)NR_5$—;

—S(O)$_2$—; —NR$_5$S(O)$_2$—; —S(O)$_2$NR$_5$—; —O—; —CH$_2$—; —CH(CH$_3$)—; —C(O)O—; —C(O)—;

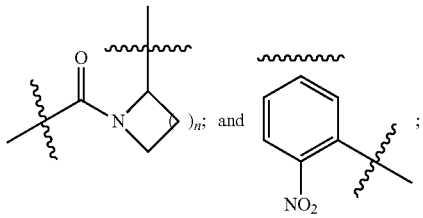

L$_5$ and L$_6$ are each independently —C(O)NR$_5$R$_6$; —CR$_5$R$_6$R$_7$; —OR$_5$; —CCl$_3$; a C$_1$-C$_6$ alkyl group; a C$_3$-C$_{10}$ cyclic group; -substituted or unsubstituted benzene; -substituted or unsubstituted indole; -substituted or unsubstituted phenyl; -substituted or unsubstituted hexane; -substituted or unsubstituted furan; -substituted or unsubstituted thiophene; -substituted or unsubstituted pyridine; -substituted or unsubstituted benzofuran; -substituted or unsubstituted naphthalene; -substituted or unsubstituted anthracene; or -substituted or unsubstituted phenathrene;

R$_2$, R$_3$ and R$_4$ are each independently —O—; —CH$_2$—; —CH(CH$_3$)—; —CR$_5$R$_6$—; —NR$_5$—; —NR$_5$CH$_2$—; —NR$_5$C(O)—, —C(O)NR$_5$—; —NR$_5$C(O)NR$_5$—; —S(O)$_2$—; —NR$_5$S(O)$_2$—; or —C$_3$-C$_{10}$ cyclic group-;

R$_5$, R$_6$ and R$_7$ are each independently hydrogen; halogen; a C$_1$-C$_6$ alkyl group; a C$_3$-C$_{10}$ cyclic group; a C$_6$-C$_{10}$ aryl group; or —CH$_2$(Ph);

R$_{10}$, R$_{11}$ and R$_{12}$ are each independently hydrogen; a C$_1$-C$_{13}$ alkyl group; a C$_6$-C$_{10}$ aryl group; a C$_3$-C$_{10}$ cyclic group; a C$_3$-C$_{10}$ heteroaryl group; a C$_3$-C$_{10}$ heterocyclic group; —C(O)—(C$_1$-C$_{13}$ alkyl); —CH$_2$(Ph), —CH$_2$(Ph)R$_5$; a benzyl group; or —CH$_2$CH=CH$_2$; and N is 0, 1, 2, 3 or 4, wherein the C$_1$-C$_6$ alkyl group, C$_1$-C$_{13}$ alkyl group or C$_3$-C$_{10}$ cyclic group includes at least one substituent selected from the group consisting of hydrogen; a hydroxy group; a halogen group; a C$_1$-C$_{13}$ alkyl group; a C$_1$-C$_6$ alkoxy group; an amino group (—NR$_8$R$_9$); a nitro group (—N(O)$_2$); an amide group (—(C=O)NR$_8$R$_9$); a carboxylic group (—C(O)OH), a nitrile group (—CN), a urea group (—NR$_8$(C=O)NR$_9$—); a sulfonamide group (—NHS(O)$_2$—); a sulfide group (—S—); a sulfone group (—S(O)$_2$—); a phosphoryl group (—P(O)R$_8$R$_9$); a C$_6$-C$_{10}$ aryl group; a C$_3$-C$_{10}$ heteroaryl group; and a C$_3$-C$_{10}$ heterocyclic group, the C$_6$-C$_{10}$ aryl group, C$_3$-C$_{10}$ heteroaryl group or C$_3$-C$_{10}$ heterocyclic group includes at least one substituent selected from the group consisting of hydrogen; a hydroxy group; a halogen group; a carbonyl group (—(C=O)R$_8$R$_9$); a C$_1$-C$_3$ alkyl group substituted or unsubstituted with halogen or a C$_3$-C$_{10}$ heterocyclic group; a C$_1$-C$_3$ alkoxy group substituted or unsubstituted with halogen or a C$_3$-C$_{10}$ heterocyclic group; C$_6$-C$_{10}$ phenoxy; an amino group (—NR$_8$R$_9$); a nitro group (—N(O)$_2$); an amide group (—(C=O)NR$_8$R$_9$); a carboxylic group (—C(O)OH), a nitrile group (—CN), a urea group (—NR$_8$(C=O)NR$_9$—); a sulfonamide group (—NHS(O)$_2$—); a sulfide group (—S—); a sulfone group (—S(O)$_2$—); a phosphoryl group (—P(O)R$_8$R$_9$); a C$_6$-C$_{10}$ aryl group; a C$_3$-C$_{10}$ heteroaryl group; and a C$_3$-C$_{10}$ heterocyclic group, R$_8$ and R$_9$ described above include at least one selected from the group consisting of hydrogen; a C$_1$-C$_6$ alkyl group; a C$_1$-C$_6$ alkenyl group; a C$_1$-C$_6$ alkynyl group; a C$_6$-C$_{10}$ aryl group; a C$_3$-C$_{10}$ heteroaryl group; and a C$_3$-C$_{10}$ heterocyclic group, and the C$_3$-C$_{10}$ heteroaryl group and the C$_3$-C$_{10}$ heterocyclic group include at least one heteroatom selected from the group consisting of N, O, and S.

2. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein R$_1$ is hydrogen; or a C$_1$-C$_{13}$ alkyl group;

A is hydrogen; a C$_1$-C$_{13}$ alkyl group; a C$_6$-C$_{10}$ aryl group; a C$_3$-C$_{10}$ cyclic group; a C$_3$-C$_{10}$ heteroaryl group; a C$_3$-C$_{10}$ heterocyclic group; or —C(O)—(C$_1$-C$_{13}$ alkyl); and Y is a C$_6$-C$_{10}$ aryl group.

3. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the compound is the compound of Formula 1, and in Formula 1 above, R$_1$ is hydrogen; or a C$_1$-C$_{13}$ alkyl group;

A is a C$_6$-C$_{10}$ aryl group; a C$_3$-C$_{10}$ cyclic group; a C$_3$-C$_{10}$ heteroaryl group; or a C$_3$-C$_{10}$ heterocyclic group;

Y is a C$_6$-C$_{10}$ aryl group;

L$_1$, L$_3$ and L$_4$ are each independently selected from the group consisting of —NR$_5$C(O)—; and —C(O)NR$_5$—; and L$_2$ is

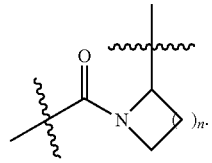

4. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the compound is the compound of Formula 1, and in Formula 1 above, R$_1$ is hydrogen; or a C$_1$-C$_{13}$ alkyl group;

A is a C$_6$-C$_{10}$ aryl group; a C$_3$-C$_{10}$ cyclic group; a C$_3$-C$_{10}$ heteroaryl group; or a C$_3$-C$_{10}$ heterocyclic group;

Y is a C$_6$-C$_{10}$ aryl group;

L$_1$ and L$_2$ are each independently selected from the group consisting of —NR$_5$C(O)—; and —C(O)NR$_5$—; and L$_3$ is

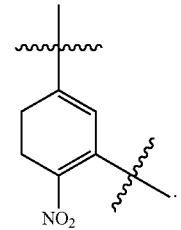 [SMILES: *C1=CC(*)=C([N+](=O)[O-])CC1]

5. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the compound is the compound of Formula 2, and in Formula 2 above,
$R_1$ is hydrogen; or a $C_1$-$C_{13}$ alkyl group;
A is a $C_6$-$C_{10}$ aryl group; a $C_3$-$C_{10}$ cyclic group; a $C_3$-$C_{10}$ heteroaryl group; or a $C_3$-$C_{10}$ heterocyclic group;
Y is a $C_6$-$C_{10}$ aryl group; and
$L_1$ is selected from the group consisting of —$NR_5C(O)$—; and —$C(O)NR_5$—.

6. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the compound is the compound of Formula 3, and in Formula 3 above,
$R_1$ is hydrogen; or a $C_1$-$C_{13}$ alkyl group;
A is a $C_6$-$C_{10}$ aryl group; a $C_3$-$C_{10}$ cyclic group; a $C_3$-$C_{10}$ heteroaryl group; or a $C_3$-$C_{10}$ heterocyclic group;
Y is a $C_6$-$C_{10}$ aryl group;
$L_1$ is selected from the group consisting of —$NR_5C(O)$—; and —$C(O)NR_5$—; and
$R_2$ is —$CH_2$—.

7. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the compound is the compound of Formula 4, and in Formula 4 above,
$R_1$ is hydrogen; or a $C_1$-$C_{13}$ alkyl group;
A is a $C_6$-$C_{10}$ aryl group; a $C_3$-$C_{10}$ cyclic group; a $C_3$-$C_{10}$ heteroaryl group; or a $C_3$-$C_{10}$ heterocyclic group;
Y is a $C_6$-$C_{10}$ aryl group;
$L_1$ and $L_2$ are each independently selected from the group consisting of —$NR_5C(O)$—; and —$C(O)NR_5$—; and
$R_2$ and $R_3$ are —$CH_2$—.

8. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the compound is the compound of Formula 5, and in Formula 5 above,
$R_1$ is hydrogen; or a $C_1$-$C_{13}$ alkyl group;
A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; and
Y is a $C_6$-$C_{10}$ aryl group.

9. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the compound is the compound of Formula 6, and in Formula 6 above,
$R_1$ is hydrogen; or a $C_1$-$C_{13}$ alkyl group;
A is a $C_6$-$C_{10}$ aryl group; a $C_3$-$C_{10}$ cyclic group; a $C_3$-$C_{10}$ heteroaryl group; or a $C_3$-$C_{10}$ heterocyclic group; and
Y is a $C_6$-$C_{10}$ aryl group.

10. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the compound is selected from the group consisting of the following compound Nos. 1 to 57:

(Compound No. 1)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 2)
(R)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 3)
(R)—N-(1-(((S)-1-(dimethylamino)-4-methyl-1-oxopentan-2-yl)carbamoyl)cyclopropyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 4)
(S)—N-(1-(((S)-1-(dimethylamino)-4-methyl-1-oxopentan-2-yl)carbamoyl)cyclopropyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 5)
(R)—N-(2-(((S-1-(dimethylamino)-4-methyl-1-oxopentan-2-yl)amino)-2-oxoethyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 6)
(S)—N-(2-(((S-1-(dimethylamino)-4-methyl-1-oxopentan-2-yl)amino-2-oxoethyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 7)
(R)—N—((S)-3-methyl-1-oxo-1-(((R)-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-phenylalanyl)pyrrolidine-2-carboxamide;

(Compound No. 8)
(R)—N—((S)-3-methyl-1-oxo-1-(((R)-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 9)
(S)—N—((S)-3-methyl-1-oxo-1-(((R-1-phenylethyl)amino)butan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide;

(Compound No. 10)
(R)—N-(1-(((R)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-D-valyl)pyrrolidine-2-carboxamide, (Compound No. 11)
(S)—N—(((S-1-(dimethylamino)-4-methyl-1-oxopentan-2-yl)amino)-1-oxo-3-phenylpropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide, (Compound No. 12)
(S)—N-(1-(((S)-1-(dimethylamino)-4-methyl-1-oxopentan-2-yl)carbamoyl)cyclobutyl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide,
(Compound No. 13)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)piperidine-2-carboxamide,
(Compound No. 14)
(S)—N-(1-((2-(dimethylamino)-2-oxoethyl)amino)-2-methyl-1-oxopropan-2-yl)-1-((4-methyl-3-(1-methyl-7-((6-methylpyridin-3-yl)amino)-2-oxo-1,4-dihydropyrimido[4, 5-d]pyrimidin-3(2H)-yl)benzoyl)-L-valyl)pyrrolidine-2-carboxamide;
(Compound No. 15)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)azetidine-2-carboxamide,
(Compound No. 16)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-isoleucyl)pyrrolidine-2-carboxamide,
(Compound No. 17)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-alanyl)pyrrolidine-2-carboxamide,
(Compound No. 18)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)glycyl)pyrrolidine-2-carboxamide,
(Compound No. 19)
(S)-1-((S)-2-cyclohexyl-2-((4-methyl-3-(1-methyl-7-((6-methylpyridin-3-yl)amino)-2-oxo-1,4-dihydropyrimido[4,5-d]pyrimidin-3(2H)-yl)benzamido)acetyl)-N-(1-(((S)-1-dimethylamino)-4-methyl-1-oxopentan-2-yl)amino)-2-methyl-1-oxopropan-2-yl]pyrrolidine-2-carboxamide;
(Compound No. 20)
(S)—N-(1-(((S)-1-(dimethylamino)-4-methyl-1-oxopentan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-lucyl)pyrrolidine-2-carboxamide,
(Compound No. 21)
(S)—N-(1-(((S)-1-(dimethylamino)-4-methyl-1-oxopentan-2-yl)amino)-2-methyl-1-oxopropan-2-yl)-1-((S)-2-((4-methyl-3-(1-methyl-7-((6-methylpyridin-3-yl)amino)-2-oxo-1,4-dihydropyrimido[4,5-d]pyrimidin-3(2H)-yl)benzamido)pentanoyl)pyrrolidine-2-carboxamide;
(Compound No. 22)
(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide,
(Compound No. 23)
(R)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-valyl)pyrrolidine-2-carboxamide,
(Compound No. 24)
(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-phenylalanyl)pyrrolidine-2-carboxamide,
(Compound No. 25)
(S)—N-(1-(((S)-1-(dimethylamino)-3-methyl-1-oxobutan-2-yl)amino)-2-methyl-1-oxopropan-2-yl)-1-((4-methyl-3-(1-methyl-7-((6-methylpyridin-3-yl)amino)-2-oxo-1,4-dihydropyrimido[4,5-d]pyrimidin-3(2H)-yl)benzoyl)-L-alanyl)pyrrolidine-2-carboxamide,
(Compound No. 26)
(S)-3-benzyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 27)
(S)-3-(3-fluorobenzyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 28)
(S)-3-(4-fluorobenzyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 29)
(S)—N-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-methylbenzyl)-2-oxo-5-phenyl-2,3-dihydro-1H-benzo[e][1,4]diazepine-8-carboxamide,
(Compound No. 30)
(S)-3-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 31)
(S)-1-benzyl-3-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 32)
(R)-3-((R)-sec-butyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide,
(Compound No. 33)
(S)-1-benzyl-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 34)
(S)-3-benzyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide, (Compound No. 35)
(R)-3-benzyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide, (Compound No. 36)
(R)-3-benzyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 37)
(S)-3-isobutyl-1-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 38)
(S)-1-allyl-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 39)
(S)-1,3-diisobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 40)
(S)-3-isobutyl-1,5-dimethyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide, (Compound No. 41)
(S)-1-benzyl-3-isobutyl-5-methyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-2,3-dihydro-1H-benzo[e][1,4]diazepine-8-carboxamide, (Compound No. 42)
(S)-3-isobutyl-1-(2-methoxyethyl)-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 43)
(S)-1-(2-(benzylamino)-2-oxoethyl)-3-isobutyl-N-(4-methyl-3-(1-methyl-7-((6-methylpyridin-3-yl)amino)-2-oxo-1,4-dihydropyrimido[4,5-d]pyrimidin-3(2H)-yl)phenyl)-2-oxo-5-phenyl-2,3-dihydro-1H-benzo[e][1,4]diazepine-8-carboxamide, (Compound No. 44)
(S)-2-(5-(but-3-en-1-yl)-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide;

(Compound No. 45)
(S)-2-(5-(but-3-en-1-yl)-1-methyl-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide, (Compound No. 46)
(S)-2-(1-benzyl-5-(but-3-en-1-yl)-2-oxo-2,3-dihydro-1H-benzo[e][1,4]diazepin-3-yl)-N-(4-methyl-3-(1-methyl-7-((6-methylpyridin-3-yl)amino)-2-oxo-1,4-dihydropyrimido[4,5-d]pyrimidin-3(2H)-yl)phenyl)acetamide, (Compound No. 47)
(3S,4S)—$N^3$-benzyl-$N^4$-(4-chlorobenzyl)-1-(4-methyl-3-(1-methyl-7-((6-methylpyridin-3-yl)amino)-2-oxo-1,4-dihydropyrimido[4,5-d]pyrimidin-3(2H)-yl)benzoyl)pyrrolidine-3,4-dicarboxamide, (Compound No. 48)
(3S,4S)—$N^3$-(2-(1H-indol-3-yl)ethyl-$N^4$-(4-chlorobenzyl)-1-(4-methyl-3-(1-methyl-7-((6-methylpyridin-3-yl)amino)-2-oxo-1,4-dihydropyrimido[4,5-d]pyrimidin-3(2H)-yl)benzo yl)pyrrolidine-3,4-dicarboxamide;

(Compound No. 49)
3-isobutoxy-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide, (Compound No. 50)
3-(2-(1H-indol-3-yl)ethoxy)-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide, (Compound No. 51)
3-(4-methoxyphenethoxy)-N-(4-methyl-3-(1-methyl-7-((6-methylpyridin-3-yl)amino)-2-oxo-1,4-dihydropyrimido[4,5-d]pyrimidin-3(2H)-yl)phenyl)-4-nitrobenzamide, (Compound No. 52)
3-isobutoxy-N-(2-((4-methyl-3-(1-methyl-7-((6-methylpyridin-3-yl)amino)-2-oxo-1,4-dihydropyrimido[4,5-d]pyrimidin-3(2H)-yl)phenyl)amino)-2-oxoethyl)-4-nitrobenzamide, (Compound No. 53)
(S)-3-isobutoxy-N-(1-((4-methyl-3-(1-methyl-7-((6-methylpyridin-3-yl)amino)-2-oxo-1,4-dihydropyrimido[4,5-d]pyrimidin-3(2H)-yl)phenyl)amino)-2-oxopropan-2-yl)-4-nitrobenzamide, (Compound No. 54)
(S)-3-isobutoxy-N-(4-methyl-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopentan-2-yl)-4-nitrobenzamide;

(Compound No. 55)
(S)—N-3-(1H-indol-3-yl)-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopropan-2-yl)-3-isobutoxy-4-nitrobenzamide;

(Compound No. 56)
(S)-3-(4-methoxyphenethoxy)-N-1-((4-methyl-3-(1-methyl-7-((6-methylpyridin-3-yl)amino)-2-oxo-1,4-dihydropyrimido[4,5-d]pyrimidin-3(2H)-yl)phenyl)amino)-1-oxopropan-2-yl)-4-nitrobenzamide, and (Compound No. 57) 2,2,2-trichloroethyl
(3S,4S)-3-((4-chlorobenzyl)carbamoyl)-4-((4-methyl-3-(1-methyl-7-((6-methylpyridin-3-yl)amino)-2-oxo-1,4-dihydropyrimido[4,5-d]pyrimidin-3(2H)-yl)phenyl)carbamoyl)pyrrolidine-1-carboxylate.

11. The compound selected from a pyrimido[4,5-d]pyrimidin-2-one derivative compound represented by any one of the following Formulae 1 to 6, a pharmaceutically acceptable salt thereof, a hydrate thereof and a stereoisomer thereof according to claim 1, wherein the pharmaceutically acceptable salt is a salt of an inorganic or organic acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

* * * * *